(12) United States Patent
LaBorde

(10) Patent No.: US 10,192,636 B1
(45) Date of Patent: Jan. 29, 2019

(54) BAGGAGE SYSTEM, RFID CHIP, SERVER AND METHOD FOR CAPTURING BAGGAGE DATA

(71) Applicant: Brain Trust Innovations I, LLC, Alpharetta, GA (US)

(72) Inventor: David LaBorde, Alpharetta, GA (US)

(73) Assignee: Brain Trust Innovations I, LLC, Alpharetta, GA (US)

( * ) Notice: Subject to any disclaimer, the term of this patent is extended or adjusted under 35 U.S.C. 154(b) by 0 days.

(21) Appl. No.: 16/115,097

(22) Filed: Aug. 28, 2018

Related U.S. Application Data

(63) Continuation of application No. 15/976,832, filed on May 10, 2018, which is a continuation of application No. 15/891,114, filed on Feb. 7, 2018, now Pat. No. 10,014,076, which is a continuation-in-part of application No. 15/704,494, filed on Sep. 14, 2017, now Pat. No. 9,928,342, which is a continuation-in-part of application No. 15/592,116, filed on May 10, 2017, now Pat. No. 9,848,827, which is a continuation of application No. 15/390,695, filed on Dec. 26, 2016, now Pat. No. 9,679,108, which is a continuation of application No. 15/004,535, filed on Jan. 22, 2016, now Pat. No. 9,569,589.

(Continued)

(51) Int. Cl.
| | |
|---|---|
| G06K 7/10 | (2006.01) |
| G06N 3/04 | (2006.01) |
| G06N 3/08 | (2006.01) |
| G06Q 10/08 | (2012.01) |
| G16H 10/65 | (2018.01) |

(52) U.S. Cl.
CPC ......... *G16H 10/65* (2018.01); *G06K 7/10366* (2013.01); *G06N 3/04* (2013.01); *G06N 3/08* (2013.01); *G06Q 10/08* (2013.01)

(58) Field of Classification Search
CPC .......... G06K 7/10366; G06K 7/10009; G06K 19/0723; G06K 7/10316; G06K 7/10356; G06K 7/0008; G06K 19/0717; G06K 7/10257
USPC ........................................................ 340/10.1
See application file for complete search history.

(56) References Cited

U.S. PATENT DOCUMENTS

| | | |
|---|---|---|
| 7,158,030 B2 | 1/2007 | Chung |
| 7,388,506 B2 | 6/2008 | Abbott |

(Continued)

OTHER PUBLICATIONS

Zafari et al., Micro-location for Internet of Things equipped Smart Buildings, [online], Jan. 7, 2015 [retrieved on Sep. 3, 2015]. Retrieved from the Internet:<URL:http://arxiv.org/abs/1501.01539>.

(Continued)

*Primary Examiner* — Mark S Blouin
(74) *Attorney, Agent, or Firm* — Culpepper IP, LLLC; Kerry S. Culpepper

(57) ABSTRACT

A baggage system includes a plurality of RFID tags affixed to baggage items, a data collection engine, client devices and backend devices. The backend devices include trained machine learning models, business logic, and attributes of a plurality of events. A plurality of data collection engines and baggage terminal systems send attributes of new events to the backend devices. The backend devices can track the baggage items and predict particular outcomes of new events based upon the attributes of the new events utilizing the trained machine learning models.

19 Claims, 40 Drawing Sheets

Related U.S. Application Data

(60) Provisional application No. 62/113,356, filed on Feb. 6, 2015.

(56) References Cited

U.S. PATENT DOCUMENTS

| | | | |
|---|---|---|---|
| 7,479,887 | B2 | 1/2009 | Meyer |
| 7,586,417 | B2 | 9/2009 | Chisholm |
| 7,772,981 | B1 | 8/2010 | Lambert et al. |
| 7,850,893 | B2 | 12/2010 | Chisholm et al. |
| 7,852,221 | B2 | 12/2010 | Tuttle |
| 7,875,227 | B2 | 1/2011 | Chisholm |
| 7,922,961 | B2 | 4/2011 | Chisholm et al. |
| 7,973,664 | B1 | 7/2011 | Lambert et al. |
| 8,097,199 | B2 | 1/2012 | Abbott et al. |
| 8,098,162 | B2 | 1/2012 | Abbott et al. |
| 8,120,484 | B2 | 2/2012 | Chisholm |
| 8,181,875 | B2 | 5/2012 | Nishido |
| 8,212,226 | B2 | 7/2012 | Chisholm |
| 8,296,247 | B2 | 10/2012 | Zhang et al. |
| 8,478,535 | B2 | 7/2013 | Jojic et al. |
| 2010/0190436 | A1 | 7/2010 | Cook et al. |
| 2011/0291809 | A1 | 12/2011 | Niemiec |
| 2013/0002034 | A1 | 1/2013 | Onizuka et al. |
| 2015/0317589 | A1 | 11/2015 | Anderson et al. |

OTHER PUBLICATIONS

Pivato et al., "Experimental Assessment of a RSS-based Localization Algorithm in Indoor Environment", [online], May 2010 [retrieved on Sep. 4, 2015]. Retrieved from the Internet: <http://www.researchgate.net/profile/Paolo_Pivato/publication/224146714_Experimental_Assessment_of_a_RSSbased_Localization_Algorithm_in_Indoor_Environment/links/0912f502b6b29f22ea000000.pdf>.

IMPINJ, White Paper "New Thinking on an Old Challenge: Improving Healthcare Asset Management with RAIN RFID Technology", [online], 2017 [retrieved on Nov. 16, 2017]. Retrieved from the Internet: <https://www.impinj.com/media/2046/impinj-healthcare-asset-management-white-paper.pdf>.

Wong et al., "30 Years of Multidimensional Multivariate Visualization", [online], 1997 [retrieved on Aug. 12, 2016]. Retrieved from the Internet: <http://citeseerx.ist.psu.edu/viewdoc/download?doi=10.1.1.30.4639&rep=rep1&type=pdf>.

Bolic et al., "Proximity Detection with RFID: A Step Toward the Internet of Things", Apr. 23, 2015, Pervasive Computing IEEE, vol. 14 Issue:2, Published by IEEE.

Erica Drazen, "Using Tracking Tools to Improve Patient Flow in Hosptals", [online], Apr. 2011 [retrieved on Feb. 15, 2018]. Retrieved from the Internet: <https://www.chcf.org/publication/using-tracking-tools-to-improve-patient-flow-in-hospitals/>.

Philip Heacock, "What is IATA Resolution 753?", [online], Aug. 26, 2016 [retrieved on Apr. 25, 2018]. Retrieved from the Internet: <http://www.aviationpros.com/article/12214806/what-is-iata-resolution-753/>.

Jadak, A Novanta Company, "ThingMagic IZAR", [online], Mar. 27, 2018 [retrieved on Apr. 18, 2018]. Retrieved from the Internet: <https://www.jadaktech.com/download-product-pdf-sf?download_file=https://www.jadaktech.com/wp-content/uploads/2018/04/IZAR-Product-Spec-Sheet_04_19_18.pdf&prodID=17307>.

Lyngsoe Systems, "Lyngsoe LIVE Logistics—BagDrop Reader", [online], Publication Date Not Stated [retrieved on May 9, 2018]. Retrieved from the Internet: <https://www.lyngsoesystems.com/en/login/?referer=/media/1719/074968311-bagdrop_reader-uk.pdf>.

Lyngsoe Systems, "Lyngsoe LIVE Logistics—Pier and Claim Reader", [online], Publication Date Not Stated [retrieved on May 9, 2018]. Retrieved from the Internet: <https://www.lyngsoesystems.com/media/1876/074968222-pier_and_claim_reader-uk.pdf>.

Lyngsoe Systems, "Lyngsoe Systems Launch RFID Belt Loader Reader", [online], Feb. 28, 2017 [retrieved on May 9, 2018]. Retrieved from the Internet: <https://www.lyngsoesystems.com/en/news/lyngsoe-systems-launch-rfid-belt-loader-reader/>.

Lyngsoe Systems, "Lyngsoe LIVE Logistics—Belt Loader Reader", [online], Publication Date Not Stated [retrieved on May 9, 2018]. Retrieved from the Internet: <https://www.lyngsoesystems.com/media/1721/074968211-belt_loader_reader-uk.pdf>.

Ann Grackin et al., "RFID Hardware: What You Must Know", RFID Technology Series, Jun. 2006.

Lyngsoe Systems, "PR34 X—Belt Loader RFID Reader User Guide", Apr. 16, 2016.

Lyngsoe Systems, "ADM User Manual", Sep. 21, 2010.

920

Event 1: Baggage Item ID on Conveyor Belt, Time, Location
Event 2: Baggage Item handled by ID of Baggage Handler at Start Time, Location, End Time
Event 3: Baggage Item on transport device at Start Time, Location, End Time
Event 4: Baggage Item off transport device at Time, Location

DCE

940

Baggage Item ID Handled by ID at Location ID

Server

FIG. 14

Data Fields/Properties

|  | Property 1 | Property 2 | Property 3 | ... | Property N |
|---|---|---|---|---|---|
| Data 1 |  |  |  |  |  |
| Data 2 |  |  |  |  |  |
| Data 3 |  |  |  |  |  |
| ... |  |  |  |  |  |
| Data N |  |  |  |  |  |

Collected Data

FIG. 17

Value Plotted on Actual Range

Equivalent Value Plotted on Normalization Scale

One-of-N Encoding

Equilateral Encoding

```
MODEL VALIDATION PROCEDURE STARTING....

Input: 1.0, 1.0, 1.0, 1.0, 1.0, 1.0, 1.0, 1.0, 1.0, 1.0    Ideal: 0.0    Predicted: 1.4458121796750ZE-05
Input: 1.0, 1.0, 1.0, 1.0, 1.0, 1.0, 1.0, 1.0, 1.0, 1.0    Ideal: 0.0    Predicted: 5.326706584412AE-05
Input: 1.0, 1.0, 1.0, 1.0, 1.0, 1.0, 0.0, 0.0, 0.0, 0.0    Ideal: 0.0    Predicted: 9.373089815Z9282E-05
Input: 1.0, 1.0, 1.0, 1.0, 1.0, 1.0, 1.0, 1.0, 1.0, 1.0    Ideal: 1.0    Predicted: 0.9760131498956893
Input: 1.0, 1.0, 1.0, 1.0, 1.0, 1.0, 1.0, 1.0, 1.0, 1.0    Ideal: 0.0    Predicted: 0.018197914964945?
Input: 1.0, 1.0, 1.0, 1.0, 1.0, 1.0, 0.0, 0.0, 0.0, 0.0    Ideal: 0.0    Predicted: 1.4458121796750ZE-05
Input: 1.0, 1.0, 1.0, 1.0, 1.0, 1.0, 1.0, 1.0, 1.0, 1.0    Ideal: 1.0    Predicted: 0.9760131498956893

----- MODEL VALIDATION COMPLETE -----
```

FIG. 33D

Exemplary Regression Task-Supervised Learning
(2D Example Shown for Simplicity)

BAGGAGE SYSTEM, RFID CHIP, SERVER AND METHOD FOR CAPTURING BAGGAGE DATA

CROSS-REFERENCE TO RELATED APPLICATIONS

The present application is a continuation of U.S. patent application Ser. No. 15/976,832 filed on May 10, 2018, which is a continuation of U.S. patent application Ser. No. 15/891,114 filed on Feb. 7, 2018, which is a continuation-in-part of U.S. patent application Ser. No. 15/704,494 filed on Sep. 14, 2017 now U.S. Pat. No. 9,928,342, which is a continuation-in-part of U.S. patent application Ser. No. 15/592,116 filed on May 10, 2017 now U.S. Pat. No. 9,848,827, which is a continuation of U.S. patent application Ser. No. 15/390,695 filed on Dec. 26, 2016 now U.S. Pat. No. 9,679,108, which is a continuation of U.S. patent application Ser. No. 15/004,535 filed on Jan. 22, 2016 now U.S. Pat. No. 9,569,589, which claims the benefit of U.S. Provisional Patent Application No. 62/113,356 filed on Feb. 6, 2015, the contents all of which are incorporated herein by reference.

TECHNICAL FIELD

The technical field generally relates to a baggage system including a data collection engine, a plurality of baggage items including radio-frequency identification chips, and a server.

BACKGROUND

A radio-frequency Identification (RFID) chip can transmit information to a reader in response to an interrogation signal or polling request from the reader. The RFID chip can be incorporated in a tag (RFID tag) which is placed on items such as baggage so that information can be passively captured. In this disclosure the term baggage item refers generally to items such as suitcases, packages, etc. entrusted to airlines and/or shipping companies at airports for shipping to a destination.

An RFID tag can be an active-type with its own power source, or a passive-type or battery-assisted passive type with no or limited power source. Both the passive-type and battery-assisted passive type will be referred to here as passive-type for sake of brevity. Placing an active-type RFID tag on some items may not be feasible do to financial considerations, weight, etc. On the other hand, placing a passive-type RFID tag on items may be more feasible; however, a power source will be needed to passively obtain information. Therefore, a device that can provide power to the RFID tag on the item as well as obtain the information from the RFID tag would be beneficial.

In a conventional baggage system, a baggage item is checked in at an initiating checkpoint such as, for example, a counter of an airport. Information indicative of the origin, destination(s), and customer name are printed on a tag which is placed on the baggage. The baggage item may be handled at many intermediate checkpoints, each of which themselves may be comprised of interim steps or processes, such as (i) loading on a transport to be transported to an airplane, (ii) loading from the transport onto the airplane, (iii) loading from the airplane onto a transport at the destination airport, and (iv) loading from the transport onto a carousel at the destination airport for pickup by the customer, to name only a few exemplary checkpoints.

SUMMARY

One issue with a current baggage system is the lack of ability to effectively track baggage to a precise location intermediate to the origin and destination checkpoints that exist in the current system. For example, if baggage is not sent to the preferred destination by the preferred time, referred to in this disclosure generally as "deviated" or "lost", it is difficult to find the precise location of the baggage, at what point the baggage deviated from the appropriate path, and who or what might be responsible for the deviation. Other issues include identifying smuggled baggage, stolen baggage, baggage handlers engaging in 'spurious' activity, etc.

A system that can accurately track the path of baggage items would be preferable. It would be further preferable if such a system could take advantage of artificial intelligence techniques such as machine learning to predict when a baggage will be deviated or the probability that a given piece of baggage may not arrive at the intended destination at the scheduled time so that the system can be further improved to limit baggage loss, provide insight that may allow scenarios in which baggage is predicted to have a high probability of being lost to be remediated, and to improve service recovery.

According to various embodiments, a baggage system includes a data collection engine (DCE), a plurality of RFID chips associated with a baggage item, a baggage handler, and a transport device, and a server device. The RFID chip can be incorporated in a tag (RFID tag) which is placed on the baggage item, transport device or an identification of the baggage handler so that information can be passively captured. An RFID tag can be an active-type with its own power source, or a passive-type or battery-assisted passive type with no or limited power source. Instructions configure the server device controller to: create a model such as a neural network model (NNM) for modeling events; train and validate the NNM by supervised learning; calculate an output value for new events based upon the trained NNM; classify the output value; and reassign resources to certain categories. For example, the event can be a baggage item with certain parameters (date, weight, location, etc.) and classification of the output value can be a Boolean value such as deviated (i.e., lost), security risk (i.e., smuggled, contraband), shrinkage (i.e., larceny or theft) and a predicted time of arrival and arrival location (i.e., on what carousel and when).

The instructions can also configure the controller to create a self-organizing map (SOM) network for modeling events, the SOM including a plurality of network nodes, a plurality of input nodes representing input attributes of the past events, wherein the plurality of network nodes is arranged in a grid or lattice in a fixed topological position, each of the plurality of input nodes is connected to all of the plurality of network nodes by a plurality of synaptic weights. The controller can generate an output value of the SOM network based upon input attributes for the event, wherein the output value is a graphical display showing a particular category for the event.

BRIEF DESCRIPTION OF THE DRAWINGS

The accompanying figures, in which like reference numerals refer to identical or functionally similar elements, together with the detailed description below are incorporated in and form part of the specification and serve to further illustrate various exemplary embodiments and explain various principles and advantages in accordance with the present invention.

FIG. 14 is an illustration of an exemplary conceptual message generated by the DCE to be sent to the server device.

FIG. 17 is an illustration of an exemplary data set for input attributes for various events.

FIGS. 33A-33D are illustrations of validation outputs when validating a trained NNM.

DETAILED DESCRIPTION

In overview, the present disclosure concerns a system which includes a Data Collection Engine (DCE), an RFID tag associated with items such as, for example, baggage, transport devices, identifications of baggage handlers, back-end devices such as one or more server devices and a throughput management device (TMD), and a plurality of client devices.

The instant disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1:
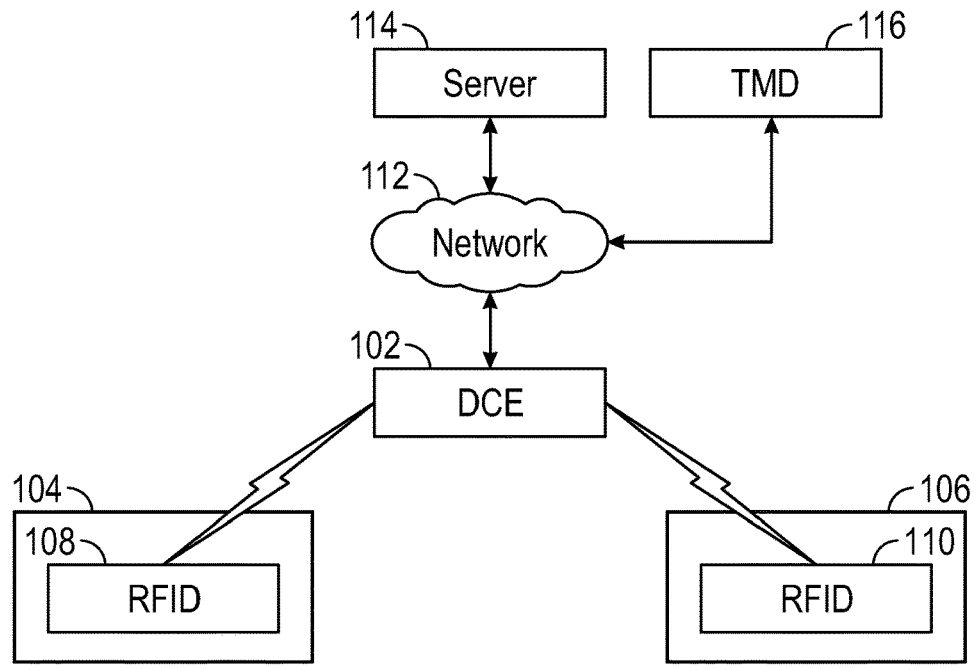
FIG. 1 illustrates an exemplary core operating environment in which a Data Collection Engine (DCE) receives data from RFID tags and transmits the data to a server device via a connection to a network and a throughput management device (TMD) exchanges data with the server device via a connection to the network.
Figure 15A:
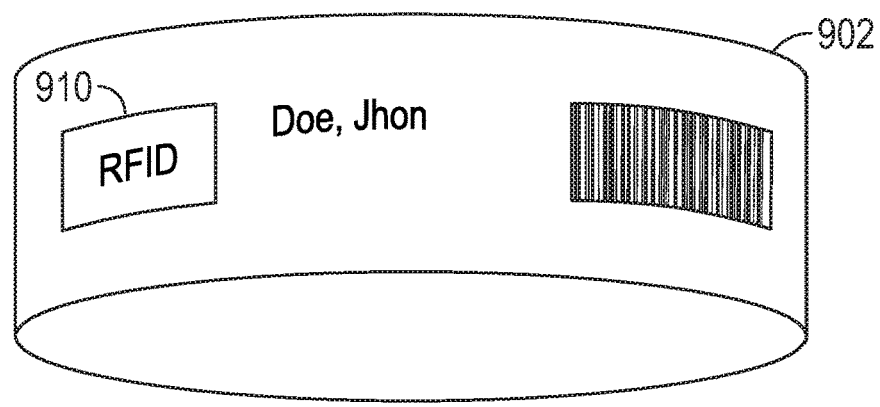
FIGS. 15A-15B are illustrations of identifications including RFID tags.
Figure 15B:
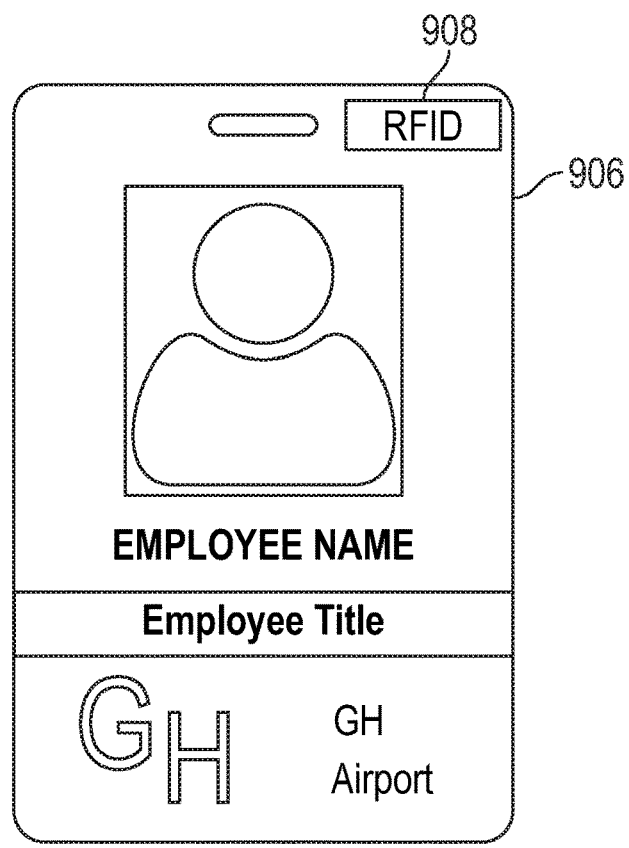

Referring to FIG. 1, an exemplary operating environment in which the system according to various embodiments can be implemented will be discussed. The environment includes a DCE 102 communicating with first and second RFID tags 108, 110 which can be disposed in separate first and second rooms 104, 106. Each of the RFID tags 108, 110 is associated with an item such as a baggage item 2500 (FIG. 12) and baggage handler identification such as a wrist band 902 (FIG. 15A) or ID badge 906 (FIG. 15B). As discussed more fully below, the communication between the RFID tags 108, 110 and the DCE 102 is preferably wireless; however, wireline communication or a combination of wireless and wireline communication can also be used in some cases. The DCE 102, although shown here as a single entity, can include sub-portions in each of the rooms 104, 106. Moreover, as discussed later, the system likely includes many DCEs (see FIG. 11). The DCE 102 communicates with one or more server devices (represented generally by and referred to hereon as "server") 114 via a connection to a network 112 such as a local area network (LAN), wide area network (WAN), the Internet, etc. A TMD 116 can communicate with the server 114 and the DCE 102 via a connection to the network 112. The first and second rooms 104, 106 can be, for example, separate rooms of an airport facility. The communication between the DCE 102 and the RFID tags 108, 110, between the DCE 102 and the server 114 or TMD 116, and/or between the server 114 and the TMD 116 can be encrypted or unencrypted. The network 112 can be, for example, a private LAN for the airport facility. The server 114 can be a computing device local to the facility. On the other hand, the network 112 can be the Internet, the DCE 102 can be local to the facility and the server 114 can be one or more remote computing devices. The DCE 102 can be a reader device such as, for example, the TSL 1128 Handheld RAIN RFID reader made by IMPINJ™. One of ordinary skill in the art should appreciate that the server 114 can represent entities necessary for providing cloud computing such as infrastructure and service providers.

Figure 2:
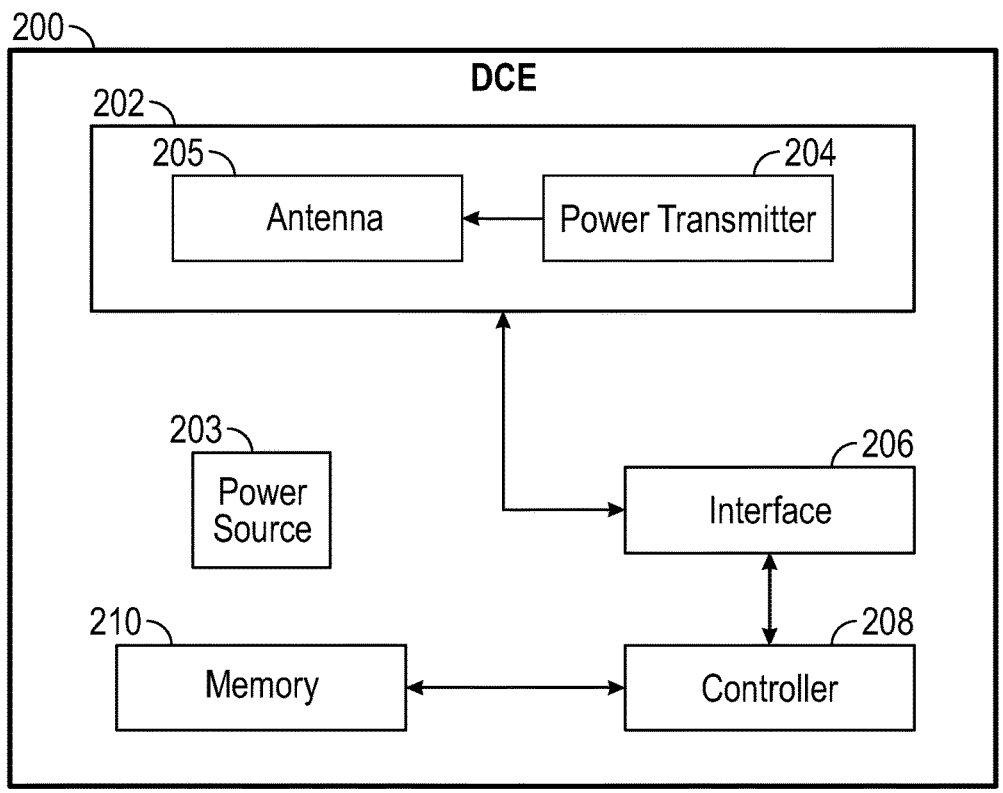
FIG. 2 is a block diagram illustrating exemplary portions of the DCE.

Referring to the block diagram of FIG. 2, portions of an exemplary DCE 200 will be discussed. The DCE 200 includes a transceiver 202, a power source 203, an interface 206, a controller 208 and one or more memory portions depicted by memory 210.

Referencing the Open Systems Interconnection reference model (OSI model), the transceiver 202 can provide the physical layer functions such as modulating packet bits into electromagnetic waves to be transmitted and demodulating received waves into packet bits to be processed by higher layers (at interface 206). The transceiver 202 can include an antenna portion 205, and radio technology circuitry such as, for example, ZigBee, Bluetooth and WiFi, as well as an Ethernet and a USB connection. The transceiver 202 also includes a wireless power transmitter 204 for generating a magnetic field or non-radiative field for providing energy transfer from the power source 203 and transmitting the energy to, for example, an RFID tag by antenna portion 205. The power transmitter 204 can include, for example, a power transmission coil. The antenna portion 205 can be, for example, a loop antenna which includes a ferrite core, capacitively loaded wire loops, multi-turn coils, etc. In addition to energy transfer, the transceiver portion 202 can also exchange data with the RFID tag. Data transmission can be done at, for example, 1.56 MHz. The data can be encoded according to, for example, Amplitude Shift Keying (ASK). The transceiver 202 includes a power transmission system composed of the antenna 205 and the power transmitter 204.

The interface 206 can provide the data link layer and network layer functions such as formatting packet bits to an appropriate format for transmission or received packet bits into an appropriate format for processing by the controller 208. For example, the interface 206 can be configured to encode or decode according to ASK. Further, the interface 206 can be configured in accordance with the 802.11 media access control (MAC) protocol and the TCP/IP protocol for data exchange with the server via a connection to the network. According to the MAC protocol, packet bits are encapsulated into frames for transmission and the encapsulation is removed from received frames. According to the TCP/IP protocol, error control is introduced and addressing is employed to ensure end-to-end delivery. Although shown separately here for simplicity, it should be noted that the interface 206 and the transceiver 202 may be implemented by a network interface consisting of a few integrated circuits.

The memory 210 can be a combination of a variety of types of memory such as random access memory (RAM), read only memory (ROM), flash memory, dynamic RAM (DRAM) or the like. The memory 210 can store location information and instructions for configuring the controller 208 to execute processes such as generating messages representative and indicative of data and events received from RFID tags as discussed more fully below.

The controller 208 can be a general purpose central processing unit (CPU) or an application specific integrated circuit (ASIC). For example, the controller 208 can be implemented by a 32 bit microcontroller. The controller 208 and the memory 210 can be part of a core (not shown).

Figure 3A:
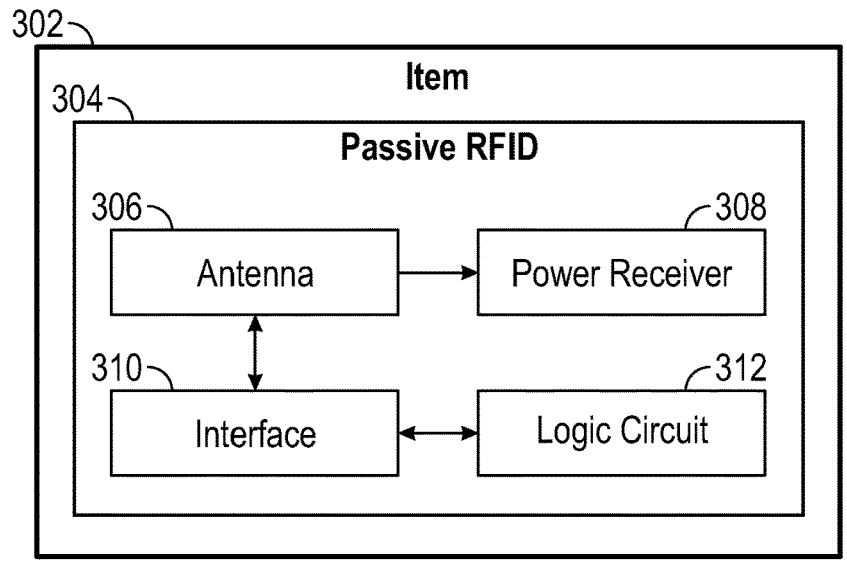
FIG. 3A is a block diagram illustrating exemplary portions of a passive-type RFID tag.

Referring to FIG. 3A, portions of an exemplary passive-type RFID tag 304 will be discussed. The RFID tag 304 can include an antenna portion 306, a power receiver 308, an interface 310 and a logic circuit 312. The antenna portion 306 can be a loop antenna which includes a ferrite core, capacitively loaded wire loops, multi-turn coils, etc., similar to the antenna portion 205 of the DCE 200. The power receiver 308 can include a power receiving coil for receiving power from the power transmission coil of the power transmitter 204 by electromagnetic coupling. The power receiver 308 can provide power to the chip 304 and/or charge a power source (not shown) such as a battery.

Generally, the logic circuit 312 generates data such as an identification of the RFID tag and/or the item to which it is affixed, state, location, and changes in any data or properties thereof over time, all of which will be referred to as item data. It should be noted that the item data includes situational data which refers to a) the identity of the RFID tag, the identity reference for a baggage, individual, facility plant, property, equipment to which the RFID tag is affixed, and b) the distance between an RFID tag and other RFID tags, the distance between the RFID tag and the DCE, the distance between the RFID and a client device such as smartphone, the identity and any identity references of the other RFID tags, DCEs and mobile client devices (i.e. smartphones) with which the RFID communicates, and any obtained from a sensor associated with i) the RFID tag or ii) another RFID tag, or client device (i.e. smartphone) with which the RFID communicates. Examples of the sensor data might be location in three dimensions, acceleration or velocity, displacement relative to some reference, temperature, pressure, to name a few.

The item data can also include data indicative of an event such as, for example, near field communication (NFC) established with the DCE or another RFID tag, a time duration for which the RFID tag 304 has been within a certain location, historical data, etc. Although not shown, the logic circuit 312 can include or be coupled to a non-volatile memory or other memory sources.

The interface 310 can format a received signal into an appropriate format for processing by the logic circuit 312 or can format the data received from the logic circuit 312 into an appropriate format for transmission. For example, the interface 310 can demodulate ASK signals or modulate data from the logic circuit 312 into ASK signals.

Figure 5:
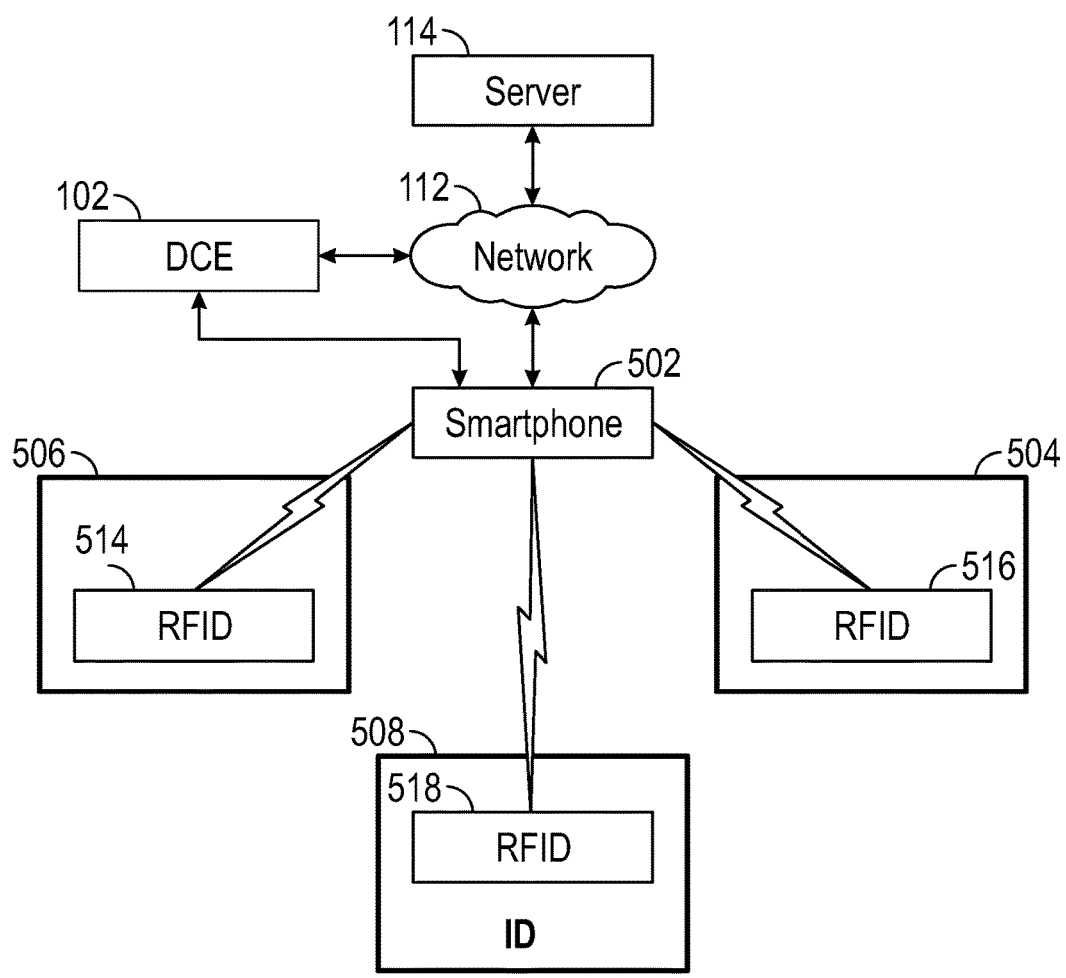
FIG. 5 illustrates an exemplary operating environment in which a smartphone acts as or together with the DCE to receive data from RFID chips associated with items according to a modification to the first embodiment.

The DCE can also be or include a device reader such as the smartphone 502 shown in FIG. 5 or fixed gateway readers such as, for example, the XARRAY, XSPAN and XPORTAL made by IMPINJ™ or fixed and handheld readers such as the SPEEDWAY R420, SPEEDWAY R220, SPEEDWAY R120, ATID AB700 and TSL 1128 also made by IMPINJ™. The DCE can include chips such as the INDY series chip (INDY RS2000, INDY RS1000, INDY RS500, INDY R2000 or INDY R500, etc.) also made by IMPINJ™.

Figure 3B:
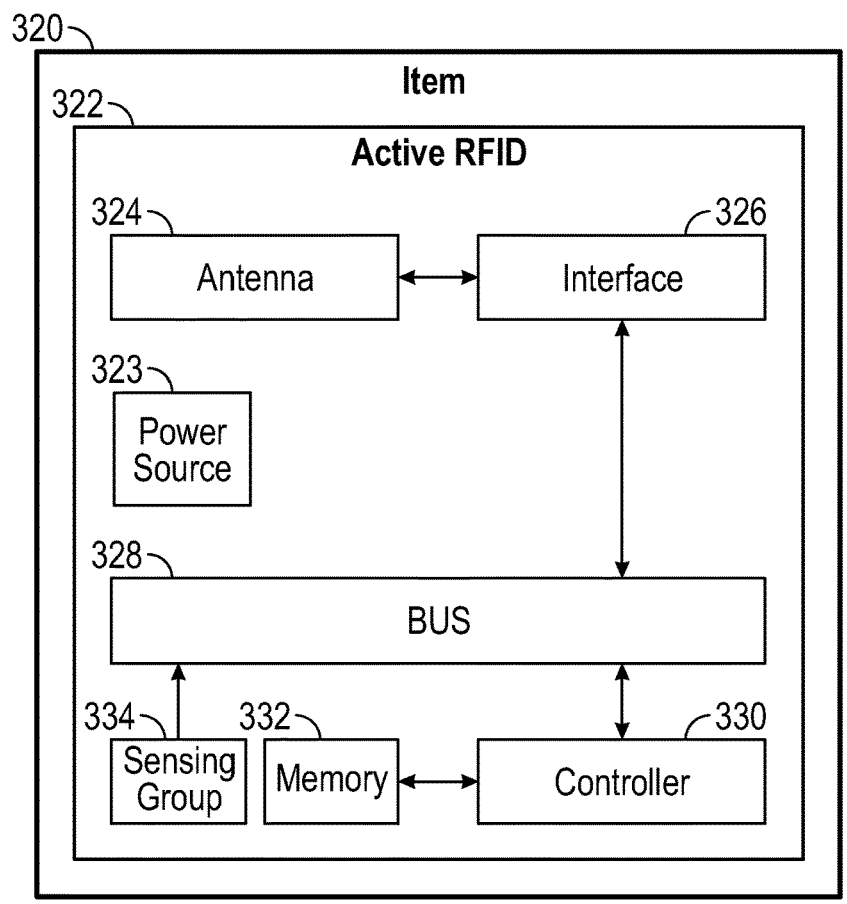
FIG. 3B is a block diagram illustrating exemplary portions of an active-type RFID tag.

Referring to FIG. 3B, circuit-level portions of the active-type RFID tag 322 on an item 320 will be discussed. The RFID tag 322 can include a power source 323, an antenna portion 324, an interface 326, a bus 328, a controller 330, a memory portion 332 and a sensing group 334. The power source 323 can be, for example, a battery. Although not shown, the tag 322 can also include a power management portion coupled to the power source 323.

The antenna portion 324 and interface 326 can be similar to those of the passive-type RFID tag 304. However, it should be noted that the antenna portion 324 can receive data from other passive-type and active-type RFID tags as well as the DCE and can send this and other data to the DCE, or other RFID tags.

The sensing group 334 includes sensing portions for sensing contact, motion characteristics such as an acceleration value, whether the chip is within a predetermined distance from another RFID tag, a distance from one or more other RFID tags and/or the DCE, and/or distance and angle from a baseline orientation. The sensing group 334 can include a set of accelerometers for determining the acceleration value of the item 320, a digital compass that collects orientation information about the item 322, a gyroscope for measuring angular rotation associated with the apparatus to provide an orientation value, a proximity sensor for detecting if the chip 322 is within a predetermined distance of another chip 322, a touch sensor layer and/or pressure sensor for sensing contact and magnitude of the pressure, and a geomagnetic sensor for sensing geomagnetic field strength. Preferably, the sensed motion characteristics include data represented in the time domain. The accelerometers can detect subtle movements along the three axial directions. The accelerometer reading, when combined with the data from the digital compass and/or the gyroscope, can facilitate motion detection. The sensing group 334 can include a separate OpenBeacon active tag or a Sense-a-Tag as described in "Proximity Detection with RFID: A Step Toward the Internet of Things" by Bolić et al., Pervasive Computing, IEEE, (Volume 14, Issue 2), published on April-June 2015, the contents of which are incorporated herein by reference. Further, in conjunction with or separately from the proximity sensor, the sensing group can include a distance sensor for measuring a distance to a target node such as another RFID chip. The distance sensor may be a received signal strength (RSS) indicator type sensor for measuring the RSS of a signal received from a target node such as the DCE or another RFID chip. The distance from the target node can be obtained by a plurality of RSS measurements.

The controller 330 is configured according to instructions in the memory 332 to generate messages to be sent to the DCE or another tag. Particularly, the controller 330 can be configured to send a registration message which includes identification data associated with the RFID tag 322 and thus the item 320. Further, in a case in which the RFID tag 322 wirelessly provides power to another passive-type RFID tag, the controller 330 can be configured to generate a message including identification data associated with the passive-type RFID tag, in combination with, or separately from its own identification data to the DCE.

The controller 330 can be configured to generate messages including data indicative of an event. These types of messages can be sent upon receiving a request from the DCE or another entity, upon occurrence of the event, or at regular intervals. Example events include near field communication established with another RFID tag, contact detected by the sensing group 334, positional information, a time duration of such contact and position, etc.

It should be noted that the passive-type RFID tag can also include a sensing group or be coupled to the sensing group. For example, the RFID tag 304 can be a Vortex passive RFID sensor tag which includes a LPS331AP pressure sensor. For example, the RFID chip 304 can be a MONZA X-8K DURA or X-2K DURA tag made by IMPINJ™ which include embedded sensors. Both active and passive types of sensors can include RSS measurement indicators. The controller or control logic can determine the distance from the RSS measurements based upon localization algorithms such as, for example, Centroid Location (CL), Weighted CL, or the Relative Span Exponentially Weighted Localization (REWL) algorithm as discussed in "Experimental Assessment of a RSS-based Localization Algorithm in Indoor Environment" by Pivato et al., IEEE Instrumentation and Measurement Technology Conference, published on May 2010, the contents of which are incorporated herein by reference. As mentioned above, the DCE 102 can store data regarding its fixed location (i.e. room 106). In this case, the physical location of the RFID tag 110 can be determined via the DCE 102. Alternatively, the RFID tags can obtain position from some external reference (i.e. a device with GPS or via a device that provides an indoor positioning system location reference, or WiFi hotspots, that themselves have a known location, which can somehow transmit WiFi ids to the RFID chips). This later approach, involving an external device other than the DCE 102, would occur via having the other external device communicate with the RFID tag and write location data to the RFID tag memory which is then sent along with any messages to the DCE. Further, the RFID tags could also be designed to record this location information from an external source upon being interrogated by a DCE.

Figure 9:
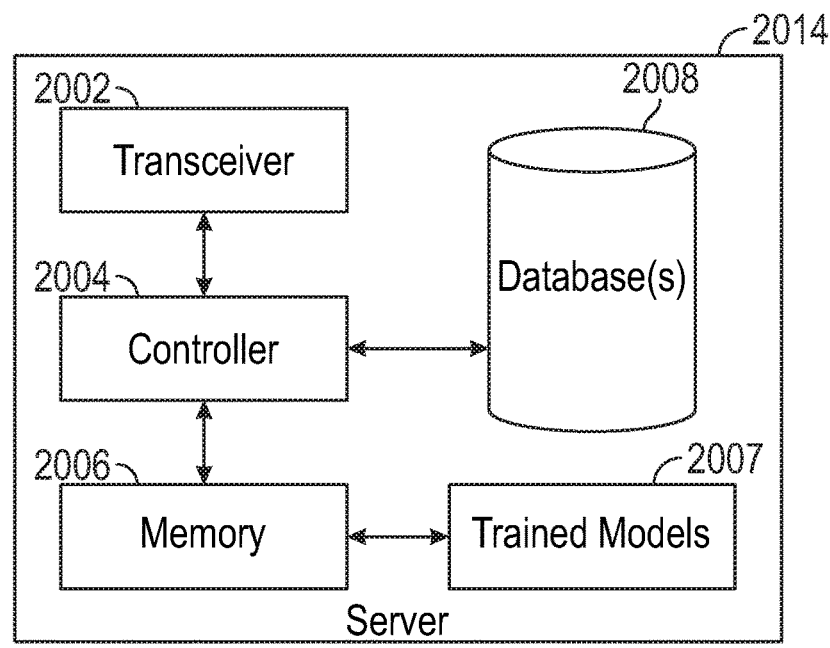
FIG. 9 is a block diagram illustrating exemplary portions of the server device.

Referring to FIG. 9, the server device 2014 includes a transceiver 2002, a controller 2004, a first memory portion 2006, a second memory portion 2007, and one or more databases stored in another memory source depicted generally by 2008.

The memory portions 2006, 2007, 2008 can be one or a combination of a variety of types of memory such as RAM, ROM, flash memory, DRAM or the like. The memory portion 2006 includes instructions for configuring the controller 2004. The second memory portion 2007 includes one or more trained models. It should be noted that the database and the trained models can be included in the memory portion 2006. They are shown separately here in order to facilitate discussion.

The databases 2008 can include, for example, baggage item identifications, baggage handler identifications, and usage attributes associated with each of the item identifications. The usage attributes can include an identification of a baggage handler that handled the baggage item, an identification of the owner of the baggage, a time duration for which the baggage item was in a certain location, etc. The database 2008 can store attributes associated with each baggage handler identification such as dispositions, deviation history, lost history, damage history, etc.

The database 2008 can be, for example, an atomic data store. The transceiver 1102 receives baggage and item data via the network from the DCE and resource requests such as, for example, http requests, via the network, from a client device. The resource request can include verification credentials such as a token issued from a certification authority and a user name and an information request for an information reply including usage parameters associated with one or more RFID chips. The transceiver 1102 sends the information reply including the usage parameters associated with the one or more RFID chips to the client device. The transceiver 1102 can be similar to the transceiver of the DCE.

The controller 2004 is configured according to the instructions in the memory 2004 to determine data in the database 2008 that is associated with the identification for each of the one or more RFID chips in the information request; generate an information reply including the usage parameters associated with the one or more RFID chips based upon the determined data; and store data in the message from the DCE in the database to be associated with the identification of the first RFID chip.

As will be discussed more fully below, the controller 2004 is further configured to store data related to a baggage item such as tracking data in the database 2008 and further to predict an outcome associated with a baggage event such as deviation probability based upon inputting attributes of the baggage event into one or more trained models 2007 such as a neural network model or self-organizing map network.

The controller 2004 and database 2008 can be configured to perform command query responsibility segregation in which commands are separated from queries to allow scaling of servers that respond to queries separately from servers delegated to responding to messages. The controller 2004 and database 2008 can further be configured to use event sourcing and/or event streaming to ensure all changes to an application state get stored as a series of events which can be not only queried but reconstructed.

It should be noted that in FIG. 1, one server was shown merely for ease of illustration. However, the server 114 may be a plurality of servers and databases connected to the network 112 via a load balancer and performing X, Y and Z axis scaling of the hardware and software.

Figure 10:
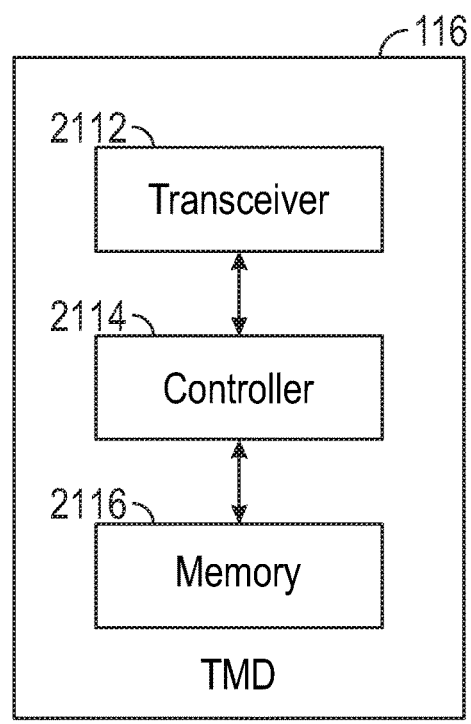
FIG. 10 is a block diagram illustrating exemplary portions of the TMD.

Referring to FIG. 10, the TMD 116 includes a transceiver 2112, a controller 2114 and memory 2116. The transceiver 2112 can be similar to the transceiver of the DCE. The transceiver 2112 receives information or resource requests such as, for example, http requests, via the network, from the client devices and other data storage sources. The resource request can include verification credentials such as a token issued from a certification authority (which must be determined to be valid and to contain the requisite claims for the resource being requested in order for the request to be successfully processed), and a user identifier and an information request for calculated quantifiable outcomes for a plurality of events. The transceiver 2112 sends an information reply to the client device. The controller 2114 is configured according to instructions in the memory 2116 to generate either solely visualization data (i.e. a json object) or graphical displays (i.e. html markup and javascript) including visualization data retrieved from server 2014 as the information reply that can then be used to generate a display on the client device. For example, the graphical display can indicate the deviation risk category or the predicted arrival time of each of a plurality of requested baggage events as discussed later.

The server 2014 and TMD 116 can be considered the backend devices of the system. The client devices of the system can be a desktop or fixed device, a mobile device, or another system (i.e. another backend server) that can run a native application or an application in a web browser. The various client devices contain a controller that executes instructions and a transceiver. The client devices can communicate with the backend system over the network 116 using a remote procedure call (RPC) or via Representational State Transfer (REST)-like or REST-ful architectural style or a messaging based architecture. The client devices communicate with the backend devices over Hypertext Transfer Protocol (HTTP), WebSockets, over another networking protocol encapsulated in Transmission Control Protocol (TCP), via message queues (for example Microsoft Message Queuing, Rabbit MQ, etc.) or any other protocols, for example, User Datagram Protocol, etc. The devices may also communicate via a cellular network (GSM, GPRS, CDMA, EV-DO, EDGE, UMTS, DECT, IS-136/TDMA, iDEN AMPS, etc.) or via other network types (i.e. Satellite phones). The data exchanged between the client devices and the backend device(s) can optionally be encrypted using Secure Sockets Layer (SSL), Transport Layer Security (TLS) and decrypted on the client device(s) and the backend device(s). The data may also be encrypted in transit using methods other than SSL/TLS (for example using a keyed-hash message authentication code in combination with a secret cryptographic key) and can be decrypted by the client or backend devices. SSL/TLS can alternatively be used in conjunction with one of the alternative encryption methodologies (belt-and-suspenders). Also, as mentioned, a client device may also consist of another third party back end system, such as another server that communicates with a database server.

Tracking Location of the Baggage Item.

Figure 4A:
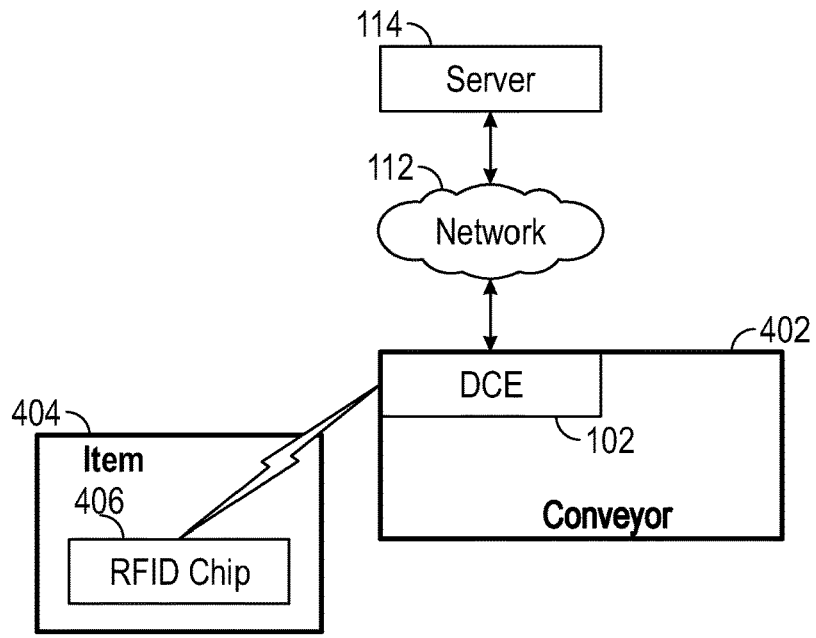
FIG. 4A-4B illustrate an exemplary operating environment in which one or more DCEs receive data from RFID chips associated with items according to a first embodiment.
Figure 4B:
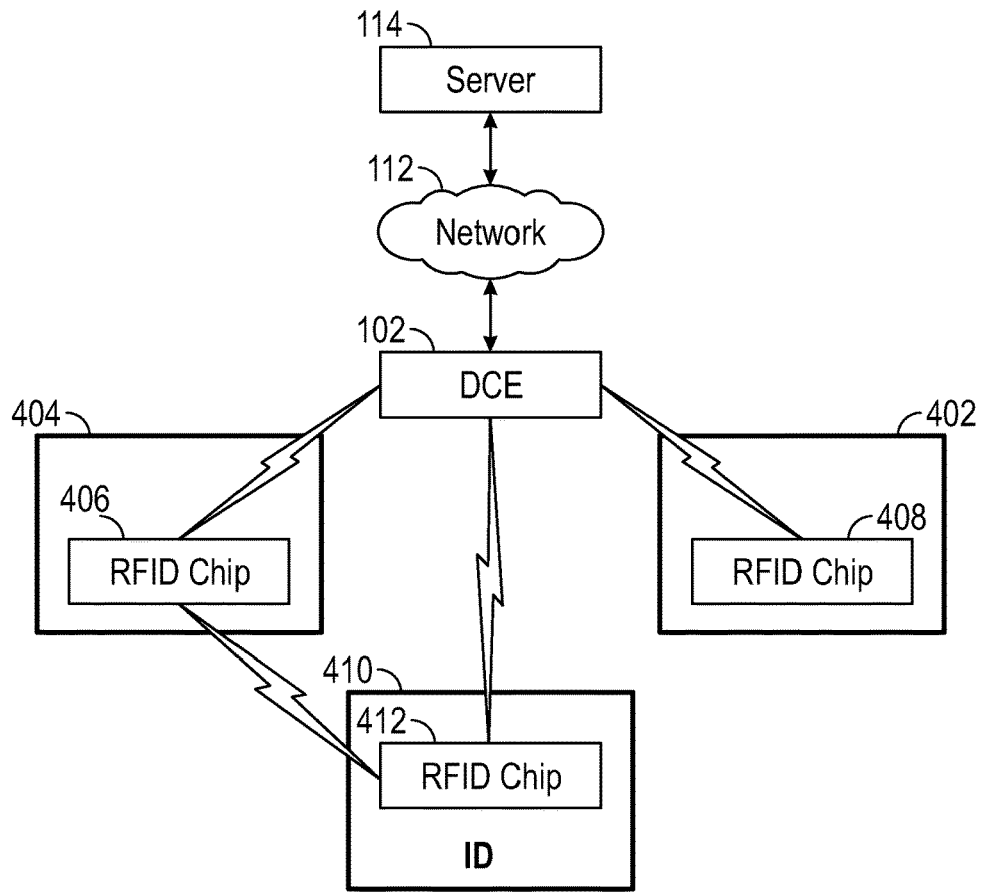

Referring to FIGS. 4A-4B, exemplary cases in which the DCE 102 receives data from one or more RFID chips and sends messages indicative of the data to the server 114 so that a baggage item can be tracked will be discussed. In the case shown in FIG. 4A, the DCE 102 is disposed on or near a conveyor device 402 (an exemplary transport device) which is part of a transport system in an airport. A baggage item 404 including a first RFID chip 406 (passive or active) is placed on the conveyor device 402. The DCE 102 establishes communication with the RFID chip 406. Particularly, the DCE 102 can periodically generate a broadcast message, and receive a registration message and data from the RFID chip 406 indicative of an event in reply to the broadcast message. Alternatively, the RFID chips can self-initiate sending of the registration message periodically or in response to another external trigger.

If the RFID chip 406 is passive type, it can send the data while receiving power from the DCE 102. The registration message can include identification information associated with the RFID chip 406. In this case, the event would be location of the baggage item 404 on conveyor device 402. The DCE 102 can send a message indicative of this event to be sent by its transceiver to the server device 114 via a connection to the network 112.

In the case shown in FIG. 4B, the DCE 102 is disposed in a position such as the ceiling beneficial for establishing wireless communication coverage for a room. The DCE 102 receives data from the first RFID chip 406 affixed to the baggage item 404, a second RFID chip 408 affixed to the conveyor device 402, and a third RFID chip 412 affixed to a baggage handler identification 410 such as a wristband or identification card. All of the chips 406, 408, 412 can be passive or active-type. The DCE 102 establishes communication with each of the RFID chips 406, 408, 412 by, for example, generating a general broadcast message, and receiving registration messages in reply to the broadcast message, and data from the RFID chips indicative of events. Particularly, the RFID chip 412 sends a message including data indicative of a first event, which would be the RFID chip 406 of the baggage item 404 being within predetermined distance from the RFID chip 412 associated with the conveyor device 402 or the baggage handler identification 410. As noted above, the RFID chip (active-type or passive-type) can include a sensor for detecting near presence of another RFID chip. The RFID chip 408 sends a message including data indicative of a second event, which would be the baggage item 404 being within predetermined distance from the RFID chip 408 associated with the conveyor device 402 for more than a predetermined time duration or the RFID chip associated with the baggage handler identification 410 for more than a predetermined time duration. The RFID chip 406 (and/or chips 412, 408) sends a message including data indicative of the chip identification. The DCE 102 can send one or more messages indicative of the events to be sent to the server device 114 via the network connection.

Referring to FIG. 5, an exemplary modification to the system will be discussed with respect to an exemplary operating environment in which a smartphone 502 communicates with the RFID chips. The smartphone 502 generates a broadcast message and receives messages indicative of events from the RFID chips 514, 516, 518 associated with items 506, 504, 508. The messages include registrations messages and data indicative of a first, second and third events in reply to the broadcast message. The smartphone 502 can then send this data to the DCE 102 directly or via the network 112 or even directly to the server 114. For example, in a large facility such as an airport, there may be areas in which there are no or very poor wireless coverage from the DCE 102. In these cases, a mobile device such as the smartphone 502 can be used to obtain data from chips in such areas and transmit the data to the DCE 102. Similar to the discussion of FIGS. 4A-4B, the events can be the RFID chips being within a predetermined distance of each other.

The smartphone 502 and/or the DCE 102 can be configured to locally persist and send the data to the server 114 either immediately upon collecting data or at a subsequent time after a batch of one or more pieces of data has been collected. The smartphone 502 and/or DCE 102 can purge the data sent from volatile or persistent memory immediately after successfully sending it or at a later time, either automatically or when prompted.

Figure 8:
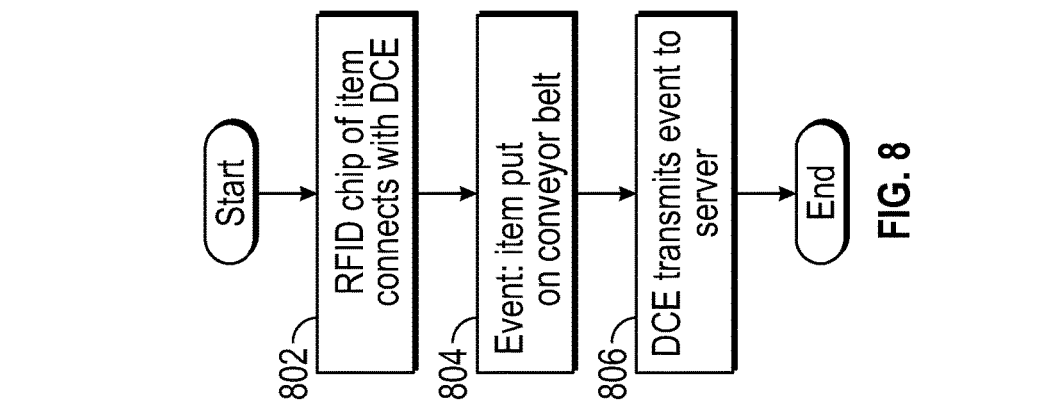
FIG. 6-8 are flow diagrams illustrating exemplary operations of the server device, DCE and RFID chips associated with baggage and identification items according to the first embodiment.
Figure 7:
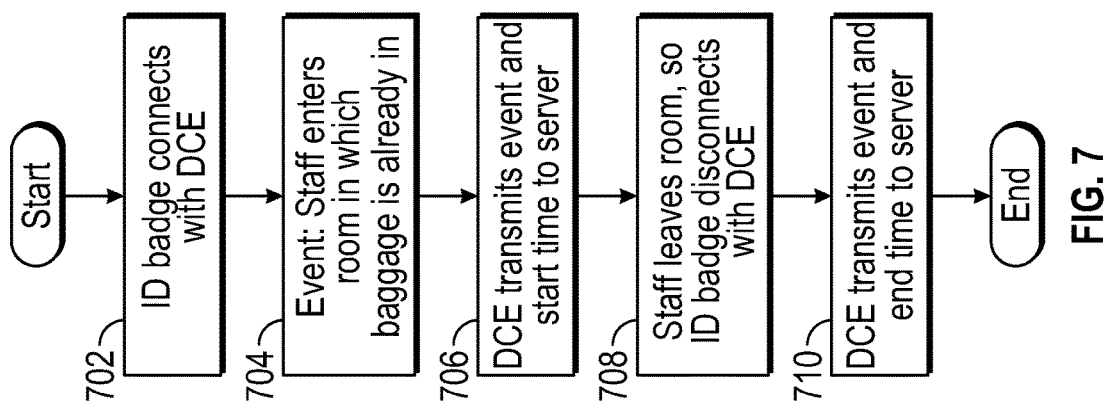
Figure 6:
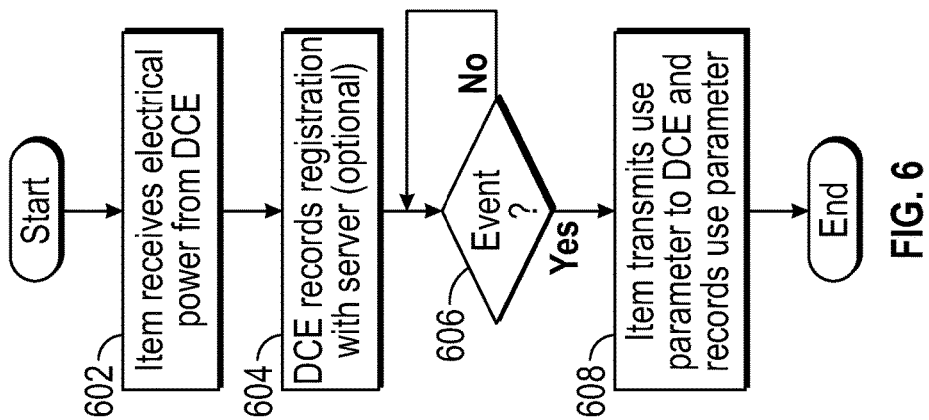

FIGS. 6-8 are flow diagrams illustrating exemplary operations of the DCE and RFID chips associated with baggage items, baggage item handlers and baggage transport devices according to the first embodiment.

Referring to FIG. 6, the operations of the RFID chip and the DCE in a simple scenario will be discussed. At 602 a passive-type RFID chip receives electrical power wirelessly from the DCE. The wireless power can be sent along with a regular general broadcast message from the DCE or an interrogation request. Of course, if the RFID chip is active-type, this step can be omitted. At 604, the RFID chip sends registration information to the DCE, which records it in its memory. Particularly, the registration information can include the identification of the RFID chip. At 606, if the RFID chip and/or the DCE determines that an event has occurred, at 608 the RFID chip sends use parameters associated with the event to the DCE. The DCE records the usage parameters in its own memory or immediately transmits the information to the server to be stored in the database. The event can be, for example, detecting that the RFID chip is within predetermined distance from another RFID chip associated with, for example, the conveyor device or a baggage handler for more than a predetermined time duration as discussed in FIGS. 4A-4B or merely the RFID chip receiving power from the DCE. Although not shown, the DCE can send messages indicative of this data to the server device.

Referring to FIG. 7, the operations of the RFID chip and the DCE in a more complex scenario in which a baggage handler handles the baggage item will be discussed. At 702, the baggage handler wearing an identification such as a badge including an RFID chip (active or passive-type) enters a room within the communication area of the DCE and the RFID chip registers with the DCE. The baggage item which includes another RFID chip already registered with the DCE is already in the room. At 704, the DCE records a first baggage event indicative of the baggage item and the baggage handler being in the same room and the start time. At 706, the DCE generates a message representative of this first event to be transmitted to the server. At 708, the baggage handler (staff) wearing the identification including the RFID chip leaves the room and disconnects from the DCE. At 710, the DCE records the time the RFID chips disconnects as the end time of the first event and generates a message representative of the end time of the first event to be transmitted to the server. Alternatively, or in addition to, in this scenario the event can be the RFID chip of the baggage handler identification and the RFID chip of the baggage item being within a predetermined distance of each other (NFC established).

Referring to FIG. 8, the operations of the RFID chip and the DCE in the scenario shown in FIG. 4A will be discussed. At 802, the RFID chip associated with the baggage item connects with the DCE associated with the conveyor device. At 804, the DCE records an event indicative of the baggage item being on or near the conveyor device. At 806, the DCE generates a message representative of this event to be transmitted to the server.

Referring to FIG. 14, an exemplary conceptual message 920 generated by the DCE 120 (shown in human readable format) to be sent to the server is shown. The message 920 includes the series of events related to the baggage item discussed above. The time data can be determined by when the message from the RFID chip was received by the DCE or when it was sent to the server or may be included in the message from the RFID chip. The location data can be generally the location of the DCE 120 and/or the RFID chip. The server device can store the data included in the message 920 in the database in the format depicted by 940. Particularly, information parameters can be stored according to an identification reference mapped to a given baggage item identity and/or any other entity identity referenced in a given message containing situational data. Examples of such entity identity references include the actual product type or unique product identity associated with a given RFID chip identity, any baggage handler (RFID chip identity associated with a baggage handler) that may have been registered in proximity to an RFID chip with an identity that references a given item, any baggage item (RFID chip identity associated with a baggage item) that may have been registered in proximity to an RFID chip with an identity that references a given item, a room or transport device such as a conveyor belt referenced by a given DCE identity or RFID chip identity, etc.

The RFID chips can detect separation from another RFID chip or being within a predetermined distance from another RFID chip by the sensor group. Alternatively, the detection can be performed by ambient radio frequency communication techniques which can detect proximity up to, for example, 70 cm by backscattering. Further, the detection can be performed at the DCE end by, for example, measuring the RSS of the RF signal received from the chips.

Figure 11:
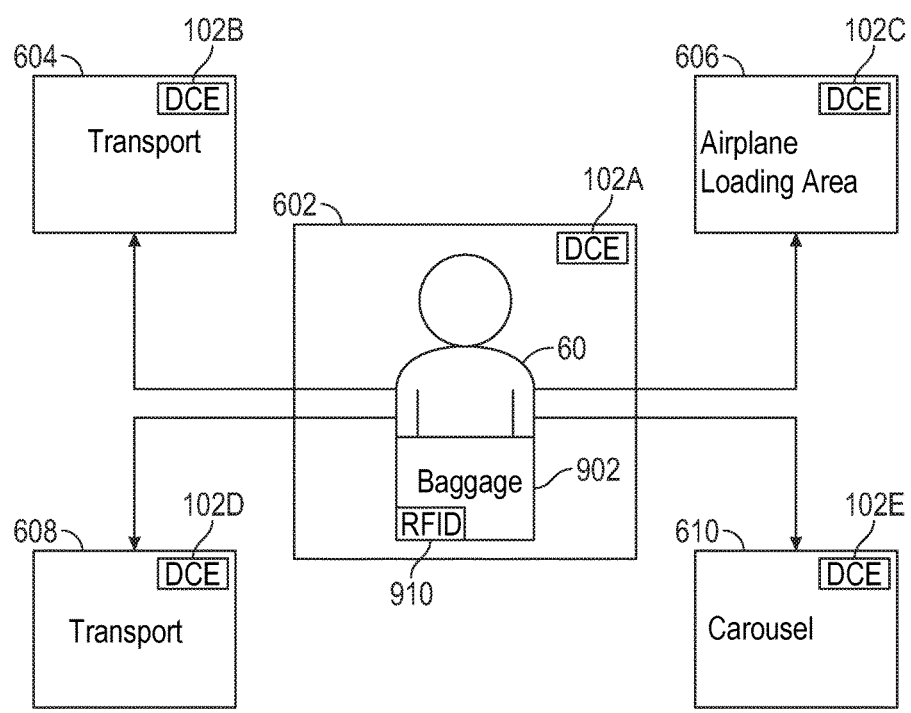
FIG. 11 illustrates exemplary baggage events.
Figure 12:
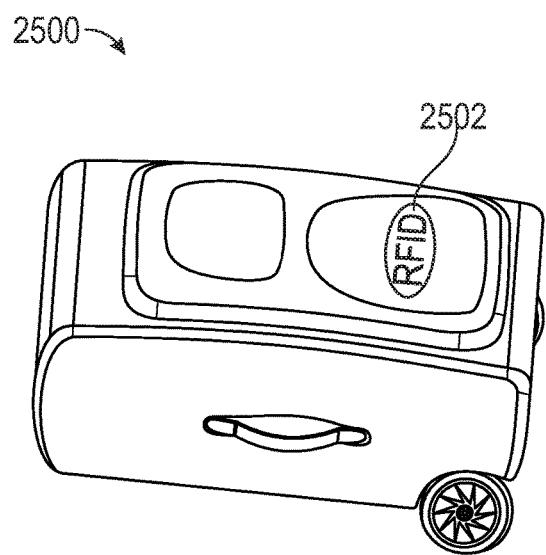
FIG. 12 is an illustration of a baggage item including an RFID tag.

Referring to FIG. 11, exemplary cases of events in which the baggage system (namely server, DCE and RFID tag) passively captures baggage data will be discussed. The DCEs 102A, 102B, 102C, 102D are disposed in a position such as the ceiling beneficial for establishing wireless communication coverage for the respective room. Each of the DCEs receives data from the RFID tag 910 affixed to a baggage item 902 and the RFID tag affixed to a baggage handler identification badge (not shown) of a baggage handler 60. The DCE establishes communication with the RFID tag 910 by, for example, generating a general broadcast message, and receiving a registration message including data from the RFID tag 910 in reply to the broadcast message. Alternatively, the RFID tag 910 can self-initiate sending of the registration message periodically or in response to another external trigger.

Each of the DCEs 102A, 102B, 102C, 102D can store a unique identification associated with its physical location (referenced to the location, for example in a database such as 2008 where the DCE IDs and locations are stored) or store a physical location when it is put into service. The identification of the DCE and/or the location information from the DCE is sent in its communications with the server and thus the TMD. Accordingly, the TMD can determine the location information for the baggage item associated with RFID tag.

The baggage item 902 is in a first room such as a check-in counter or baggage sorting area 602. The DCE 102A in the room 602 receives the identification of the baggage item 902 from its RFID tag 910 and the identification of a baggage handler 60 from, for example, an RFID tag associated with and identification badge of the handler 60.

In a first exemplary event, the baggage item 902 is moved from room 602 to a transport room 604 such as a conveyor device room. The RFID tag 910 sends a message including the baggage item identification from the RFID tag 910 of the baggage item 902 in response to the broadcast message from the DCE 1028.

In a second exemplary event, the baggage item 902 is moved from room 602 to an airplane loading area 606. The RFID tag 910 sends a message including the baggage item identification from the RFID tag 910 of the baggage item 902 in response to the broadcast message from the DCE 102C.

In a third exemplary event, the baggage item 902 is moved from room 602 to a transport area 608 such as a transport vehicle loading area. The RFID tag 910 sends a message including the identification from the RFID tag 910 in response to the broadcast message from the DCE 102D.

In each of the above three exemplary events, an identification of the baggage handler 60 can send identification information to the DCE 102 also in response to the broadcast message from the DCE.

In a fourth exemplary event, the baggage item 902 is moved from room 602 to the carousel 610 for pick-up. The RFID tag 910 sends a message including the identification from the RFID tag 910 of the baggage item 902 in response to the broadcast message from the DCE 102E. In each of the four exemplary events, the respective DCE sends location information to the server. Alternatively, location information could come from the RFID tag rather than the DCE.

Figure 13:
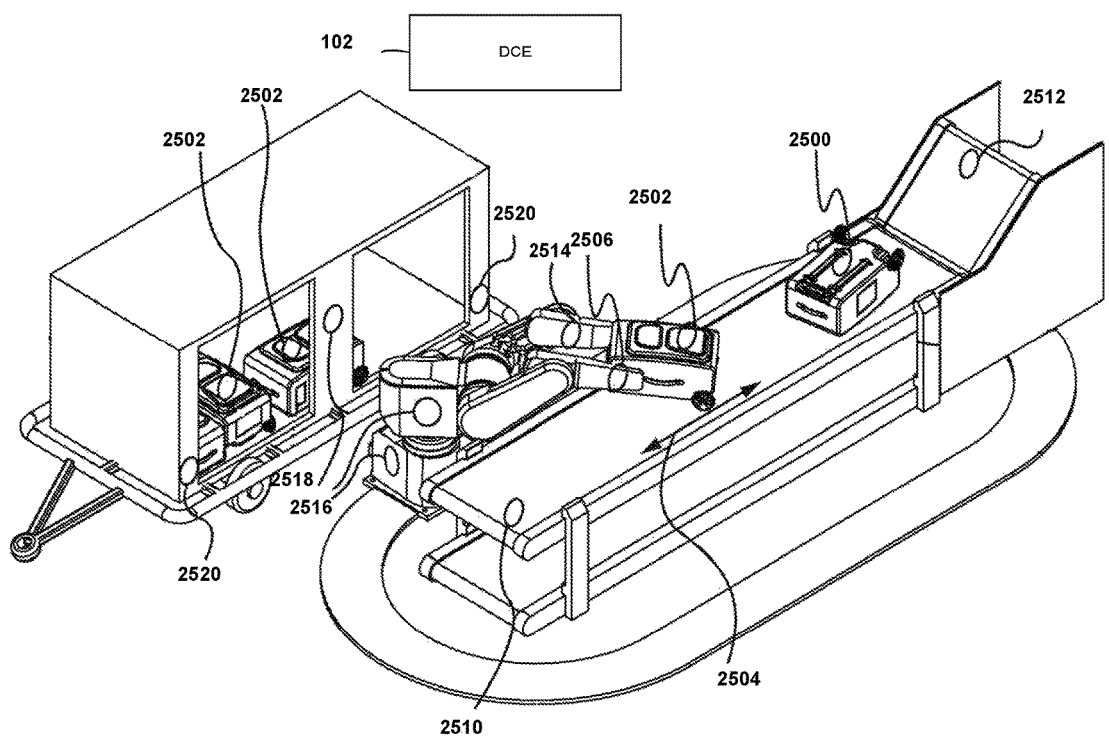
FIG. 13 is an illustration of baggage items transported on a conveyor device and transferred from the conveyor device to a transport vehicle by a robot arm.

In each of the four examples, the respective DCE will send the information received from the RFID tag 910 to the server 2014 via the connection to the network 112. As depicted in FIG. 13, each of the baggage items 2500, which includes an RFID tag 2502, can be transferred between rooms by a conveyor device 2504 and a robot arm 2506 that transfers the baggage item 2500 from the conveyor belt 2504 and loads it into a transport vehicle 2508. The conveyor device 2504 can include a plurality of RFID tags 2510, 2512, but includes at least one RFID tag. The robot arm 2506 can include a plurality of RFID tags 2514, 2516, but at least one RFID tag. The transport vehicle 2508 can also include a plurality of RFID tags 2518, 2520, but at least one RFID tag. The area shown in FIG. 13 will include a DCE 102 which can be fixed to the ceiling or the conveyor device 2504. Alternatively, the DCE can be a mobile device such as a smartphone 502 as shown in FIG. 5 or even a drone device. At least one of the RFID tags on the conveyor belt 2504, robot arm 2506 and transport device 2508 can, for example, be an active-type RFID tag for powering a passive-type RFID tag on the baggage item.

Although not shown in FIG. 13, baggage handler(s) 60 who have their own identifications with an RFID tag communicate with the DCE. Therefore, the server 2014 can collect data regarding the baggage handler that is transferring the baggage item.

Only four examples of events were shown in FIG. 11. Of course, numerous other types of baggage events can be implemented such as baggage loaded on airplane, transfer between transport devices, etc. Further, for simplicity the transition was from room 602 to one of the other four areas. However, in practice the transition sequence will be between any of the rooms and will include different locations not shown.

Returning to FIG. 5, a mobile device such as smartphone 502 can serve as a proxy for identification of an individual rather than an RFID tag being on an identification. For example, the smartphone 502 can be configured to communicate with the server 114 and include NFC capability to communicate with RFID tags on, for example, a baggage claim slip and the baggage item. When the baggage item arrives at a carousel, the RFID tag on the baggage item is interrogated by a DCE 102 in the area. Further, when the RFID tags of the baggage item and the baggage claim slip are in close proximity to each other, a pairing signal can be sent to the DCE 102 and thus to the server 114. The pairing signal can be generated by the RID tags when receiving power from the DCE 102 or the smartphone 502. The pairing signal can be included in the event or registration messages as discussed above. Accordingly, the system can confirm that the designated owner (who has the baggage claim slip) is the person who retrieved the baggage item.

Creating a Trained Neural Network Model to Predict an Outcome

Figure 16:
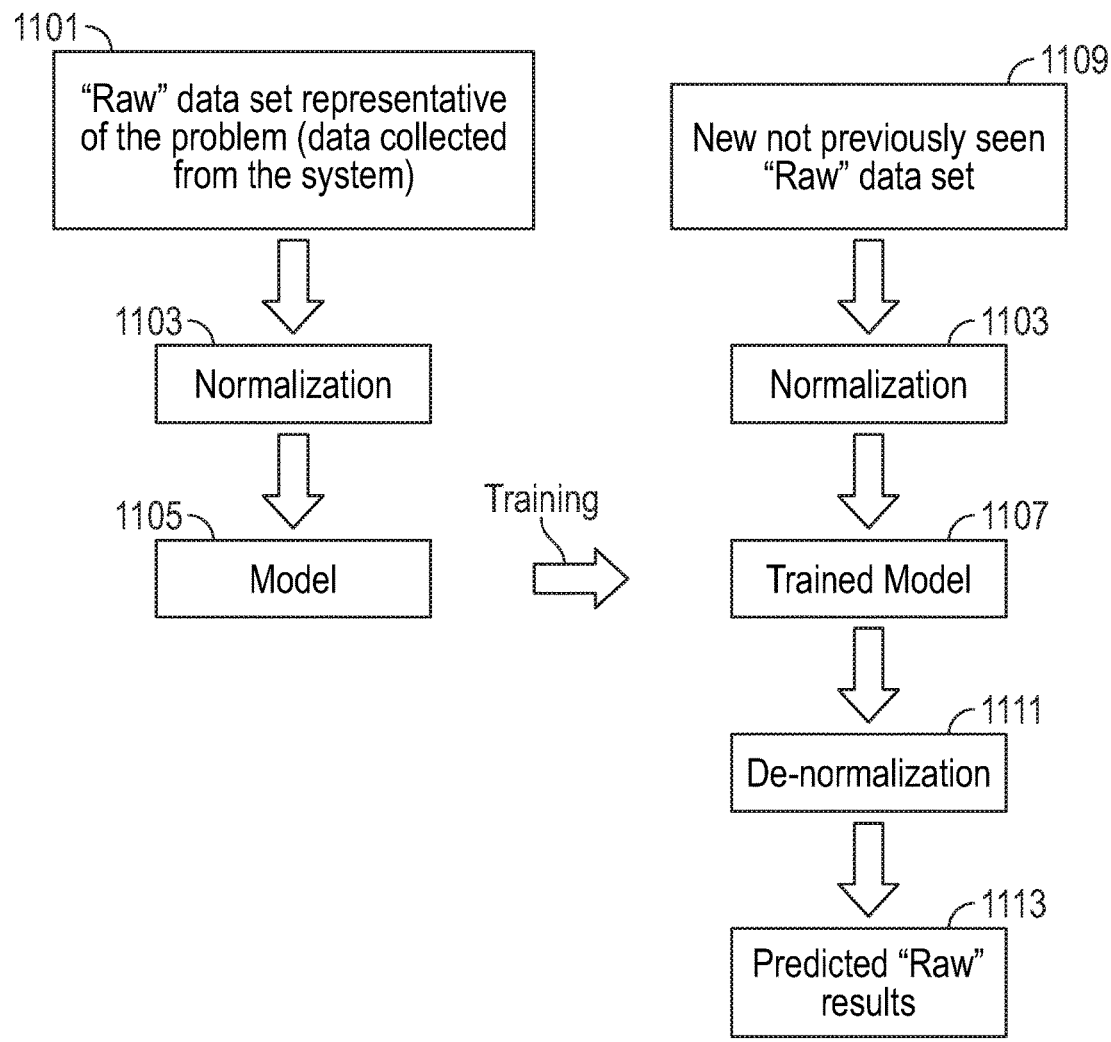
FIG. 16 is a block diagram illustrating high level operations for creating a trained neural network model (NNM) according to an embodiment.

Returning to FIG. 9, the server device 2014 stores one or more trained models 2007 which are used to predict an outcome of an event such as whether a baggage item is or is likely to be deviated (lost), stolen, etc. (baggage event). A representation of the process for creating, training and using the trained model is shown in FIG. 16. Raw data 1101 is normalized 1103, and then input into the model 1105. The model 1105 is trained to form the trained model 1107. New data 1109 is normalized 1103 and input into the trained model 1107. The output data of the trained model 1107 is de-normalized 1111 to obtain the output data (predicted raw results) 1113. As shown in FIG. 17, the raw data 1101 and new data 1109 include sets of data [1, 2 . . . N] with known outcomes and properties of each of the data. For example, the data can be past baggage events with known deviation outcomes. The properties of the data can be attributes of the baggage, airport facilities, baggage handlers, etc.

The model 1105 is trained by an iterative machine learning algorithm. After initial deployment, the server 2014 will also continuously collect data from a variety of sources along with actual related baggage system operational outcomes; this data can subsequently be used as training data. As such, the TMD/server is able to continuously learn and improve its ability to predict the outcomes of interest. In addition, the knowledge of the system can continue to evolve in the event the system dynamics change. Take, for example, the time between when a baggage item is checked in at a departure airport counter and the time of the baggage item's arrival at the carousel of the destination airport. There is a relationship between the multitude of attribute data the system collects and the outcome in question. Exemplary attributes the server 2014 collects about a baggage that can be used: the baggage type, the baggage size and/or weight, the baggage color, the baggage arrival time, the arrival airport, the departure, destination and intermediate airports, the identities of the of the baggage handlers who handled the baggage item, to provide several examples. However, there is no one specific mathematical relationship or equation that describes the relationship between these exemplary attributes of the baggage item and the outcome of interest. However, because of the server's machine learning capabilities, it has the ability to "learn" or be trained from pre-existing data and from the data it collects prospectively. Said another way, the server 114 "learns" from experience.

Data Set Encoding, Normalization and De-Normalization

Neural network models only use numerical values for training and processing. Thus, any nominal categorical data fields that are a part of raw data that will ultimately be used by models in the system are first encoded to numerical values and "raw" numerical data in many cases by a pre-processing such as normalization 1103 before training and processing. While normalization and de-normalization steps may not be explicitly described as being carried out before or after data consumption by any given model, this should not be misconstrued and lead to the assumption that these routine steps are not carried out.

The normalization processes 1103 and corresponding de-normalization processes 1111 are used not only for training data sets, but also for new, unseen data that is fed into the trained models. Though it is not the rule, frequently, the output from the trained models is normalized and in the event it is a categorical data field the output will also be encoded. Thus, often output from the system models has to be de-normalized and possibly decoded to yield the "raw data," "human readable" format of the predicted output.

Neural network training is often more efficient when independent numeric data (x-data) is normalized. For this reason, the system most often normalizes numeric data along the same scale being utilized by the model for all data fields, including nominal data fields. The scale the system utilizes for normalization depends on the particular activation function employed by a given model. In most cases this results in normalization either from −1 to 1 or 0 to 1, however, in some cases intermediate range values may be used as well, such as −0.5 to 0.5, for example. This "raw data" normalization step also prevents predictors or inputs that are relatively larger in magnitude (as compared to other predictors or inputs) from having more relative influence on the change in the value of synaptic weights during training of the system models. For problems with normalized nominal data, one neuron is required to represent each numeric data field type.

Figure 18A:
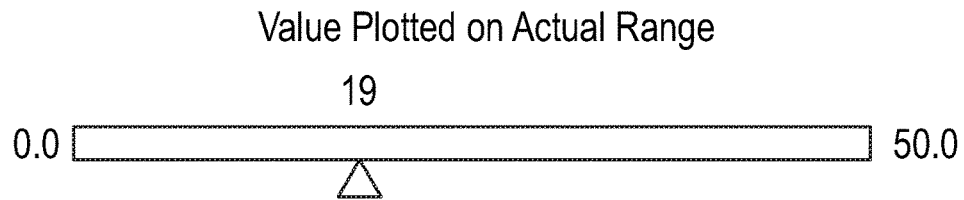
FIGS. 18A-18B are illustrations of various exemplary approaches for normalizing the data set.

An example of one of the independent predictors (input x-data) or input attributes that can be utilized by the system is the number of baggage handlers who handle the baggage or conveyor belts a baggage item travel on (referred to here as "transitions") in the departure airport. Suppose a baggage item has 19 transitions and that this "raw data" value needs to be normalized to a −1 to 1 normalization range. If the actual range of the possible number of transitions is 0 to 50, for example, then to normalize this input x-data, the system's continuous or numeric normalization process would carry out normalization calculations similar to those illustrated herein. Initially, the value can be plotted on an actual range as shown in FIG. 18A. Then a normalization calculation can be carried out as shown below:

$$\{[(19-0.0)*(1.0-(-1.0))]/(50.0-0.0)\}+(-1.0)=-0.24$$

Figure 18B:
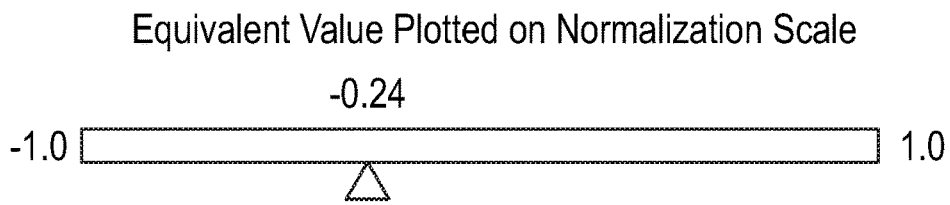

Referring to FIG. 18B, equivalent value plotted on a normalization scale is shown.

Figure 19A:
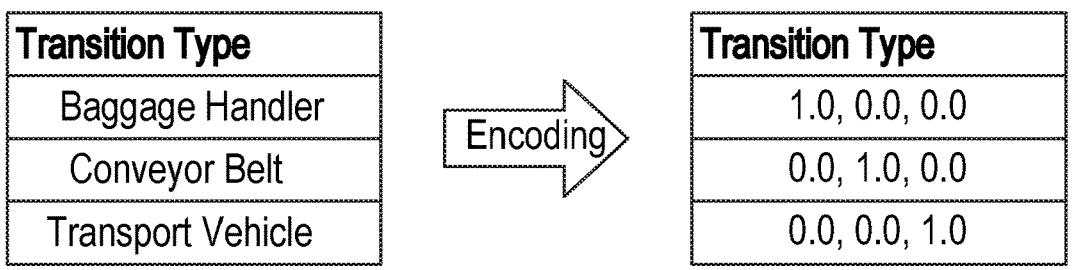
FIG. 19A-19B are illustrations of various exemplary approaches for encoding the normalized data set.

In the encoding process, the system may encode classification labels into double values within the normalization range such as −1 to 1 or 0 to 1. The scale the system utilizes for encoding depends on the particular activation function employed by a given model. An approach the system employs at times to encode nominal data fields is so called one-of-N encoding as shown in FIG. 19A. For example, one of the attributes that may be used is the transition type. In this case the airport has three transition types: baggage handlers, conveyor belts and transport vehicles. The nominal categories are represented by double values within a normalization range of 0 to 1. Another variety of this approach that can be used is one-of-C-dummy encoding. When this method is employed, the number of neurons needed to represent a given number of nominal data field types is equal to the number of distinct nominal categories. However, one-of-N encoding is subject to an unequal distribution of error (unequal fault behavior) for wrong predictions which can occur when there are more than two nominal categories. For example, if the value predicted by a given model is a first transition type {0.0, 0.0, 1.0} but the ideal (real) value is actually a second different transition type {0.0, 1.0, 0.0}, it is apparent that there is only error in two parts. Said another way, if the predicted and the ideal (real) values are compared, the first value is 0.0 in both (i.e. is correct), while the other two values are both wrong. This is unequal distribution of errors.

Figure 19B:
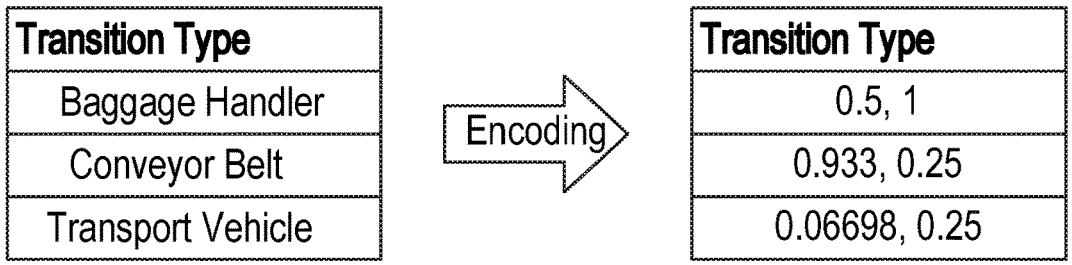

Due to this shortcoming of one-of-N encoding, particularly in instances when there are more than two nominal categories, the server can employ equilateral encoding (one-of-(N-1) encoding shown in FIG. 19B or one-of-(C-1) dummy encoding for encoding nominal categorical data. When equilateral encoding is used, fault behavior is equally distributed when wrong predictions are encountered. The equilateral encoding used by the system is based on the Euclidean normalization technique which results in each nominal category having equal Euclidean distances from the others. The Euclidean Distance is calculated as shown below:

$$\text{distance} = \sqrt{\frac{(i_1 - a_1)^2 + (i_2 - a_2)^2 + \ldots + (i_n - a_n)^2}{n}}$$

Where the variables represent the following:
=ideal (real) output value
a=actual (predicted) output value
n=number of sets of ideal and actual values With equilateral encoding, all classes are able to be represented by a number of doubles equal to one minus the total number of nominal data classes, in this case 2 (3−1=2). When this technique is used, every set of possible ideal and actual combinations in the above example will result in an equivalent Euclidean distance.

Ideal: {0.5, 1} Actual: {0.933, 0.25}
Euclidean Distance:
=$((0.5-0.933)^2+(1.0-0.25)^2)^{1/2}$
=$(-0.433^2+0.75^2)^{1/2}$
=$(0.187489+0.5625)^{1/2}$
=$(0.749989)^{1/2}$
=0.8660

Ideal: {0.06698, 0.25}
Actual: {0.5, 1}
Euclidean Distance:
=$((0.06698-0.5)^2+(0.25-1)^2)^{1/2}$
=$(-0.43302^2+(-0.75^2))^{1/2}$
=$(0.1875063204+0.5625)^{1/2}$
=$(0.7500063204)^{1/2}$
=0.8660

Equilateral encoding is not employed by the system in scenarios where there are less than three distinct nominal categories.

Exemplary embodiments of a supervised and unsupervised neural network training algorithm used to create a trained model will be discussed. However, these embodiments are merely examples. Those skilled in the art know any variety of machine learning algorithm approaches can be used for the purpose of training system models including, but not limited to support vector machines, genetic programming, Bayesian statistics, decision trees, case based reasoning, information fuzzy networks, clustering, hidden Markov models, particle swarm optimization, simulated annealing, among others. While the exemplary embodiments herein do not detail every machine learning approach employed by the system to solve the technical problem, this should not be construed as an omission of these capabilities or approaches which the system can and in some cases does leverage to solve the technical problem.

There are three primary categories of machine learning tasks: classification, regression and clustering tasks.

Classification

Figure 34A:
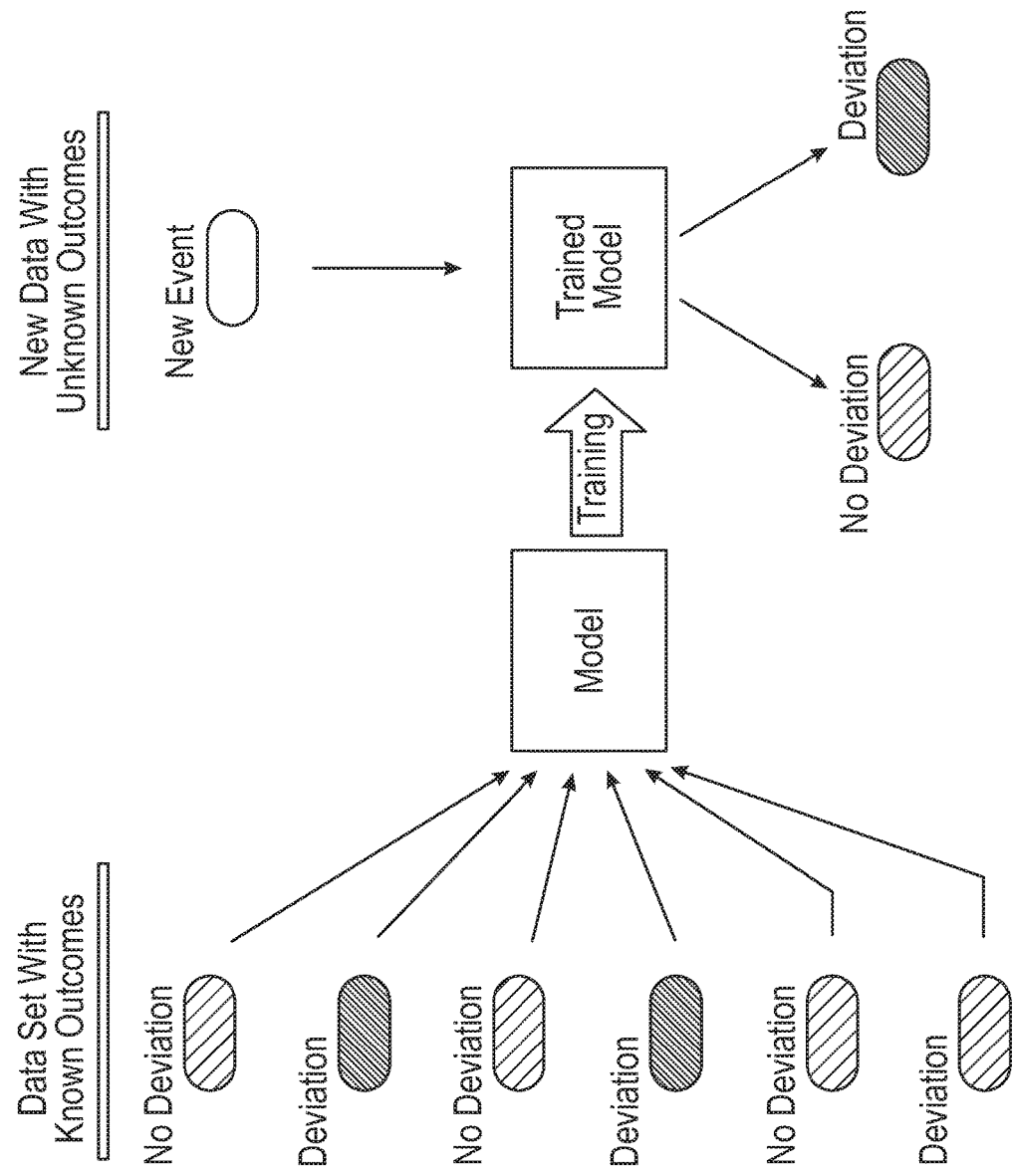
FIGS. 34A-34B are illustrations of a case in which the model is used to categorize the deviation risk of a plurality of baggage events.
Figure 34B:
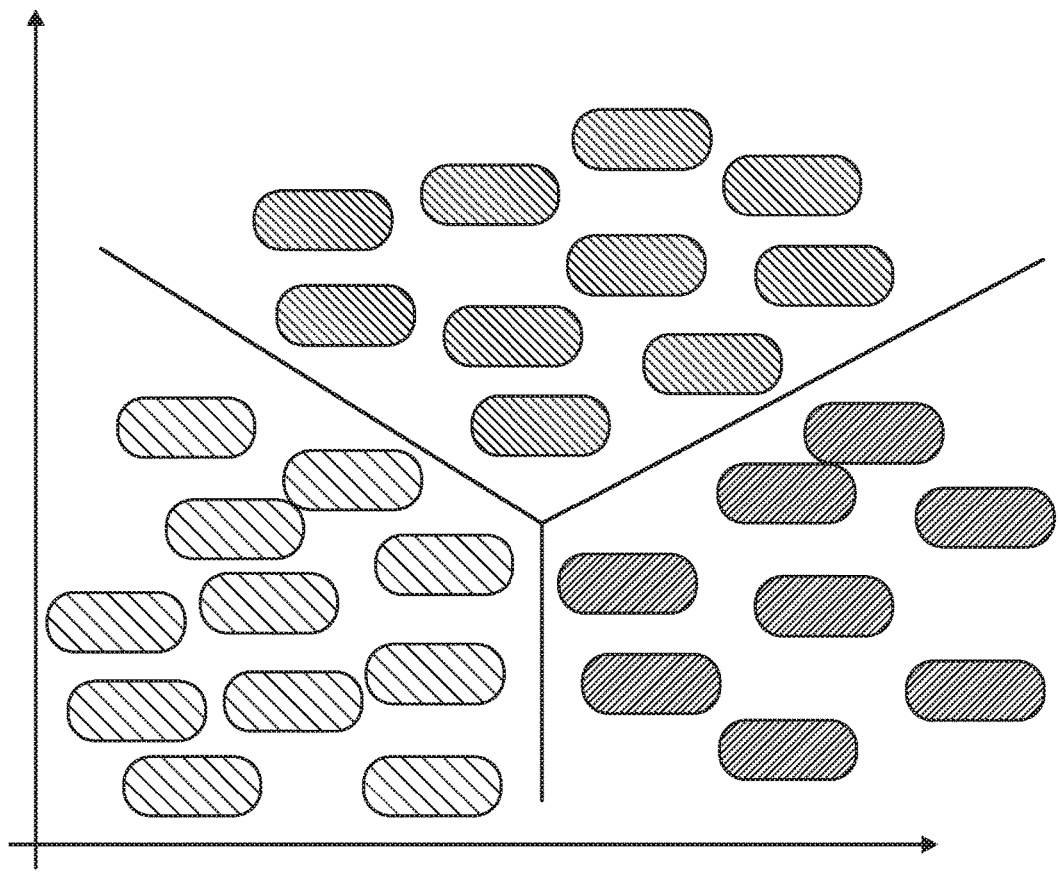

Referring to FIG. 34A-34B, a classification task for predicting deviation risks of a baggage item is shown. The machine learning task entails a two-step supervised learning process which utilizes both input and output data in the model training process. Model construction is done using a representative training data set and the model, once trained is used for classifying new or unseen cases, for example a baggage item at risk of deviation—predicts nominal categorical assessment or assignment. The inputs are collected baggage item data attributes/properties. The output will be predicted categorical risk for deviation, no deviation, moderately deviated and severely deviated. As shown in FIG. 34B, like events can be clustered together to reveal non-obvious related deviations (or causes thereof) such as, for example, a similar cause (a particular strap, or traversing a particular path, all on a particular shift, or all at a particular gate at airport Y, or some other characteristic).

Regression

Figure 35:
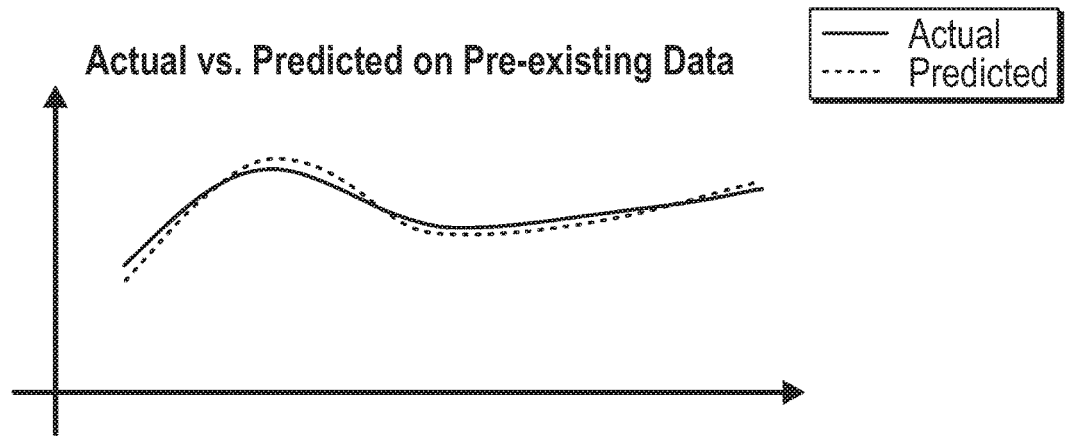
FIG. 35 is an illustration of exemplary regression tasks performed by the TMD.
Figure 35:
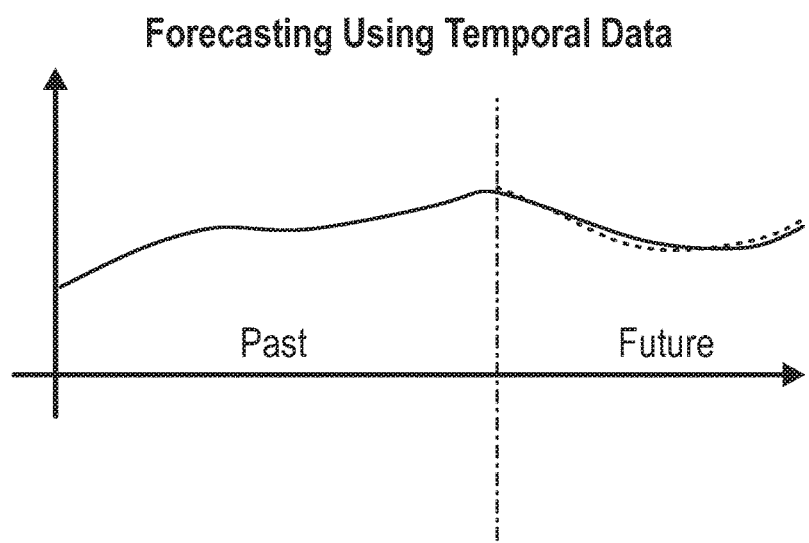

Referring to FIG. 35, a regression task entails a two-step supervised learning process which utilizes both input and output data in the model training process. Model construction is done using a representative training data set and the model once trained, is used to predict the output (numerical or continuous data) for new or unseen cases. The output can be, for example the anticipated length or duration of deviation (a quantity of time).

Clustering

Clustering tasks carried out in the server entail an unsupervised learning process. For clustering tasks, categories and outcomes are not known, or if known are not used for model training. Models are trained from the inputs of the data set, again without or ignoring the corresponding outputs, and from these the model training algorithm tries to identify similarities among the input data and cluster the data based on these learnings, so called "unsupervised learning." The backend devices employ each of these categories of machine learning tasks.

Unsupervised Learning

The server 2014 in some instances utilizes unsupervised learning techniques (for example Self-Organizing Map (SOM)—also known as Kohenen Map, Singular Value Decomposition (SVD), and Principal Component Analysis (PCA)) for the purpose of dimensionality reduction. This is done to reduce the input data sets from a large number of dimensions to a lower number of dimensions, such as, for example, to two or three dimensions. This is often employed as a pre-processing step in advance of the application of supervised learning methods. By leveraging unsupervised learning for the purpose of dimensionality reduction, the system is able to reduce the processing (training) time and improve model accuracy. Some supervised machine learning techniques work very well on data sets with a low number of dimensions, however, when there are a very large number of dimensions, performance can degrade, the so called "curse of dimensionality." Thus, the employment of dimensionality reduction techniques actually boost model performance and efficiency for some tasks.

Another exemplary task, for which the server 2014 uses unsupervised learning, as detailed further later herein, is data visualization. Humans are quite facile with the visualization of data in two or three-dimensional space, however visualizing data with more than three dimensions is not a task for which humans are well suited. One of the ways the system overcomes this is by using its unsupervised learning dimensionality reduction capabilities to make patterns in n-dimensional data more easily perceptible to human end users. Thus, the server's dimensionality reduction techniques significantly boost its ability to make data actionable by making the visibility of meaningful, yet complex patterns, more perceptible to its human end users.

Supervised Learning

The backend devices can use supervised machine learning techniques.

Figure 20:
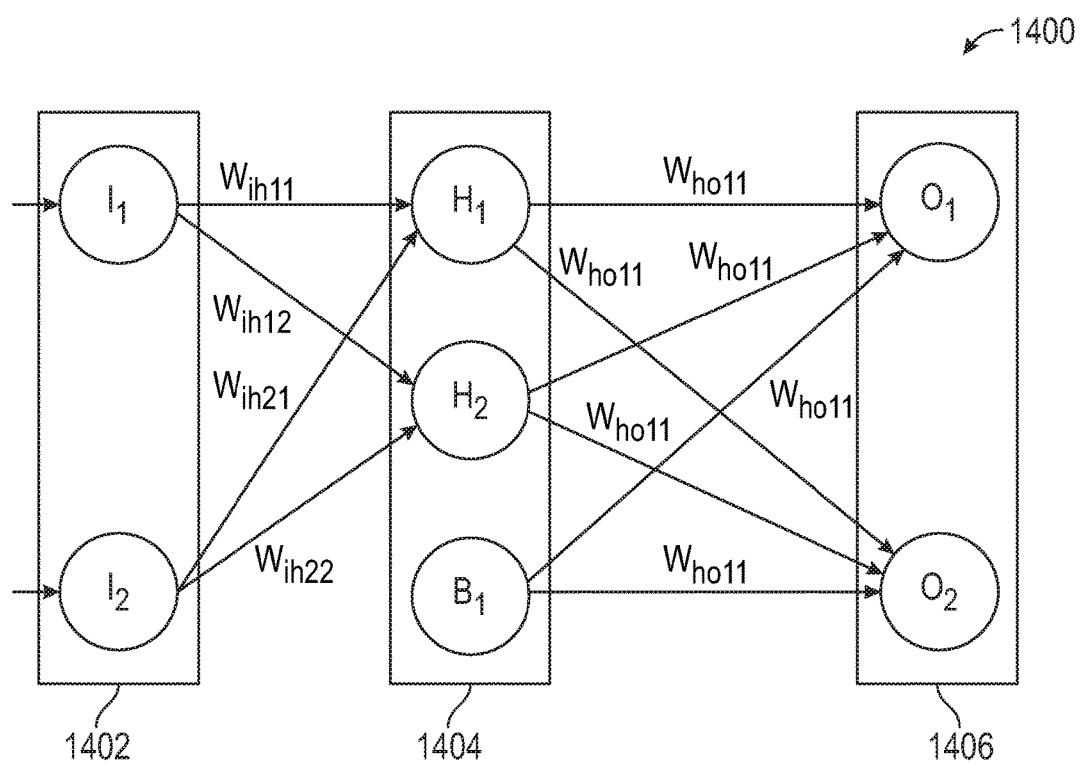
FIG. 20 is an illustration of an exemplary simple feed forward NNM.

Referring to FIG. 20, the backend devices can use a neural network model (NNM) 1400. The NNM 1400 includes an input layer 1401, a hidden layer 1404 and an output layer 1406. The input layer 1401 includes input neurons ($I_1$ and $I_2$) which provide input signals to the network without any processing units (processing units, described further herein are comprised of summation and activation functions). The hidden layer 1404 includes hidden neurons ($H_1$ and $H_2$)

which provide a means to converge the network's solution leveraging additional processing units (summation and activation functions). At times, if these neurons are not present, the neural network may not be able to output the desired result. The hidden layer 1404 can also include bias neurons (B₁) to provide bias values if there is a requirement for non-zero results. Essentially, they provide a way to obtain a non-zero result even if the input is zero. These most typically do not have any incoming connections, but rather instead, their input values are fixed, for example being fixed with a value of one (1). The output layer 1406 includes output neurons ($O_1$ and $O_2$) containing processing units (summation and activation functions) which provide the means for obtaining the final output of the neural network. A typical neural network employed by the system is comprised of one input layer, one output layer and a plurality of hidden layers (zero or more). The number of neurons the system employs in its neural network input and output layers varies.

In the neural network, connections between neurons have a connection weight or synaptic weight, for example the connection between $H_1$ and $H_2$ has a synaptic weight of $w_{ih\ 12}$. The $w_{ih\ 12}$ notation means the synaptic weight of the connection from input neuron $I_1$ and hidden neuron $H_2$. This synaptic weight denotes the strength of the connection, the higher the weight the higher the strength and vice versa. This synaptic weight determines the effect the synapse has on processing. The synaptic weight is also directional. Said another way, this means the connection from $I_1$ to $H_2$ is different from that from $H_2$ to $I_1$. Thus, the notation $w_{ih\ 12}$ not only denotes the neurons that are connected or involved but also the direction of the connection.

Figure 21:
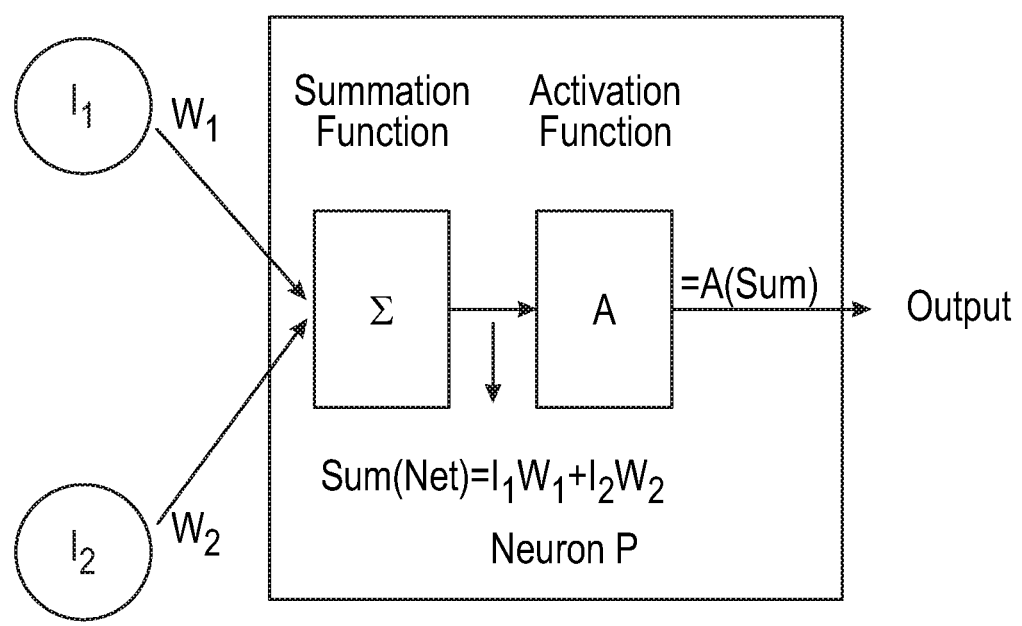
FIG. 21 is an illustration of an exemplary neuron of the NNM.

As shown in FIG. 21, a neural network neuron includes the summation function and activation function. The summation function sums input signals based on their signal strength, or weights. The sum value is also known as Net. The output of the summation function is the weighted sum of input signals. The activation function of a neuron takes the weighted sum of the input signals and performs some calculations to arrive at the output value. Some examples of activation functions used by the system include:

The sigmoid function $$f(x) = \frac{1}{1+e^{-x}}$$

Figure 22A:
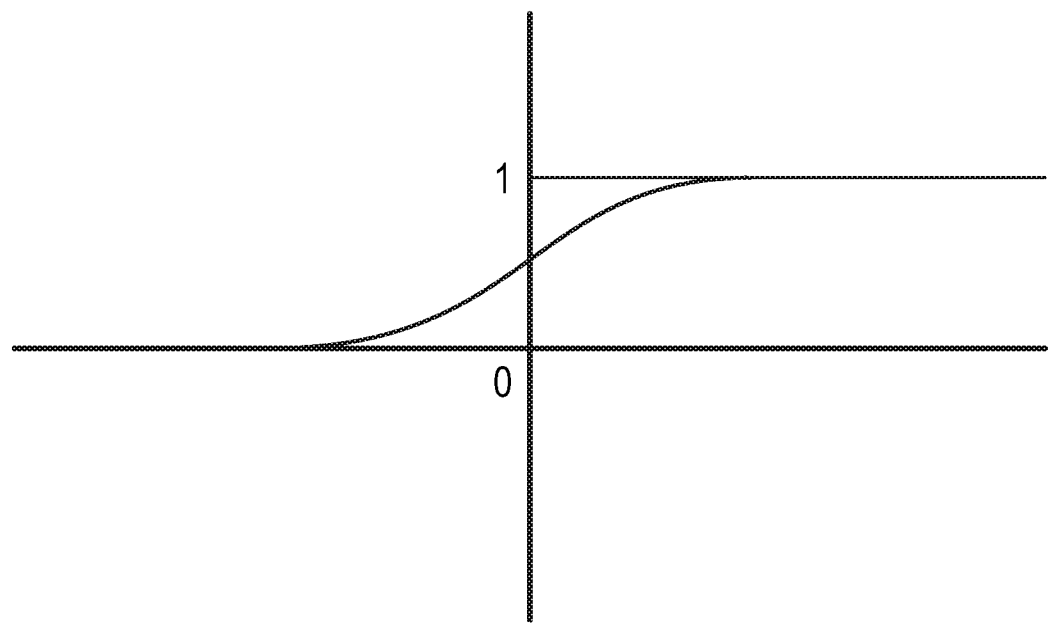
FIGS. 22A-22C are illustrations of exemplary activation functions for the neurons of the NNM.

As shown in FIG. 22A, a characteristic of the sigmoid function is that for all values on the x axis, the function output value (y axis) will lie between 0 and 1. The sigmoid function is used in instances where only positive outputs are expected.

The hyperbolic tangent function $$f(x) = \frac{e^{2x}-1}{e^{2x}+1}$$

Figure 22B:
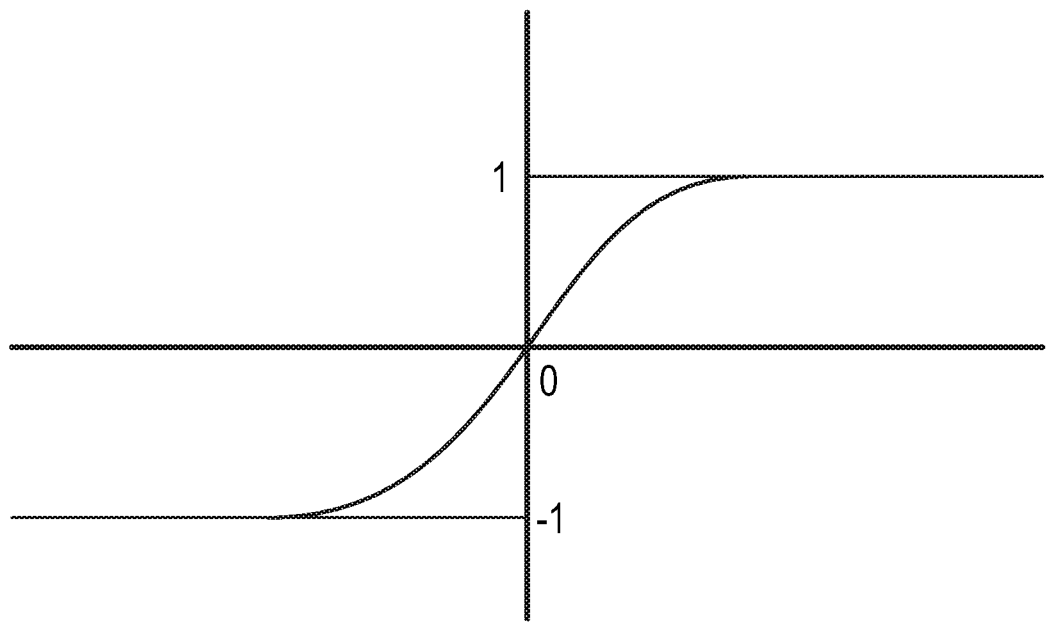

As shown in FIG. 22B, a characteristic of the hyperbolic tangent function is that for all values on the x axis, the function output (y axis) will lie between −1 and 1. The hyperbolic tangent function is used by the system in instances when both positive and negative outputs are expected.

The linear function $$f(x)=x$$

Figure 22C:
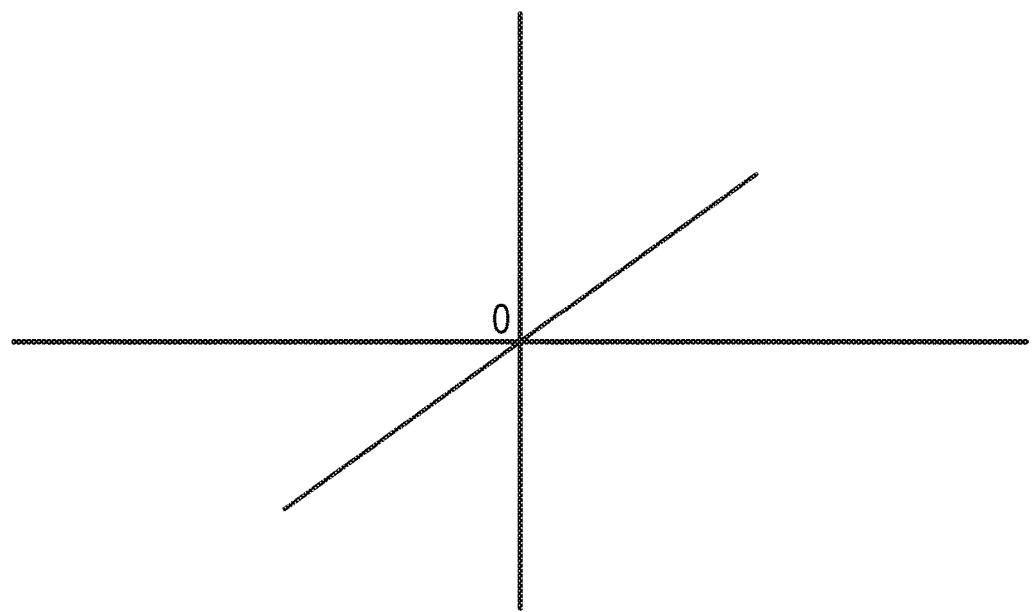

As shown in FIG. 22C, a characteristic of the linear function is that the input and output are the same. The linear function is used by the system in instances where the objective is to replicate the input signal to the output.

The activation functions detailed above are exemplary of activation functions used by the inventive system. One skilled in the art will understand that there are also other activation functions that can be used in neural networks. This disclosure is not intended to be exhaustive, but is intended to describe the fact that the server 2014 employs a plurality of activation functions to accomplish its objectives.

Figure 23:
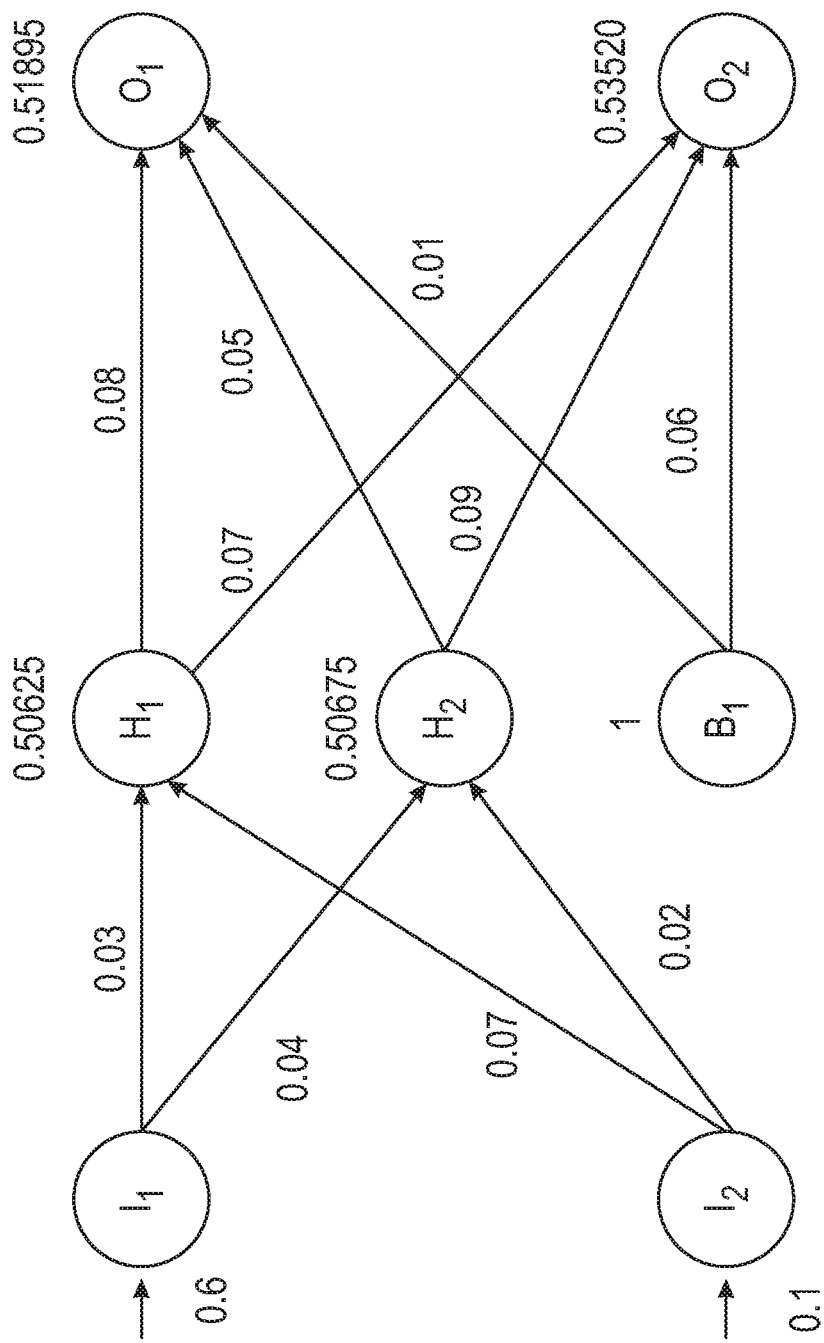
FIG. 23 is an illustration of exemplary computations of the NNM.

A NNM is a neural network architecture with a particular structure tailored to a particular problem statement. An exemplary problem statement the server's 2014 neural networks model is the prediction of whether a baggage item checked in at a particular departure airport is likely to suffer from preventable deviation or not (in this example, a categorical output is predicted). Using a trained NNM, the server 2014 predicts the likely outcome using a plurality of the properties or attributes of the baggage item (the inputs). Each model in the system contains input, output, bias and hidden neurons. The input and output neurons are required whereas the bias and hidden neurons are optional depending on the nature of the specific problem statement and its requirements. Each model also has a structure. The exemplary neural network herein depicted in FIG. 23 is demonstrative of a feed forward structure, however other possible neural network structures or architectures include, but are not limited to ADALINE Neural Network, Adaptive Resonance Theory 1 (ART1), Bidirectional Associative Memory (BAM), Boltzmann Machine, Counterpropagation Neural Network (CPN), Elman Recurrent Neural Network, Hopfield Neural Network, Jordan Recurrent Neural Network, Neuroevolution of Augmenting Topologies (NEAT), Radial Basis Function Network, Recurrent Self Organizing Map (RSOM), Self-Organizing Map (Kohonen), among others. Feedback networks, for example Elman and Jordan Networks, are at times leveraged by the system particularly in instances where the sequence of events (order of data) is material. Each neuron of the neural network model also has a defined activation function. Each neuron may have more than one activation function in different layers. In the exemplary neural network of FIG. 23, the activation function is the sigmoid function. Prior to model training, the model's neurons and their structure as well as the activation function are defined. The training of a model starts with the random selection of a set of initial synaptic weights. During the training process, the synaptic weights are updated after each training iteration (see further description provided herein). The below describes how the values at the neural network nodes $H_1$, $H_2$, $O_1$ and $O_2$ are calculated for given inputs $I_1$ and $I_2$ and a given set of synaptic weights (synaptic weight values for this example are those shown in FIG. 23. This calculation process is used during each model training iteration and subsequently when the trained model is used to make predictions from previously unseen input data:

$H_1$
Sum=0.6*0.03+0.1*0.07
  =0.018+0.007
  =0.025
Output=A(Sum)=0.50625
$H_2$
Sum=0.6*0.04+0.1*0.02
  =0.024+0.002
  =0.027
Output=A(Sum)=0.50675

$O_1$

Sum=0.50625*0.08+0.50675*0.05+1*0.01

=0.0405+0.0253375+0.01

=0.0758375

Output=A(Sum)=0.51895

$O_2$

Sum=0.50625*0.07+0.50675*0.09+1*0.06

=0.0354375+0.0456075+0.06

=0.141045

Output=A(Sum)=0.53520

During the training process, the synaptic weights are adjusted to minimize the error of the output. Thus, the final synaptic weights of the trained model are only known once model training is complete. After successful training of the model, the finalized synaptic weights are then used to make predictions.

Training the NNM

The server 2014 applies machine learning algorithms to modify the synaptic weights of each model's connections as it learns the patterns in the data. Thus, trained models in the system are system models with finalized synaptic weights that result in the most minimal error. Training algorithms along with representative data sets presented to each of the models for the purpose of training are employed by the system to update the synaptic weights of each model's connections with values that minimize the error.

There are two types of error that pertain to neural networks. The first is Local Error (E). Local error is the actual output value computed by the neural network subtracted from the ideal value (i.e. the output value in the training data set). This error is "localized" to particular output neurons, hence the name local error. The other type of error is the error of the neural network, also called network error or global error. The global error is the cumulative effect of the error at each of the outputs (the local error for each output). There are a few types of global error which are briefly discussed below.

Mean Square Error (MSE)

$$\frac{\sum_n E^2}{n}$$

The mean square error (MSE) is the sum the square of all local errors divided by the total number of cases.

Sum of Square Errors (ESS)

$$\frac{\sum_n E^2}{2}$$

The sum of square errors (ESS) is the sum of the square of all local errors divided by two (2).

Root Mean Square Error (RMS)

$$\sqrt{\frac{\sum_n E^2}{n}}$$

The root mean square error (RMS) is the square root of the MSE.

The system generally uses MSE, however, in some specific instances the other methods for determining the global error are used.

To more formally state the objective of using machine learning to train the models in the system, it is most accurate to say that the system employs machine learning algorithms and training data to adjust the synaptic weights for the connections in each model such that the global error is less than a pre-established level. The system is configured with acceptable global error levels that balance the tradeoffs of model overtraining (acceptable global error level too low) and model undertraining (acceptable global error level too high).

Figure 24:
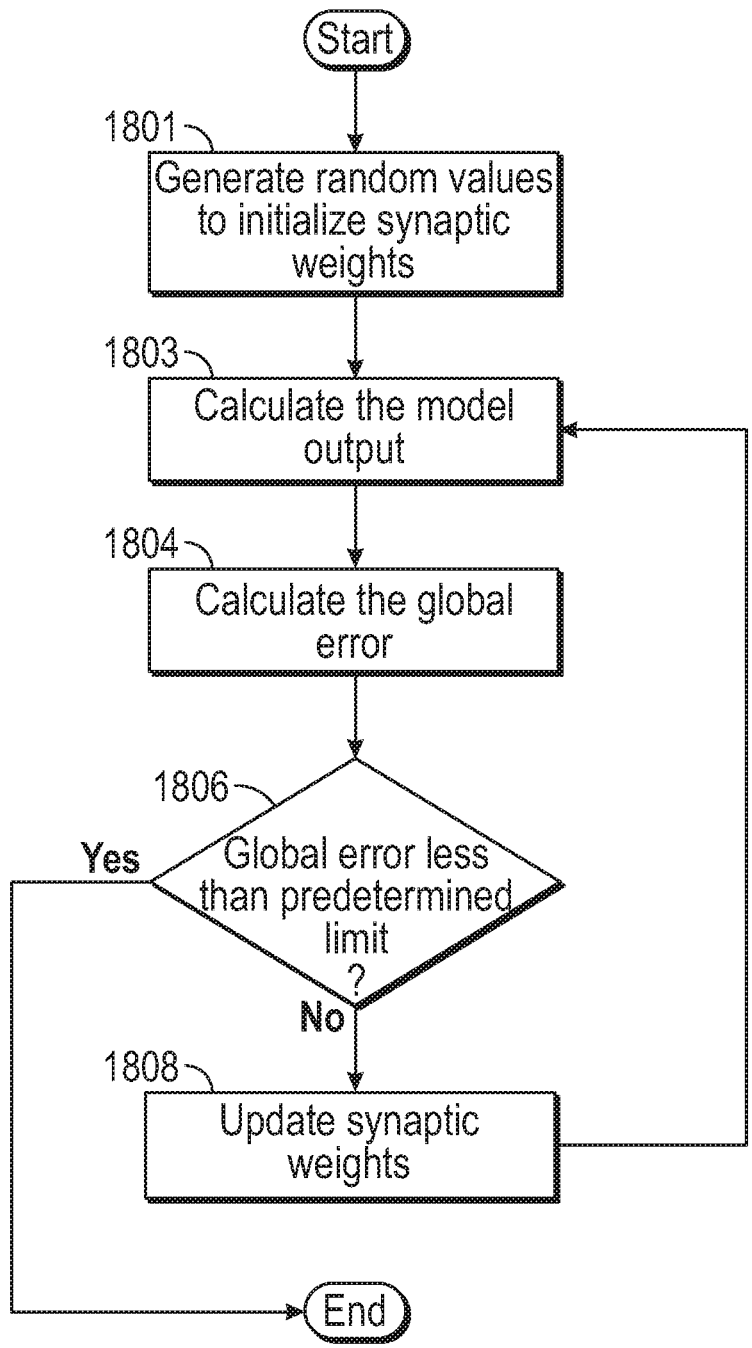
FIG. 24 is a flow diagram illustrating exemplary operations of the system for training the NNM.

Referring to FIG. 24, the approach for training the NNM based upon training data will be discussed. The training data is quantifiable outcomes (deviation or no deviation, deviation probability) of a plurality of past baggage events and attributes of each of the past baggage events. Initially, at 1801, values of the plurality of synaptic weights are assigned to random values. At 1803, the output values of the model are calculated for the current "row" or case in the training data being used for the current training iteration (i.e. "row" being the one event or case used for the current training iteration out of the available events in the training data set) using the initial random synaptic weights. At 1804, the global error for this iteration of the NNM training process is calculated. Particularly, a local error at each of the output(s) is calculated, which is the difference between each output value of the NNM on this iteration and the corresponding actual (known) quantifiable outcomes from the current "row" in the training data set. The global error is then calculated by summing all of the local errors in accordance with MSE, ESS and/or RMS discussed above. If it is determined that the global error is not less than a predetermined acceptable global error (NO at 1806), the values of the synaptic weights are adjusted at 1808, and a new training iteration using another event from the training data set begins (at 1803). As part of this next iteration, the global error is again calculated at 1804. Here, if the global error is never reached after a number of iterations, the model can be revised, such as changing the number of hidden layers, neurons, etc., and the training process can be attempted again. When it is determined that the global error is less than the predetermined acceptable global error (YES at 1806), the trained model is then subjected to validation discussed later.

Different machine learning algorithms as well as different global error calculation methods can be employed to update the synaptic weights. Some of the machine learning algorithms the server can be configured to employ include ADALINE training, backpropagation algorithm, competitive learning, genetic algorithm training, Hopfield learning, Instar and Outstar training, the Levenberg-Marquardt algorithm (LMA), Manhattan Update Rule Propagation, Nelder Mead Training, Particle Swarm (PSO) training, quick propagation algorithm, resilient propagation (RPROP) algorithm, scaled conjugate gradient (SCG), among others. Machine learning algorithm selection is determined based on a number of factors some of which include accuracy of the algorithm, the computation resources available and those required of the algorithm, the available or ideal training time duration, among others.

Figure 25:
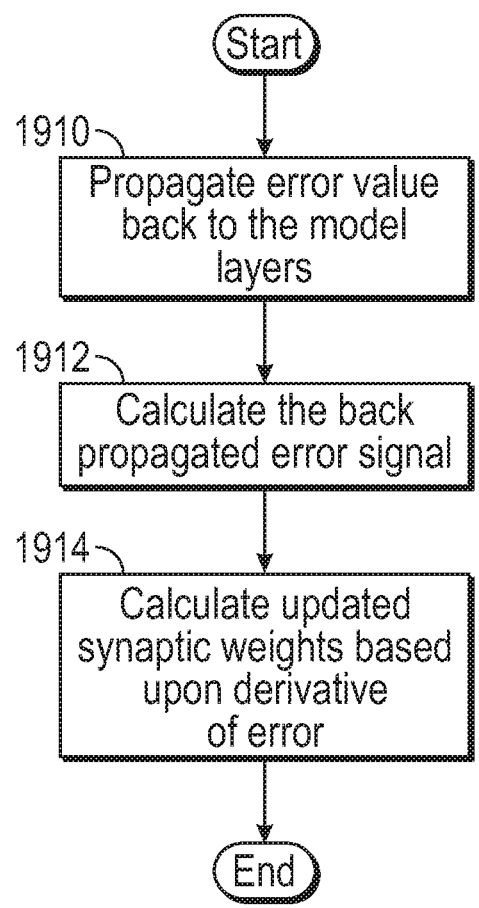
FIG. 25 is a flow diagram illustrating exemplary operations of the system for propagation training (updating the synaptic weights between iterations) of the NNM.

Training the system models is an iterative process referred to as propagation. As discussed above, the process begins by using randomly assigned synaptic connection weights to compute the outcome of the model (1803). Using the known output values for cases in the training data set and the output values computed by the model, the local error at each output, and subsequently the global error of the network is determined (1804). If the global error is not below the pre-established acceptable global error rate a new iteration with updated synaptic weights will ensue. The process for updating the synaptic weights (1808) is referred to as propagation training. As already discussed, the system can be configured to employ one of a variety of methods (algorithms) for updating the synaptic weights during the training process for a given model. Referring to FIG. 25, a gradient-decent procedure can be used to update the synaptic weights on each training iteration. At 1910, the error value is propagated to the model layers. The gradient-decent procedure is used to determine the direction of change of the synaptic weight(s) that will minimize error on the next iteration. Doing this requires model neurons to use differentiable activation functions, such as those already previously discussed herein. At 1912, the back propagated error signal is determined by calculating the error gradient (gradient-decent procedure). The error gradient is the value of the instantaneous slope at the current point on the error function surface plot. Said another way, the error gradient is the derivative value of the error function surface plot, the plot of the error values that correspond to different synaptic weights. The proportion of the error gradient that is used in each iteration of the propagation process is called the learning rate and can be configured in the system (essentially, how much of the derivative value should be applied to update the synaptic weights on each model training iteration). This procedure can vary depending on the propagation algorithm employed by a given model in the system. The larger the learning rate, the larger the synaptic weight changes will be on each iteration and the faster the model will learn. However, if the learning rate is too large, then the changes in the synaptic weights will no longer approximate a gradient decent procedure (a true gradient decent is predicated on infinitesimal steps) and oscillation of the synaptic weights can result (no learning at all). Conversely if the learning rate is too slow, training of the model will be a very lengthy process utilizing large amounts of compute time. The learning rate that is used for training the system models is one that results in brisk learning without triggering oscillation. When the system is configured with optimal learning rates the fastest training of each model is achieved with the smallest compute training time expenditure.

The model propagation training process utilized by the system can also employ the concept of momentum to deal with the challenge of local minima that can complicate backpropagation (the process of following the contour of the error surface with synaptic weight updates moving in the direction of steepest decent), for example, when the network architecture includes a hidden layer. Momentum is the concept that previous changes in the weights should influence the current direction of movement in the weight space (essentially the percentage of previous iteration weight change to be applied to the current iteration). As such, the inclusion of the momentum parameter can help networks employed by the inventive system to "roll past" local minima. In addition, the inclusion of the momentum parameter can also help speed learning, particularly when long flat error surfaces are encountered. At 1914, the updated synaptic weights are calculated based upon the derivative of the error, the defined learning rate and the momentum parameter.

Training and Validation of System Models

Figure 26:
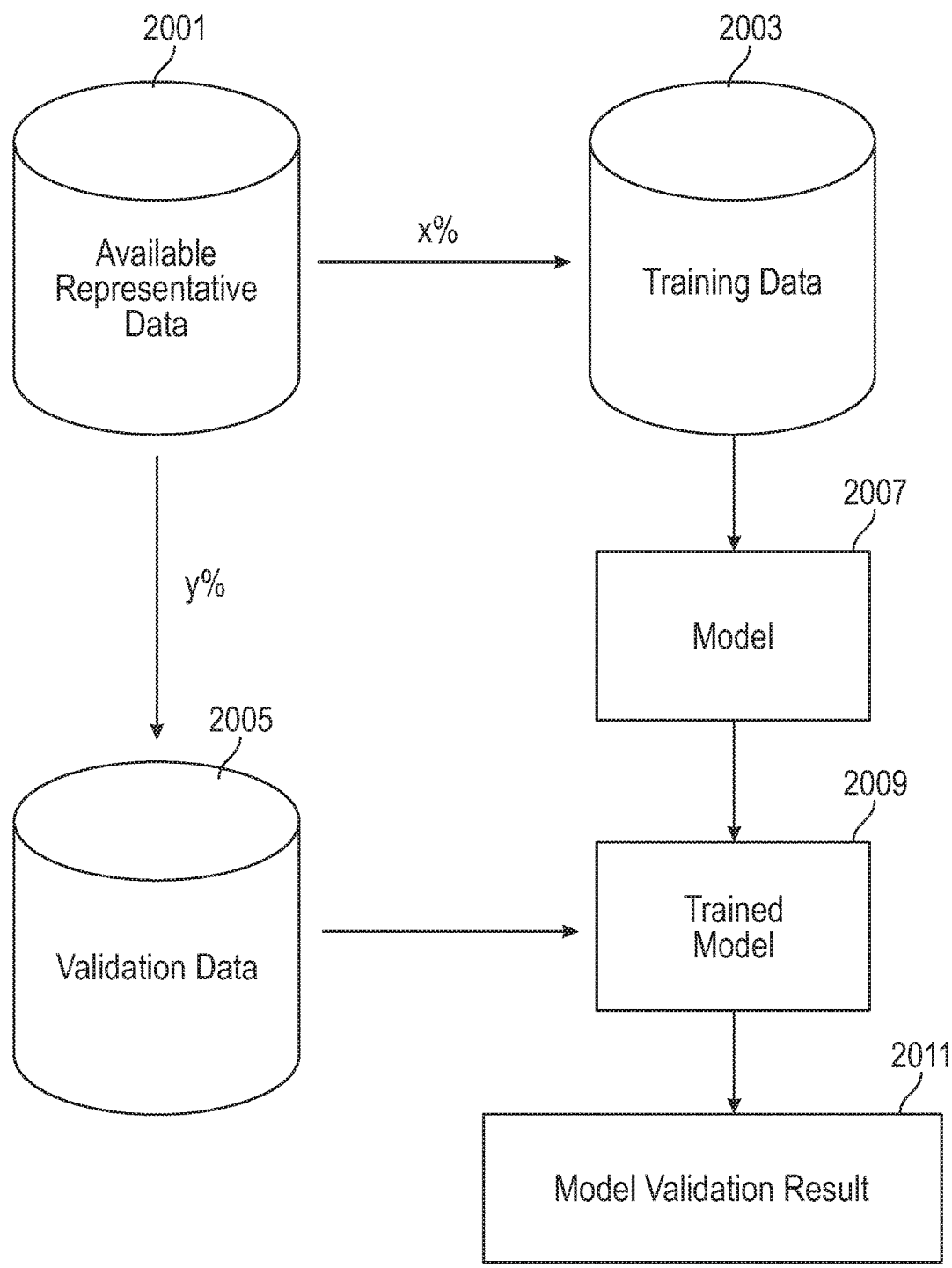
FIG. 26 is block diagram illustrating high level operations of the process for training the NNM and validating the trained NNM.

The training process for the NNM employs a representative data set, which can be a plurality of past events as discussed above. Referring to FIG. 26, the cases in the representative data set 2001 are divided into two unique data sets by some ratio or percent x allocated to the training data set 2003 and percent y allocated to the validation data set 2005. The ratio of cases allocated to the training data set 2003 versus those allocated to the validation data set 2005 varies. Before the allocation of cases to the training data set 2003 or the validation data set 2005, an optional step of data shuffling can be carried out by the system to help ensure all types of data in the representative data set 2001 gets distributed to both the training 2003 and the validation 2005 data sets. The training data set 2003 was used to train the NNM 2009 as discussed above. The validation data set 2005 can be used to validate the trained NNM 2009 because the real outcome of each case in the validation data set is known. The server can generate an output value (model validation result) 2011 of the trained NNM 2009 for each past baggage event of the validation data set 2005, wherein each of the output values 2011 represents a calculated quantifiable outcome of the respective baggage event. Then the server can determine if the output values 2011 correspond to the quantifiable outcome within the predetermined global error.

The training data set 2003 along with the defined system models, the selected machine learning training algorithms and the method each uses for global error calculations, in conjunction with the pre-defined acceptable global error rates are used to train the NNM starting with randomly assigned synaptic weights for each model's neuronal connections. The requisite number of synaptic weight calculation iterations are executed until an acceptable global error level is obtained. Subsequently, the trained model 2009 is then used to predict the outcome for cases in the validation data set 2005, the so called "unseen data" (from the perspective of the trained model). Because the real outcome of each case in the validation data set is known, at this point a validation report can be generated comparing the predicted results with the actual results and the findings can be used to determine the validity of the trained model, essentially whether it is successfully predicting the actual outcomes for the cases in the validation data set. The end result is an assessment of how well the trained system model performs on unseen data.

Using the Trained NNM

Returning to FIG. 16, the backend device receives a plurality of input attributes of a new baggage event. This data may come from a client device, from the database at the server, or a combination. The data is pre-processed (for example, normalized) to generate an input data set, and the data is input into the trained model 1107 which then generates an output value. The output value is then post-processed (for example, de-normalized). Finally, the output value is classified into a deviation risk category (classification task) or a value such as the probability of deviation or the predicted duration of deviation (regression task) to predict the outcome. For example, in the simplest case the de-normalized output value can be a Boolean value (deviation or no deviation). In another case, the output value can be a probability of deviation occurring. In this case, the TMD or server may assign probability ranges which define particular delay categories. In another case, the output value can be a calculated deviation time (predicted duration of deviation). In this case, the TMD or server may assign time ranges to define particular deviation categories.

Unsupervised Learning

Figure 27A:
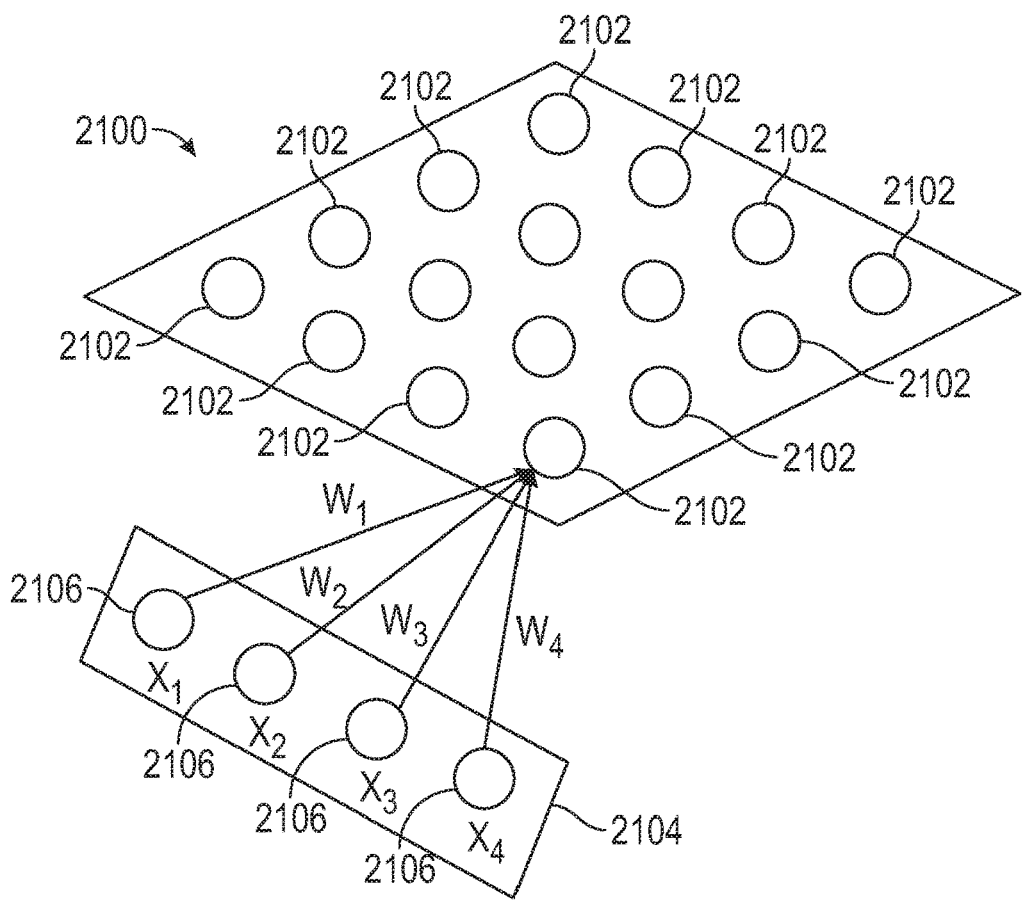
FIGS. 27A-27B is an illustration of an exemplary Self-Organizing Map (SOM) and the input data set to the SOM network.
Figure 27B:
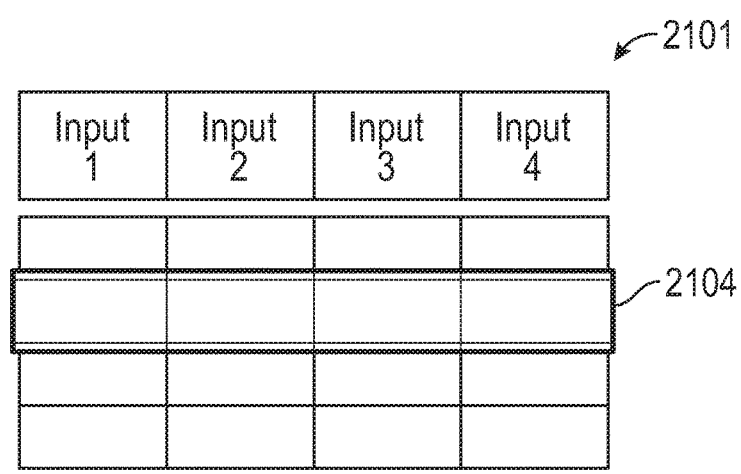
Figure 27C:
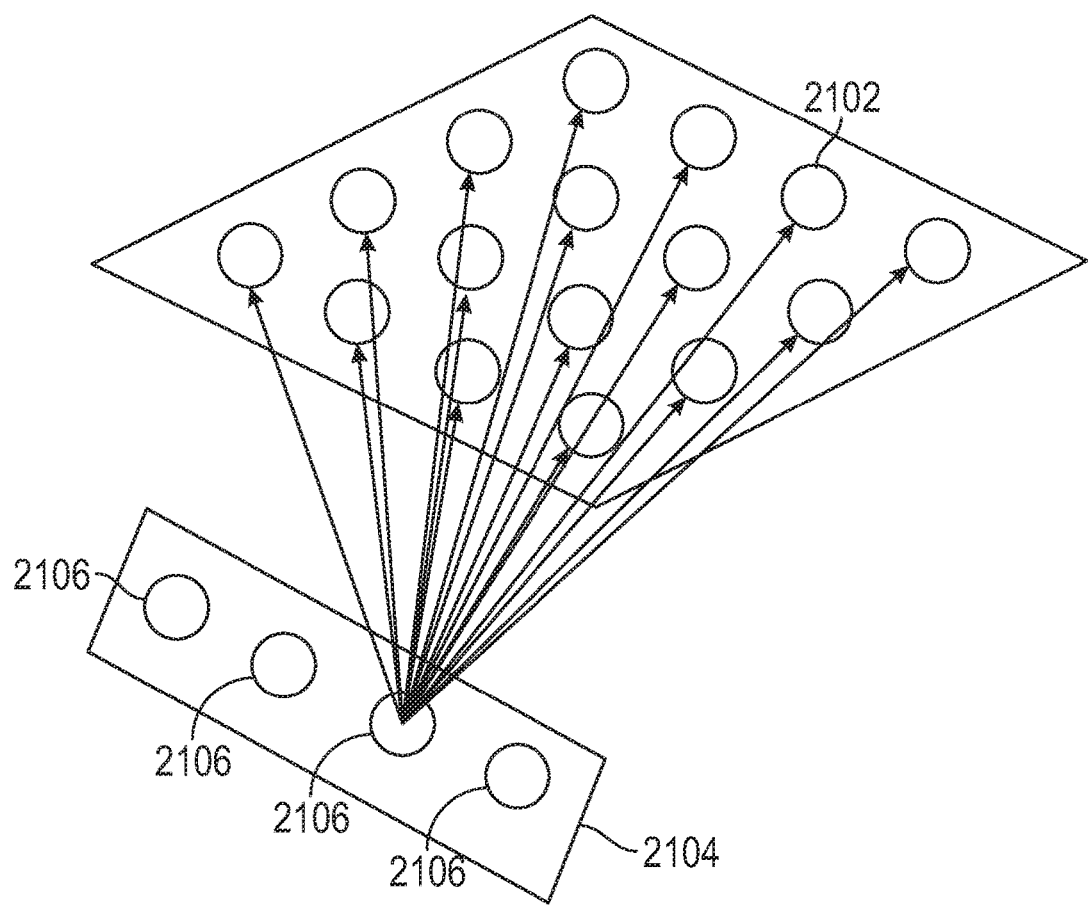
FIG. 27C is an illustration of how each node of the SOM network will contain the connection weights of the connections to all connected input nodes.

The server can also use unsupervised learning techniques as well as supervised learning techniques to determine the group or cluster to which particular events belong. Referring to FIGS. 27A-27B, a Self-Organizing Map (SOM) 2100 is an unsupervised neural network that consists of a grid or lattice of nodes 2102 with a certain structure which may be one, two or three dimensional. The SOM 2100 includes a grid of nodes 2102 on some two (or three) dimensional plane where each node has an x and y coordinate (and z coordinate in the case of a three-dimensional node network), a so called fixed topological position, and an input layer 2104 with various input nodes 2106 that are used to provide input to the SOM network 2100. The input layer 2104 can be a random row from the training data set 2101 (FIG. 27B). The specific number of inputs is dependent on the specifics of the data set. Each input node is connected to every node of the two (or three) dimensional SOM network (FIG. 38C) and each connection has a synaptic connection weight (w), much like that in supervised networks. Each node 2102 of the SOM network 2100 will contain the connection weights of the connections to all connected input nodes. As partially shown in FIG. 27C, each SOM network node 2102 is connected to all input nodes 2106, thus each node of the SOM network will have an equivalent number of connection weights (equivalent to the number of input nodes).

Figure 29:
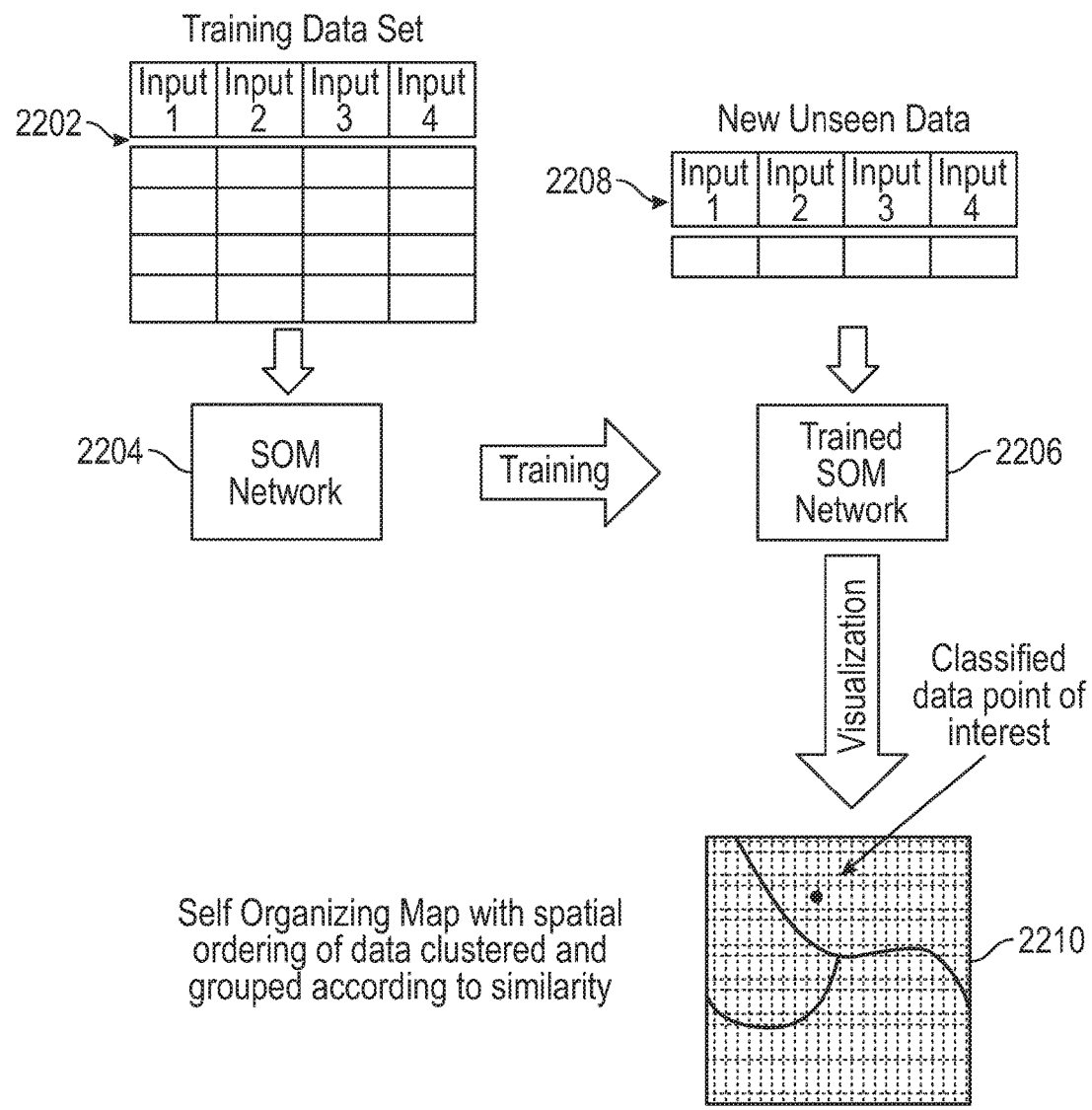
FIG. 29 is a block diagram illustrating high level operations of the process for training the SOM.

A representation of the process for creating, training and using the trained model is shown in FIG. 29. A training data set includes a plurality of attributes of past baggage events. The training data set 2202 is input into the SOM network 2204. The SOM network 2204 is trained to generate the trained SOM network 2206. New data 2208 is input into the trained SOM network 2206. The output of the trained SOM network can be an SOM image 2210 that shows spatial ordering of data clustered and grouped according to similarity such that that the group or cluster to which a given data point of interest belongs can be determined. As discussed later, the SOM image 2210 can be rendered on a client device.

Figure 30:
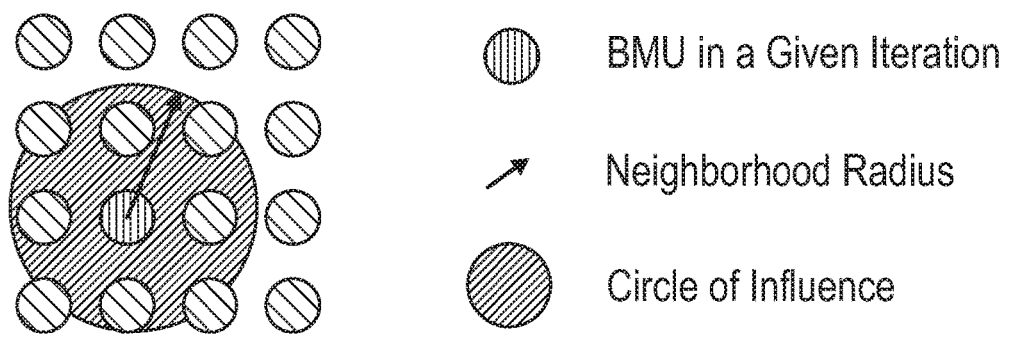
FIG. 30 is an illustration of the process for training the SOM network.

Referring to FIG. 30, the first step in SOM model training is to initialize values of the plurality of synaptic connection weights to random values. The next step is to randomly select one row (one past baggage event) from the training data set, which is most typically normalized (for this purpose) and determine which of the plurality of network nodes is the best matching unit (BMU) according to a discriminant function such as a Euclidean Distance. When a node is selected and compared with the row selected from the training data, the Euclidean Distance which serves as our discriminant function for this competitive network, is calculated, though others, for example, Manhattan distance, can be used. This process is repeated for each SOM node. The SOM node with the smallest Euclidean distance (or said another way, the neuron whose weight vector comes closes to the input vector) will be designated as the BMU for that randomly picked input data row. Thus, the BMU is the closest SOM network node to the randomly picked input data row. Next, the neighborhood radius, or the so called neighborhood kernel (function), is calculated. Usually the Gaussian function is used, although the Bubble function is another possibility. The neighborhood radius allows for the determination of the specific BMU neighborhood nodes in the SOM network to which connection weight updates should be applied on the next training iteration. All nodes within the "circle of influence" corresponding to the neighborhood radius are updated. The procedure used to calculate this radius value is shown below:

$$r(n) = r_0 e^{-\left(\frac{n}{\lambda}\right)}$$

$r_0$=initial radius
n=iteration number
$\lambda$=time constant

Usually a large initial radius value is selected for the purpose of having almost the entire network covered. n is the iteration number and lambda is a time constant (iteration limit). This calculation of the radius is basically a decreasing function whereby the value of r will diminish over the course of the training iterations, another way of saying the topological neighborhood decays with distance or that the topological neighborhood decreases monotonically over the period of iterations. Hence a greater number of SOM nodes are updated early in the training process, and on subsequent rounds there is a smaller number of nodes in the neighborhood of the BMU that get updated. At this point in the training process the connection weights are updated for the BMU and those nodes in the neighborhood of influence. The connection weight update equation is as follows:

$$W_k(n+1) = W_k(n) + \alpha(n) h_{ck}(n)[x(n) - W_k(n)]$$

Where n is the iteration number, k is the index of the node in the SOM network, and $W_k(n+1)$, is the updated connection weight (weight vector of node k) for the next training iteration which is calculated as shown using $\alpha(n)$, a monotonically decreasing learning coefficient (learning rate), $h_{ck}(n)$, the neighborhood kernel (function)—something that, for simplicity can be called the influence factor, and $[x(n) - W_k(n)]$, the difference between $W_k(n)$, the old weights (the weights on the current training iteration), and $x(n)$, a randomly selected row or input pattern from the input data that was used on the current iteration.

Thus, a simplistic way of stating this is the new weights for the next training iteration are calculated by adding the old weights from the current training iteration to the product of the learning rate multiplied by the influence factor multiplied by the difference or delta between the old weights and the randomly picked input data used for a given training iteration. Note the influence factor is often a radial based function such as the Gaussian function (though as mentioned earlier, other types of radial functions can also be used) and this is the reason why the nodes closest to the BMU have or receive more influence than those further away from the BMU which are updated by a smaller amount. Also, in regards to the learning rate, it decreases (decays) over time, meaning that in the earlier phases of the training process, there is more learning, but over the training period the learning effect will decrease in each sequential iteration. The delta between the old weights and the randomly picked input data used in a given training iteration is a determinant of how different the current SOM network node is in comparison with the randomly picked input data row used on the given training iteration. Hence, these three factors are the determinants of the updated connection weights that should be used on each subsequent training iteration for the SOM network nodes. So the learning rate and the influence factor decay over the period of iteration to allow for the proper convergence of the solution such that a stable result can be obtained at the end of training. The training process is repeated for a fixed number of N iterations to generate the trained SOM network.

Figure 28:
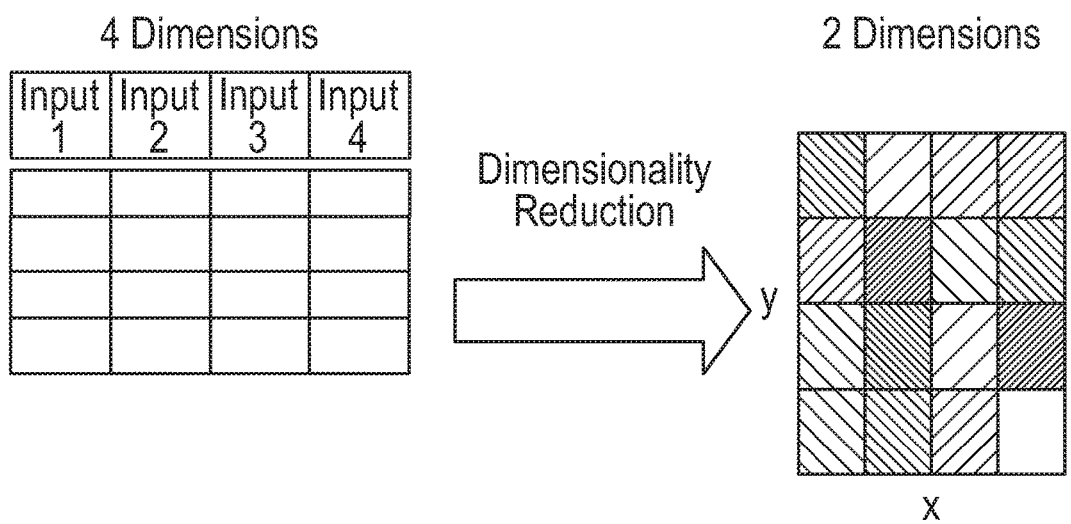
FIG. 28 is an illustration of the SOM network used to reduce dimensionality of the input data sets.

Returning to FIG. 17, an exemplary data set includes a plurality of data [1, 2 . . . N], and a number of properties [1, 2 . . . N] for each data. The data set can be a plurality of past baggage events and the properties can be a number of attributes of each past baggage event. The high dimensionality of the data sets can make visualization of the data difficult. As illustrated in FIG. 28, the dimensionality reduction aspect of SOM networks allows data of high dimensionality to be projected to a two-dimensional grid which expresses the similarity of samples and the distance between them. However, the mere position on the map cannot sufficiently embody the complexity of an n-dimensional vector. The challenge of information representation is a mature area of research and numerous approaches of displaying multi-dimensional multivariate data have been proposed as discussed in the article entitled "30 Years of Multidimensional Multivariate Visualization" authored by Wong and Bergeron (1997), the contents of which are hereby incorporated by reference. One such technique therein described utilized by the system is Scalable Vector Graphics (SVG), an XML markup language for describing two-dimensional vector graphics, both static and animated.

Figure 31:
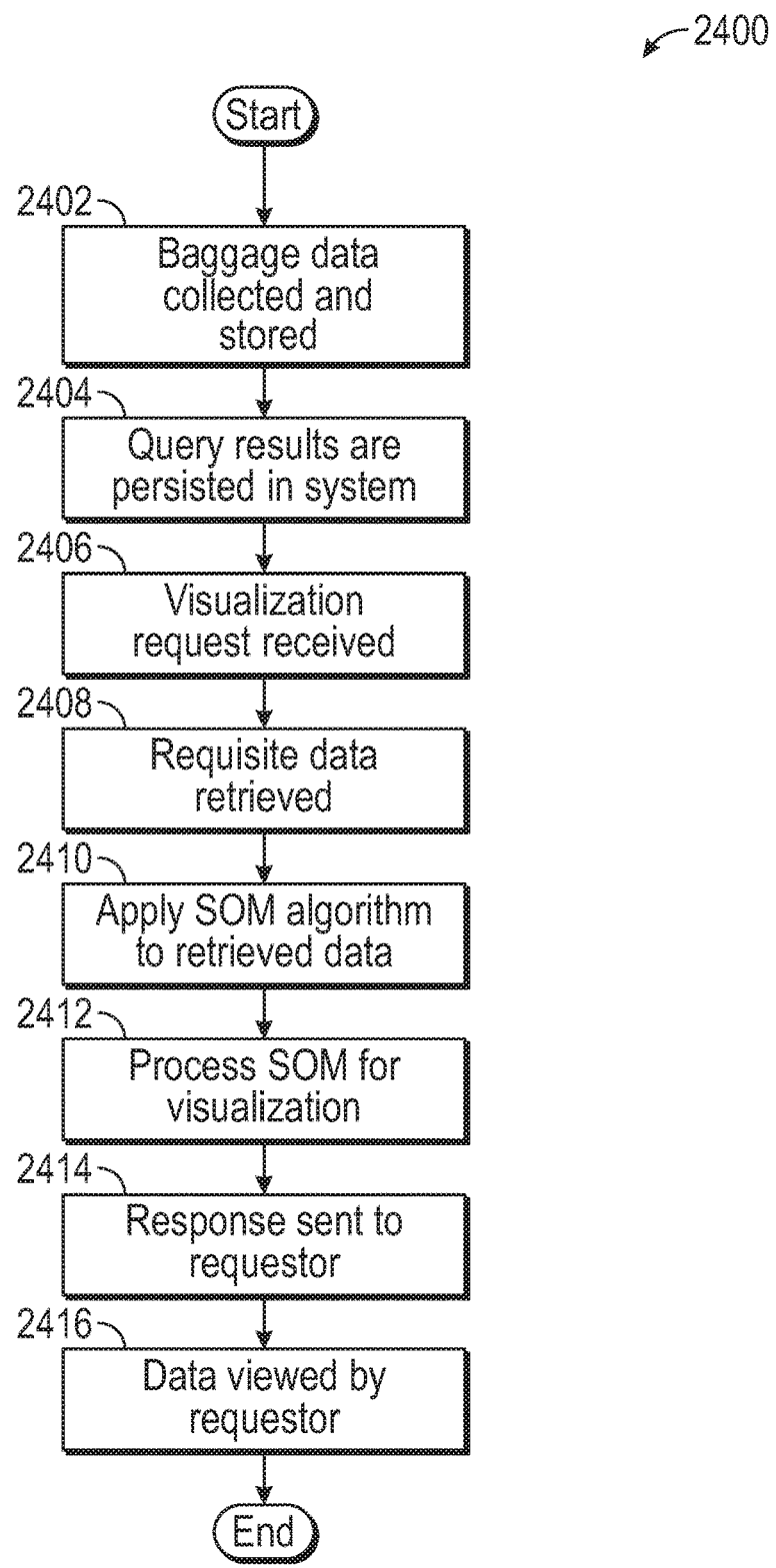
FIG. 31 is a flow diagram illustrating exemplary operations of the system to generate the graphical image including the visualization.

Referring to FIG. 31, an exemplary process 2400 by which the system can employ SOM network to take a data set of baggage events defined by n-dimensional input attributes and generate a visualization of the results after passing the data into a SOM network will be discussed. At 2402, baggage data is collected and stored. Particularly, the DCE collects identification and location data on the baggage from the RFID tags as discussed above and transmits it to the backend devices. This data can be stored in the database at the server with respect to the baggage item as discussed above. At 2404, the server (or TMD) can maintain query results in the memory. At 2406, the TMD receives a visualization request from a client device or web browser via the network with query parameters. At 2408, the TMD sends a data request with the query parameters to the server, which retrieves from the database the data sets consistent with the request. At 2410, the server inputs the data sets to the trained SOM network. At 2412, the server generates a visualization or graphical image based upon the output from the SOM network. At 2414, the server sends the graphical image to the TMD, which either sends it to the client device and/or renders the image on a display of a website. The output produced can be groupings or clustering of baggage items with similar characteristics, much like the classical "market segmentation" or "document classification" tasks for which SOMs are widely employed. This SOM output can be generated from a variety of vantage points or perspectives with one or more specified criteria, for example, specific time ranges, or for only deviated baggage, or only for a particular subset of baggage handled by a particular employee, a group of employees, a service line, a group of service lines, an airport facility or a group of airport facilities in a given region, to name a few examples. SOM techniques can also be employed to predict the classification, type, or grouping of a particular baggage leveraging the attributes or inputs from an already existing data set of baggage events, for example.

Exemplary Implementations

Exemplary implementations will be discussed for simple cases in which a NNM is created, trained and validated to: (1) predict a location at which a baggage item is lost; (2) predict whether a given baggage item is likely to be deviated; (3) predict whether there is a security threat with regards to a baggage item; and (4) predict whether the baggage item was stolen. These examples were selected for simplicity and the inputs were crafted to be of a flavor that is easily understood by a human, while also still being demonstrative of the inventive system's capabilities. However, the examples are not intended to denote or to imply any limitation to the scope of attributes consumed as inputs by the system nor the scope or extent of the system's outputs and its ability to predict these outputs. While in practice the models will be more complicated, the embodiment herein is demonstrative of the modeling process (the process of developing the neural network architecture) utilized in the inventive system. The example of the model's implementation, training, and validation is provided utilizing the c# programming language (Microsoft) and an open source machine learning library (Encog). However, the neural network models can be implemented in any variety of computer languages or logic and can be trained utilizing appropriately selected machine learning training algorithms as implemented in a variety of $3^{rd}$ party libraries or in-house proprietary code. The exemplary embodiment herein is a simple feed forward neural network.

The backend devices (TMD and server) can be employed by an airport system or airline. For example, the database at the server device can store historical baggage events data from an airport(s). Each of these historical baggage events provide input data, specifically an attribute about the baggage item, an attribute about the baggage handlers(s), an attribute about the airport, and an output, namely whether the baggage was deviated or not (input attributes). In the following examples, the input attributes are all Boolean values.

In the first example, the input attributes are baggage location registered: (N1) at check in desk; (N2) placed on conveyor system; (N3) passing conveyor location A; (N4) passing through baggage security scanner; (N5) passing conveyor location B; (N6) as present on tarmac tram 1; (N7) as no longer present on tarmac tram 1; (N8) as placed on gate ABC baggage compartment conveyor system; and (N9) as arrived in baggage compartment on airplane with ID XYZ. The output attribute is Location Lost.

| AVAILABLE DATA SET (PRE-SHUFFLING) | | | | | | | | | |
|---|---|---|---|---|---|---|---|---|---|
| N1 | N2 | N3 | N4 | N5 | N6 | N7 | N8 | N9 | OUTPUT |
| 1 | 1 | 1 | 1 | 1 | 0 | 0 | 0 | 0 | location-b |
| 1 | 1 | 1 | 1 | 1 | 0 | 0 | 0 | 0 | location-b |
| 1 | 1 | 1 | 1 | 1 | 0 | 0 | 0 | 0 | location-b |
| 1 | 1 | 1 | 1 | 1 | 0 | 0 | 0 | 0 | location-b |
| 1 | 1 | 1 | 1 | 1 | 0 | 0 | 0 | 0 | location-b |
| 1 | 1 | 1 | 1 | 1 | 0 | 0 | 0 | 0 | location-b |
| 1 | 1 | 1 | 1 | 1 | 1 | 1 | 0 | 0 | tarmac |
| 1 | 1 | 1 | 1 | 1 | 1 | 1 | 0 | 0 | tarmac |
| 1 | 1 | 1 | 1 | 1 | 1 | 1 | 0 | 0 | tarmac |
| 1 | 1 | 1 | 1 | 1 | 1 | 1 | 0 | 0 | tarmac |
| 1 | 1 | 1 | 1 | 1 | 1 | 1 | 0 | 0 | tarmac |
| 1 | 1 | 1 | 1 | 1 | 1 | 1 | 0 | 0 | tarmac |
| 1 | 1 | 1 | 1 | 1 | 1 | 1 | 1 | 1 | not-lost |
| 1 | 1 | 1 | 1 | 1 | 1 | 1 | 1 | 1 | not-lost |
| 1 | 1 | 1 | 1 | 1 | 1 | 1 | 1 | 1 | not-lost |
| 1 | 1 | 1 | 1 | 1 | 1 | 1 | 1 | 1 | not-lost |
| 1 | 1 | 1 | 1 | 1 | 1 | 1 | 1 | 1 | not-lost |
| 1 | 1 | 1 | 1 | 1 | 1 | 1 | 1 | 1 | not-lost |
| 1 | 1 | 1 | 1 | 1 | 1 | 1 | 1 | 1 | not-lost |
| 1 | 1 | 1 | 1 | 1 | 1 | 1 | 1 | 1 | not-lost |
| 1 | 1 | 1 | 1 | 1 | 1 | 1 | 1 | 1 | not-lost |
| 1 | 1 | 1 | 1 | 1 | 1 | 1 | 1 | 1 | not-lost |

The input data set training data and the output data from the above table is next put into an array of double arrays. One is created for the input data and one is created for the output data. Equilateral encoding can be used to represent the nominal categories of the output data with double values within a normalization range of 0 to 1. For example, the values for [location], [tarmac] and [not lost] can be [0.5, 1], [0.933, 0.25] and [0.06698, 0.25] as shown in FIG. 19B.

The crux of any application of machine learning is development of an appropriate model for the problem that needs to be solved. For, for this simplistic example, a simple feed forward neural network is used. The neural network includes an input layer with nine input nodes in the input layer, a hidden layer and an output layer. For each input neuron, a linear activation function is employed to mirror the input. A hidden layer is also specified for the model, containing nine neurons as well as bias neuronal input. For each hidden layer neuron, the Sigmoid activation function is specified. Finally, for the current problem, two output neurons are required in the output network layer. No bias neuronal input is included, and again the Sigmoid activation function is specified. Once the networks neuronal layer architecture has been defined, the network is finalized and the synaptic weights are initialized to random values.

First Example Architecture (Two Outputs)
```
static void CreateNetwork(FileInfo networkFile)
{
  var network=new BasicNetwork( );
  network.AddLayer(new BasicLayer(new ActivationLinear( ) true, 9));
  network.AddLayer(new BasicLayer(new ActivationSigmoid( ) true, 9));
  network.AddLayer(new BasicLayer(new ActivationSigmoid( ) false, 2));
  network.Structure.FinalizeStructure( );
  network. Reset( );
  EncogDirectoryPersistence.SaveObject(networkFile, (BasicNetwork)network);
}
```

After the network architecture is finalized, the model is ready for training. The input data and encoded/normalized output data are preferably shuffled and split into a training data set and a validation data set.

A first order resilient propagation (RProp) supervised learning algorithm can be utilized to train the model. The training data set is passed into the neural network which has been configured with the RProp training algorithm.

A predefined acceptable global error value of global error less than or equal to 0.01 has been decided upon and is used as the training iteration terminating condition for the do while loop. Multiple training iterations are executed and the global error at the end of each iteration is determined and assessed to see if it meets the established terminating condition. If an acceptable global error level has not yet been achieved, the synaptic weights for each interneuron connection in the network will be subsequently adjusted and another training iteration then ensues. This process is continued until the updated synaptic weights in a given training iteration yield an output with global error less than the predefined condition. Once this terminating condition is met, the end result is the trained model.

Figure 32A:
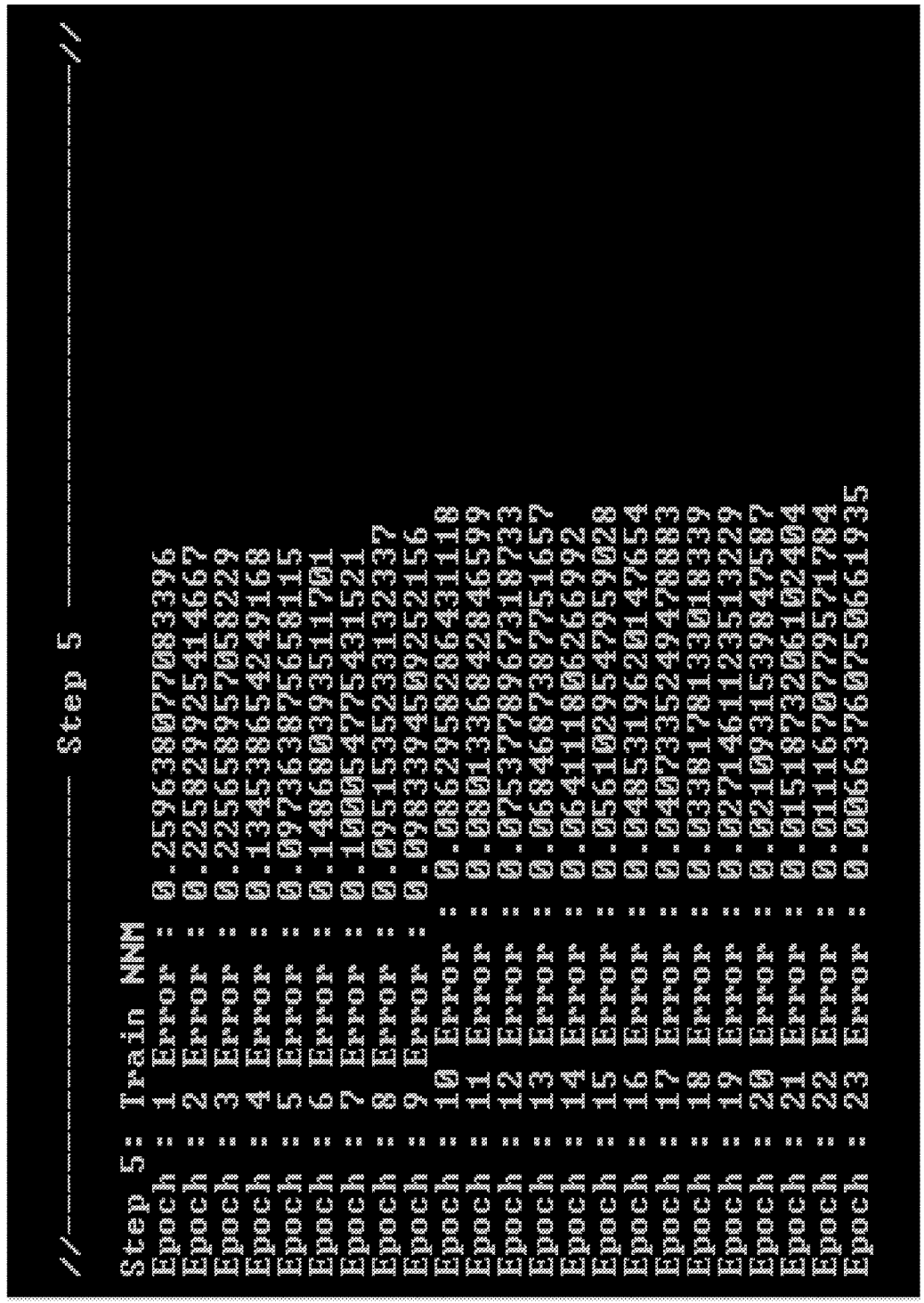
FIGS. 32A-32D are illustrations of iterative global error outputs when training a NNM.

Referring to FIG. 32A, the output of each training iteration in this demonstrative example is shown. A total of 23 training iterations were required before an acceptable global error level was attained.

Now that the exemplary neural network model is trained and "learned," it is ready to undergo validation. For the purpose of this exemplary embodiment, the validation data set is passed into the trained model to assess its performance.

Figure 33A:
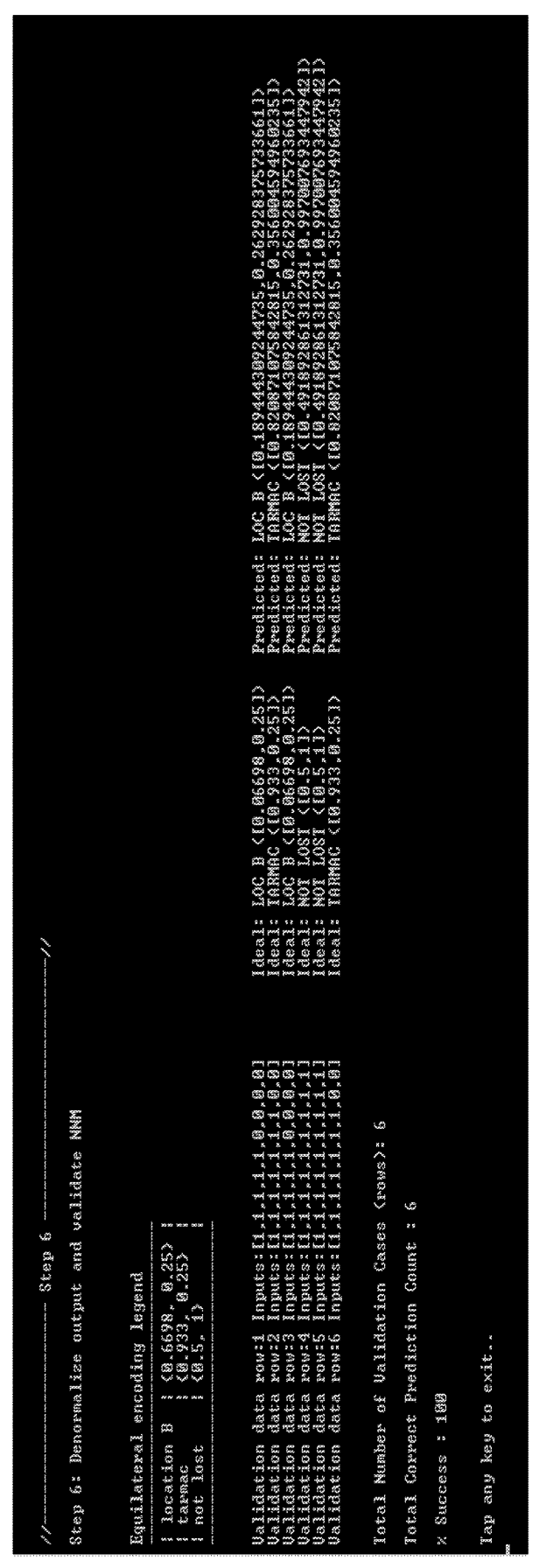

The trained model's performance with this training data set are shown in FIG. 33A. For each input, the trained model's predicted output nicely approximates the ideal output providing evidence that the model is performant at predicting the outcome in all presented cases.

In the second example, the input attributes (N1)-(N9) are same as the first example. The output attribute is Deviated (lost) or not deviated and is also a Boolean value. A simple feed forward neural network is again used. The neural network includes an input layer with nine input nodes in the input layer, a hidden layer and an output layer. For each input neuron, no activation function is used. A hidden layer is also specified for the model, containing nine neurons as well as bias neuronal input. For each hidden layer neuron, the Sigmoid activation function is specified. Finally, for the current problem, one output neuron is required in the output network layer. No bias neuronal input is included, and again the Sigmoid activation function is specified. Once the networks neuronal layer architecture has been defined, the network is finalized and the synaptic weights are initialized to random values.

Second Example Architecture (One Output)
```
private static BasicNetwork CreateNetwork( )
{
  var network=new BasicNetwork( );
  // input layer, 9 neurons, with bias neuron, no activation
    fxn network.AddLayer(new BasicLayer(null, true, 9));
  // hidden layer, 9 neurons, with bias neuron, sigmoid
    activation fxn network.AddLayer(new BasicLayer
    (new ActivationSigmoid( ) true, 9));
  // output layer, 1 neuron, no bias neuron, sigmoid activation fxn network.AddLayer(new BasicLayer(new ActivationSigmoid( ) false, 1)); network.Structure.FinalizeStructure( );
  // randomly initialize network synaptic weights
  network. Reset( );
  return network;
}
```

| AVAILABLE DATA SET (PRE-SHUFFLING) | | | | | | | | | |
|---|---|---|---|---|---|---|---|---|---|
| N1 | N2 | N3 | N4 | N5 | N6 | N7 | N8 | N9 | OUTPUT |
| 1 | 0 | 0 | 0 | 0 | 0 | 0 | 0 | 0 | 1 |
| 1 | 1 | 0 | 0 | 0 | 0 | 0 | 0 | 0 | 1 |
| 1 | 1 | 1 | 0 | 0 | 0 | 0 | 0 | 0 | 1 |
| 1 | 1 | 1 | 1 | 0 | 0 | 0 | 0 | 0 | 1 |
| 1 | 1 | 1 | 1 | 1 | 1 | 1 | 1 | 1 | 0 |
| 1 | 1 | 1 | 1 | 1 | 0 | 0 | 0 | 0 | 1 |
| 1 | 1 | 1 | 1 | 1 | 1 | 0 | 0 | 0 | 1 |
| 1 | 1 | 1 | 1 | 1 | 1 | 1 | 0 | 0 | 1 |
| 1 | 1 | 1 | 1 | 1 | 1 | 1 | 1 | 0 | 1 |
| 1 | 1 | 1 | 1 | 1 | 1 | 1 | 1 | 1 | 0 |
| 1 | 1 | 1 | 1 | 1 | 1 | 1 | 1 | 0 | 1 |
| 1 | 1 | 1 | 1 | 1 | 1 | 1 | 0 | 0 | 1 |
| 1 | 1 | 1 | 1 | 1 | 1 | 0 | 0 | 0 | 1 |
| 1 | 1 | 1 | 1 | 1 | 0 | 0 | 0 | 0 | 1 |
| 1 | 1 | 1 | 1 | 0 | 0 | 0 | 0 | 0 | 1 |
| 1 | 1 | 1 | 1 | 1 | 1 | 1 | 1 | 1 | 0 |
| 1 | 1 | 1 | 0 | 0 | 0 | 0 | 0 | 0 | 1 |
| 1 | 1 | 0 | 0 | 0 | 0 | 0 | 0 | 0 | 1 |
| 1 | 0 | 0 | 0 | 0 | 0 | 0 | 0 | 0 | 1 |
| 1 | 1 | 1 | 1 | 1 | 1 | 1 | 1 | 1 | 0 |

Figure 32B:
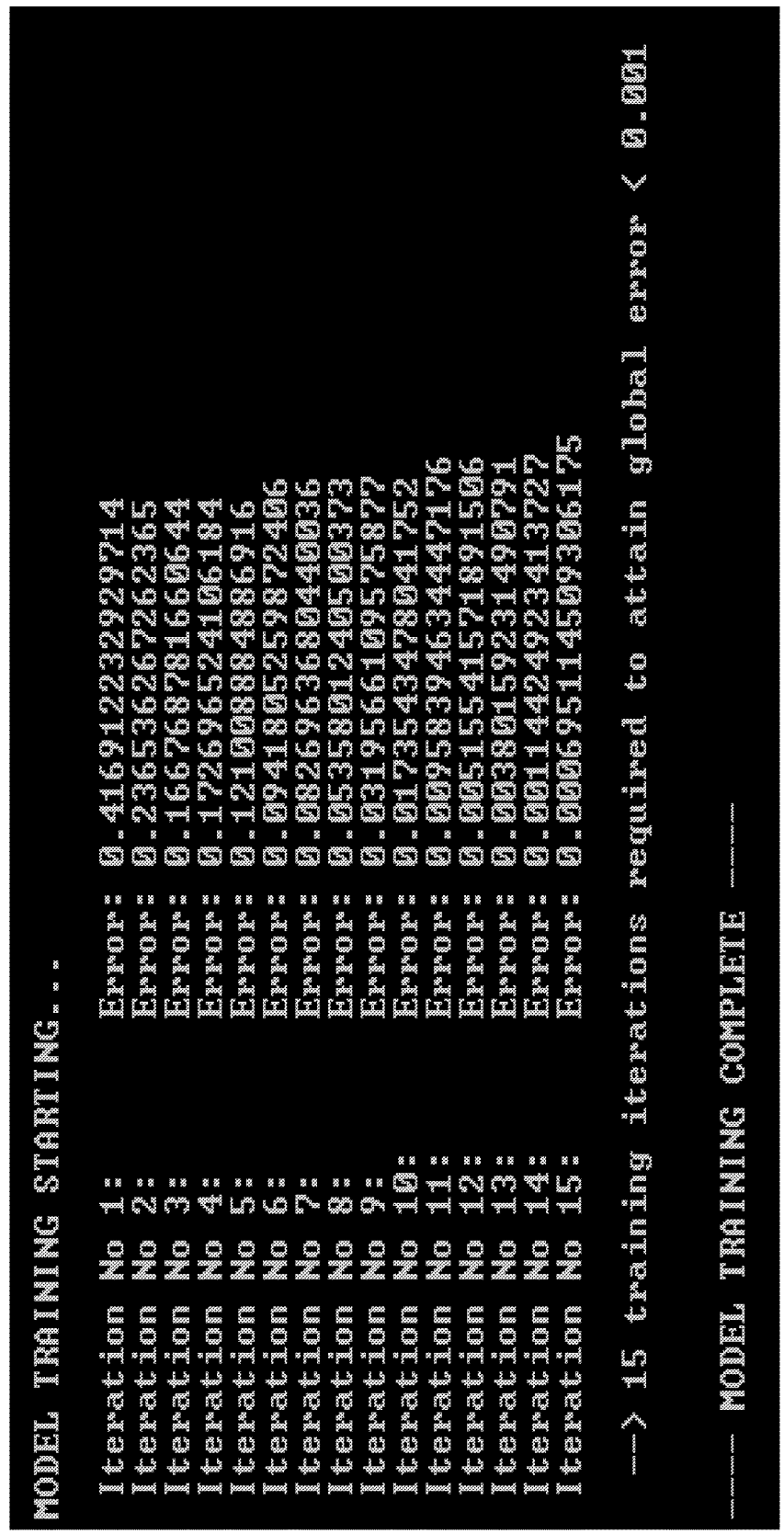

Referring to FIG. 32B, the output of each training iteration in this demonstrative example is shown. A total of 15 training iterations were required before an acceptable global error level was attained.

Now that the exemplary neural network model is trained and "learned," it is ready to undergo validation. For the purpose of this exemplary embodiment, the training data is passed into the trained model to assess its performance.

Figure 33B:
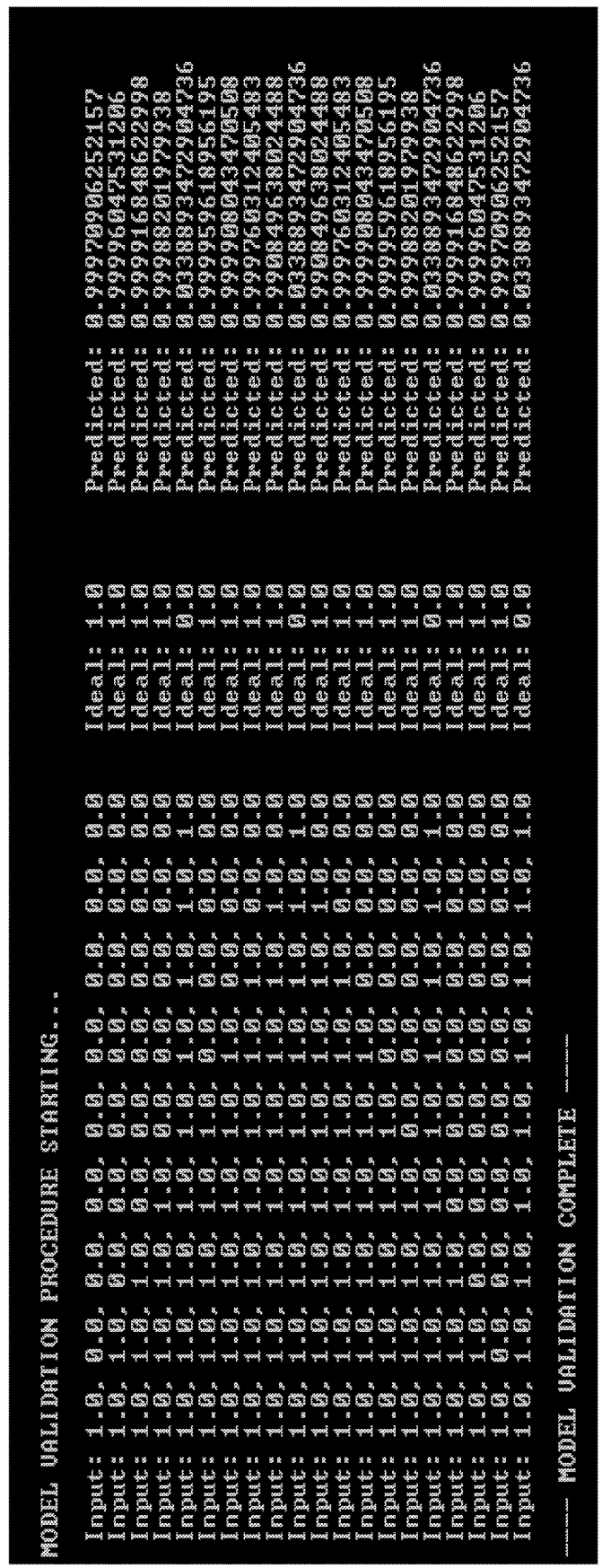

The trained model's performance with this training data set are shown in FIG. 33B. For each input, the trained model's predicted output nicely approximates the ideal output providing evidence that the model is performant at predicting the outcome in all presented cases.

In the third example, the input attributes (N1)-(N9) are same as the first two examples and the same network architecture as the second example is used. The output attribute is security threat or no security threat and is also a Boolean value.

| AVAILABLE DATA SET (PRE-SHUFFLING) | | | | | | | | | |
|---|---|---|---|---|---|---|---|---|---|
| N1 | N2 | N3 | N4 | N5 | N6 | N7 | N8 | N9 | OUTPUT |
| 0 | 0 | 0 | 0 | 1 | 1 | 1 | 1 | 1 | 1 |
| 1 | 1 | 1 | 0 | 1 | 1 | 1 | 1 | 1 | 1 |
| 0 | 0 | 0 | 0 | 0 | 1 | 1 | 1 | 1 | 1 |
| 0 | 0 | 0 | 0 | 0 | 0 | 1 | 1 | 1 | 1 |
| 0 | 0 | 0 | 0 | 0 | 0 | 0 | 1 | 1 | 1 |
| 1 | 1 | 1 | 1 | 1 | 1 | 1 | 1 | 1 | 0 |
| 1 | 1 | 1 | 1 | 1 | 1 | 1 | 1 | 1 | 0 |
| 0 | 1 | 1 | 1 | 1 | 1 | 1 | 1 | 1 | 0 |
| 1 | 0 | 1 | 1 | 1 | 1 | 1 | 1 | 1 | 0 |
| 1 | 1 | 1 | 1 | 1 | 1 | 1 | 1 | 1 | 0 |
| 0 | 1 | 1 | 1 | 1 | 1 | 1 | 1 | 1 | 0 |
| 0 | 0 | 0 | 0 | 1 | 1 | 1 | 1 | 1 | 1 |
| 1 | 1 | 1 | 0 | 1 | 1 | 1 | 1 | 1 | 1 |
| 0 | 0 | 0 | 0 | 0 | 1 | 1 | 1 | 1 | 1 |
| 0 | 0 | 0 | 0 | 0 | 0 | 1 | 1 | 1 | 1 |
| 0 | 0 | 0 | 0 | 0 | 0 | 0 | 1 | 1 | 1 |
| 1 | 1 | 1 | 1 | 1 | 1 | 1 | 1 | 1 | 0 |
| 1 | 1 | 1 | 1 | 1 | 1 | 1 | 1 | 1 | 0 |
| 0 | 1 | 1 | 1 | 1 | 1 | 1 | 1 | 1 | 0 |
| 1 | 1 | 1 | 1 | 1 | 1 | 1 | 1 | 1 | 0 |
| 1 | 1 | 1 | 1 | 1 | 1 | 1 | 1 | 1 | 0 |

Figure 32C:
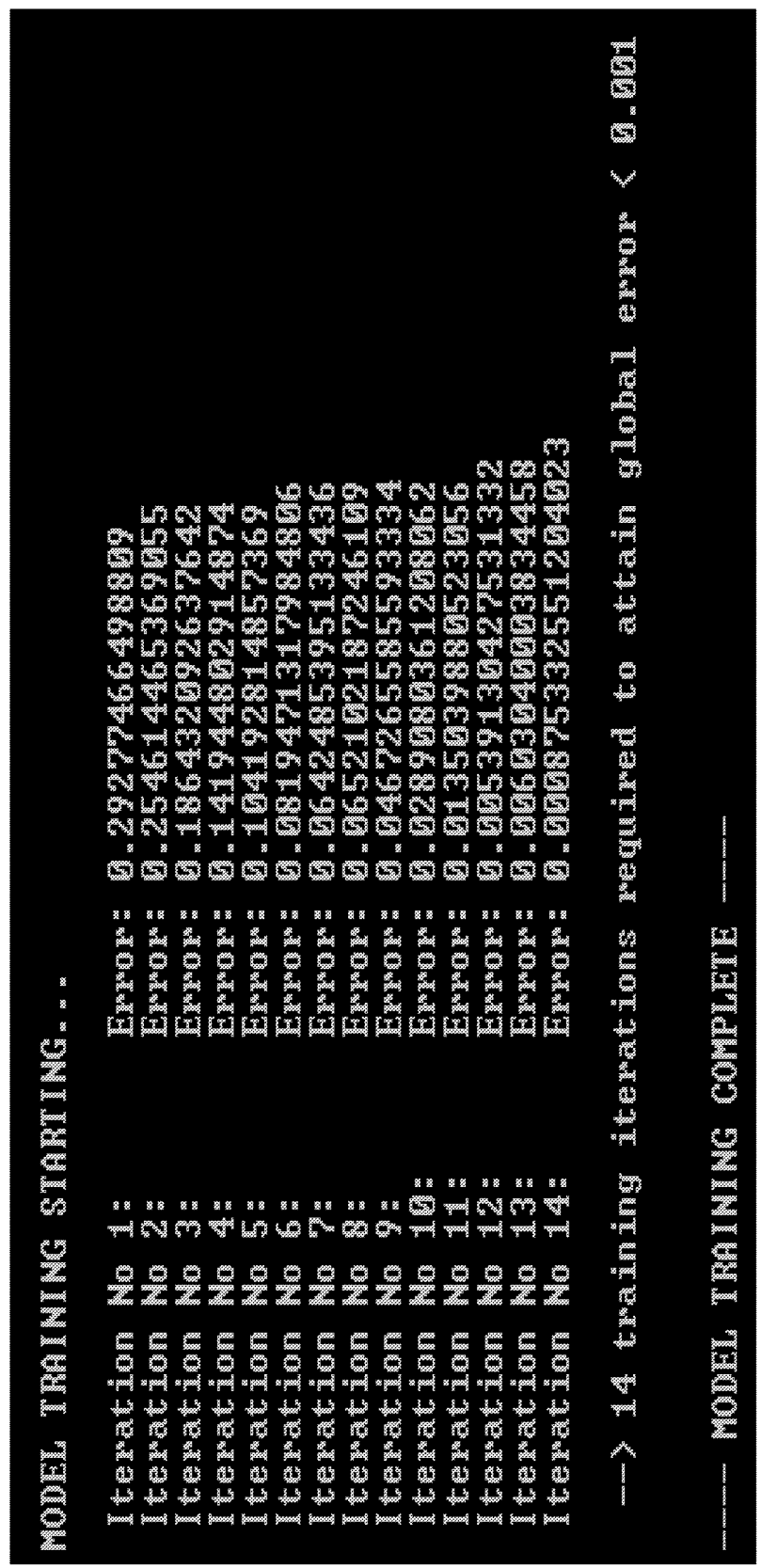

Referring to FIG. 32C, the output of each training iteration in this demonstrative example is shown. A total of 14 training iterations were required before an acceptable global error level was attained.

Now that the exemplary neural network model is trained and "learned," it is ready to undergo validation. For the purpose of this exemplary embodiment, the training data is passed into the trained model to assess its performance.

Figure 33C:
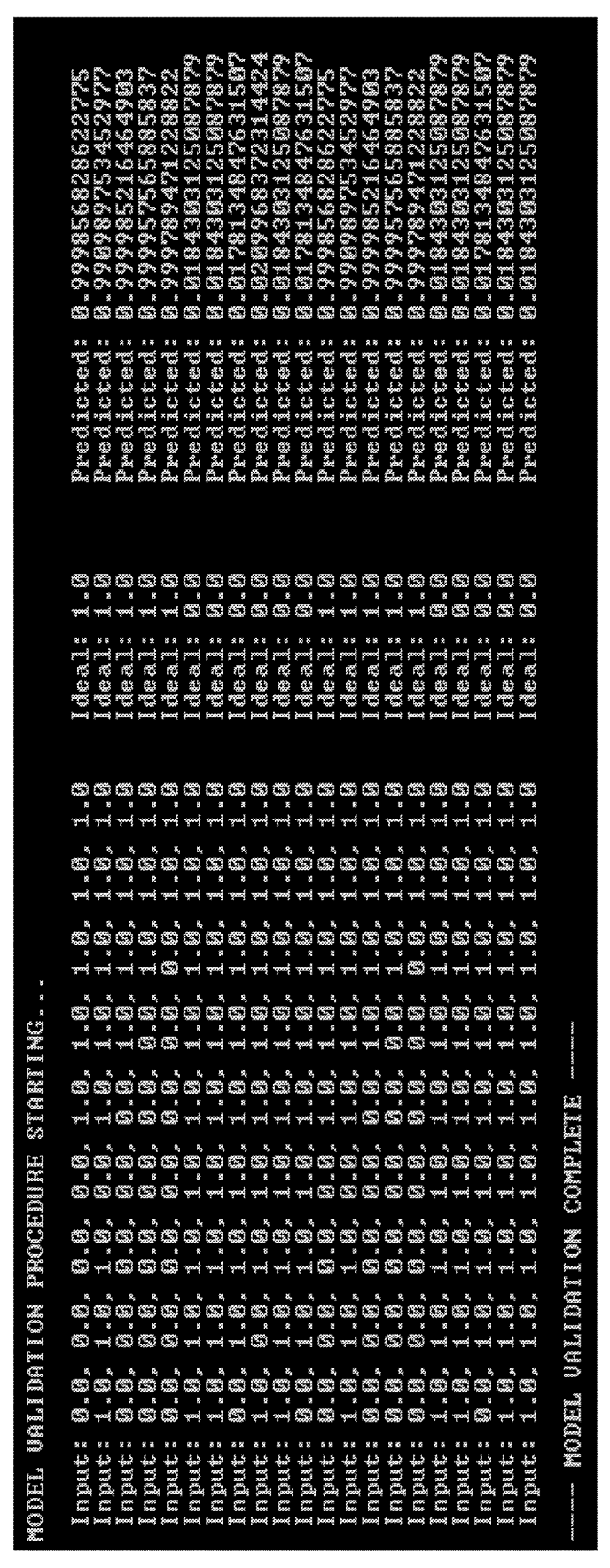

The trained model's performance with this training data set are shown in FIG. 33C. For each input, the trained model's predicted output nicely approximates the ideal output providing evidence that the model is performant at predicting the outcome in all presented cases.

In the fourth example, the input attributes are baggage location registered as: (N1) present in airplane ID XYZ baggage compartment; (N2) not present in airplane ID XYZ baggage compartment; (N3) present on tarmac tram 5; (N4) not present on tarmac tram 5; (N5) placed on conveyor system intake belt on tarmac; (N6) present on baggage carousel ID ABC; (N7) registered in proximity to matching baggage claim ticket at baggage carousel ID ABC; (N8) customer mobile device application NFC; and (N9) exit ID QRS. The output attribute is baggage item stolen or not stolen and is also a Boolean value. The same network architecture as the second example examples was used.

| AVAILABLE DATA SET (PRE-SHUFFLING) | | | | | | | | | |
|---|---|---|---|---|---|---|---|---|---|
| N1 | N2 | N3 | N4 | N5 | N6 | N7 | N8 | N9 | OUTPUT |
| 1 | 1 | 1 | 1 | 1 | 1 | 1 | 1 | 1 | 0 |
| 1 | 1 | 1 | 1 | 1 | 1 | 1 | 0 | 1 | 0 |
| 1 | 1 | 1 | 1 | 1 | 1 | 0 | 1 | 1 | 0 |
| 1 | 1 | 1 | 1 | 1 | 1 | 0 | 0 | 1 | 1 |
| 1 | 1 | 1 | 1 | 1 | 1 | 0 | 0 | 0 | 0 |
| 1 | 1 | 1 | 1 | 1 | 1 | 1 | 1 | 0 | 0 |
| 1 | 1 | 1 | 1 | 1 | 1 | 0 | 0 | 1 | 1 |

Figure 32D:
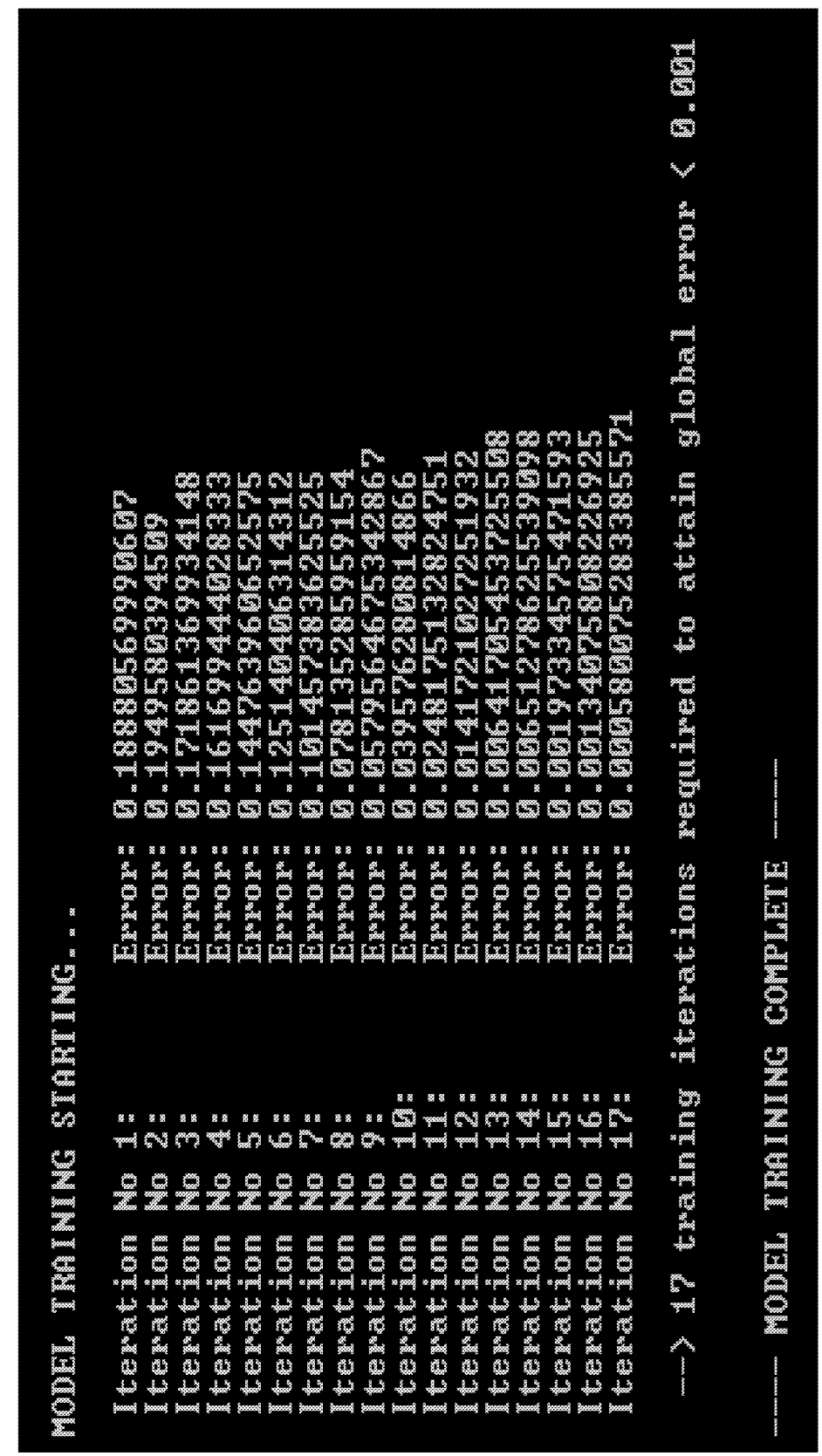

Referring to FIG. 32D, the output of each training iteration in this demonstrative example is shown. A total of 17 training iterations were required before an acceptable global error level was attained.

Now that the exemplary neural network model is trained and "learned," it is ready to undergo validation. For the purpose of this exemplary embodiment, the training data is passed into the trained model to assess its performance.

The trained model's performance with this training data set are shown in FIG. 33D. For each input, the trained model's predicted output nicely approximates the ideal output providing evidence that the model is performant at predicting the outcome in all presented cases.

It should be emphasized that the above four examples are given merely to illustrate the concepts of the embodiments discussed herein. Other input attributes such as, for example, weight of the baggage item (over 20 kg or not), check-in time (airport peak usage time or not), number of connections in the baggage travel path, etc. can be used. Other example predicted outputs include shrinkage such as theft can be used. Below example code for cases: Deviation; Shrinkage; and Security Threat is shown.

```
private const string _deviation = "DEVIATION";
private const string _shrinkage = "SHRINKAGE";
private const string _securityThreat = "SECURITY_THREAT";
private static void Main(string[ ] args)
{
  var selectedCase = _securityThreat;
  double[ ] [ ] exemplaryEmbodimentInput = { };
  double[ ] [ ] exemplaryEmbodimentOutput = { };
  switch (selectedCase)
  {
    case _deviation :
      // -- deviation -- //
      exemplaryEmbodimentInput = new [ ]
      {
        new[ ] {1.0, 0.0, 0.0, 0.0, 0.0, 0.0, 0.0, 0.0, 0.0},
        new[ ] {1.0, 1.0, 0.0, 0.0, 0.0, 0.0, 0.0, 0.0, 0.0},
        new[ ] {1.0, 1.0, 1.0, 0.0, 0.0, 0.0, 0.0, 0.0, 0.0},
        new[ ] {1.0, 1.0, 1.0, 1.0, 0.0, 0.0, 0.0, 0.0, 0.0},
        new[ ] {1.0, 1.0, 1.0, 1.0, 1.0, 1.0, 1.0, 1.0, 1.0},
        new[ ] {1.0, 1.0, 1.0, 1.0, 1.0, 0.0, 0.0, 0.0, 0.0},
        new[ ] {1.0, 1.0, 1.0, 1.0, 1.0, 1.0, 0.0, 0.0, 0.0},
        new[ ] {1.0, 1.0, 1.0, 1.0, 1.0, 1.0, 1.0, 0.0, 0.0},
        new[ ] {1.0, 1.0, 1.0, 1.0, 1.0, 1.0, 1.0, 1.0, 0.0},
        new[ ] {1.0, 1.0, 1.0, 1.0, 1.0, 1.0, 1.0, 1.0, 1.0},
        new[ ] {1.0, 1.0, 1.0, 1.0, 1.0, 1.0, 1.0, 1.0, 0.0},
        new[ ] {1.0, 1.0, 1.0, 1.0, 1.0, 1.0, 1.0, 0.0, 0.0},
        new[ ] {1.0, 1.0, 1.0, 1.0, 1.0, 1.0, 0.0, 0.0, 0.0},
        new[ ] {1.0, 1.0, 1.0, 1.0, 1.0, 0.0, 0.0, 0.0, 0.0},
        new[ ] {1.0, 1.0, 1.0, 1.0, 0.0, 0.0, 0.0, 0.0, 0.0},
        new[ ] {1.0, 1.0, 1.0, 1.0, 1.0, 1.0, 1.0, 1.0, 1.0},
        new[ ] {1.0, 1.0, 1.0, 0.0, 0.0, 0.0, 0.0, 0.0, 0.0},
        new[ ] {1.0, 1.0, 0.0, 0.0, 0.0, 0.0, 0.0, 0.0, 0.0},
        new[ ] {1.0, 0.0, 0.0, 0.0, 0.0, 0.0, 0.0, 0.0, 0.0},
        new[ ] {1.0, 1.0, 1.0, 1.0, 1.0, 1.0, 1.0, 1.0, 1.0}
      };
      exemplaryEmbodimentOutput = new [ ]
      {
        new[ ] {1.0},
        new[ ] {1.0},
        new[ ] {1.0},
        new[ ] {1.0},
        new[ ] {0.0},
        new[ ] {1.0},
        new[ ] {1.0},
        new[ ] {1.0},
        new[ ] {1.0},
        new[ ] {0.0},
        new[ ] {1.0},
        new[ ] {1.0},
        new[ ] {1.0},
        new[ ] {1.0},
        new[ ] {1.0},
```

```
          new[ ] {0.0},
          new[ ] {1.0},
          new[ ] {1.0},
          new[ ] {1.0},
          new[ ] {0.0},
      };
      break;
  case _shrinkage :
      // -- shrinkage / larceny / theft -- //
      exemplaryEmbodimentInput = new[ ]
      {
          new[ ] {1.0, 1.0, 1.0, 1.0, 1.0, 1.0, 1.0, 1.0, 1.0},
          new[ ] {1.0, 1.0, 1.0, 1.0, 1.0, 1.0, 1.0, 0.0, 1.0},
          new[ ] {1.0, 1.0, 1.0, 1.0, 1.0, 1.0, 0.0, 1.0, 1.0},
          new[ ] {1.0, 1.0, 1.0, 1.0, 1.0, 1.0, 0.0, 0.0, 1.0},
          new[ ] {1.0, 1.0, 1.0, 1.0, 1.0, 1.0, 0.0, 0.0, 0.0},
          new[ ] {1.0, 1.0, 1.0, 1.0, 1.0, 1.0, 1.0, 1.0, 1.0},
          new[ ] {1.0, 1.0, 1.0, 1.0, 1.0, 1.0, 0.0, 0.0, 1.0},
      };
      exemplaryEmbodimentOutput = new[ ]
      {
          new[ ] {0.0},
          new[ ] {0.0},
          new[ ] {0.0},
          new[ ] {1.0},
          new[ ] {0.0},
          new[ ] {0.0},
          new[ ] {1.0},
      };
      break;
  case _securityThreat :
      // -- security threat -- //
      exemplaryEmbodimentInput = new[ ]
      {
          new[ ] {0.0, 0.0, 0.0, 0.0, 1.0, 1.0, 1.0, 1.0, 1.0 },
          new[ ] {1.0, 1.0, 1.0, 0.0, 1.0, 1.0, 1.0, 1.0, 1.0 },
          new[ ] {0.0, 0.0, 0.0, 0.0, 0.0, 1.0, 1.0, 1.0, 1.0 },
          new[ ] {0.0, 0.0, 0.0, 0.0, 0.0, 0.0, 1.0, 1.0, 1.0 },
          new[ ] {0.0, 0.0, 0.0, 0.0, 0.0, 0.0, 0.0, 1.0, 1.0 },
          new[ ] {1.0, 1.0, 1.0, 1.0, 1.0, 1.0, 1.0, 1.0, 1.0 },
          new[ ] {1.0, 1.0, 1.0, 1.0, 1.0, 1.0, 1.0, 1.0, 1.0 },
          new[ ] {0.0, 1.0, 1.0, 1.0, 1.0, 1.0, 1.0, 1.0, 1.0 },
          new[ ] {1.0, 0.0, 1.0, 1.0, 1.0, 1.0, 1.0, 1.0, 1.0 },
          new[ ] {1.0, 1.0, 1.0, 1.0, 1.0, 1.0, 1.0, 1.0, 1.0 },
          new[ ] {0.0, 1.0, 1.0, 1.0, 1.0, 1.0, 1.0, 1.0, 1.0 },
          new[ ] {0.0, 0.0, 0.0, 0.0, 1.0, 1.0, 1.0, 1.0, 1.0 },
          new[ ] {1.0, 1.0, 1.0, 0.0, 1.0, 1.0, 1.0, 1.0, 1.0 },
          new[ ] {0.0, 0.0, 0.0, 0.0, 0.0, 1.0, 1.0, 1.0, 1.0 },
          new[ ] {0.0, 0.0, 0.0, 0.0, 0.0, 0.0, 1.0, 1.0, 1.0 },
          new[ ] {0.0, 0.0, 0.0, 0.0, 0.0, 0.0, 0.0, 1.0, 1.0 },
          new[ ] {1.0, 1.0, 1.0, 1.0, 1.0, 1.0, 1.0, 1.0, 1.0 },
          new[ ] {1.0, 1.0, 1.0, 1.0, 1.0, 1.0, 1.0, 1.0, 1.0 },
          new[ ] {0.0, 1.0, 1.0, 1.0, 1.0, 1.0, 1.0, 1.0, 1.0 },
          new[ ] {1.0, 1.0, 1.0, 1.0, 1.0, 1.0, 1.0, 1.0, 1.0 },
      };
      exemplaryEmbodimentOutput = new[ ]
      {
          new[ ] {1.0},
          new[ ] {1.0},
          new[ ] {1.0},
          new[ ] {1.0},
          new[ ] {1.0},
          new[ ] {0.0},
          new[ ] {0.0},
          new[ ] {0.0},
          new[ ] {0.0},
          new[ ] {0.0},
          new[ ] {1.0},
          new[ ] {1.0},
          new[ ] {1.0},
          new[ ] {1.0},
          new[ ] {1.0},
          new[ ] {0.0},
          new[ ] {0.0},
          new[ ] {0.0},
          new[ ] {0.0},
          new[ ] {0.0},
      };
      break;
  }
  var trainingSet = new
BasicMLDataSet(exemplaryEmbodimentInput,
exemplaryEmbodimentOutput);
      var network = CreateNetwork( );
      // training algorithim that will be used to train the network
      var train = new ResilientPropagation(network, trainingSet);
      // TRAIN THE MODEL
      Console.WriteLine("\n      MODEL     TRAINING
STARTING...\n");
      var epoch = 1;
      do
      {
          //
          train.Iteration( );
          // write iteration number and training error to console
          Console.WriteLine(" Iteration No {0}: \tError: {1}", epoch,
train.Error);
          // epoch will increase by 1 in each iteration
          epoch++;
          // check value of training error at end of each iteration
(terminating condition)
          // predefined limit value set to 0.001
      } while (train.Error > 0.001);
      Console.WriteLine("\n --> {0} training iterations required to
attain global error < 0.001\n", epoch - 1);
      Console.WriteLine("/n ---- MODEL TRAINING COMPLETE
----\n\n\n");
      // EVALUATE THE MODEL
      Console.WriteLine(" MODEL VALIDATION PROCEDURE
STARTING...\n")
      // in this simplistic exemplary embodiment we pass the model
the training set data again
      foreach (var item in trainingSet)
      {
          // pass in row in data set
          var output = network.Compute(item.Input);
          // write output to console
          switch (selectedCase)
          {
              case _deviation:
                  // -- deviation -- //
                  Console.WriteLine(
                      " Input: {0:0.0}, {1:0.0}, {2:0.0}, {3:0.0}, {4:0.0},
{5:0.0}, {6:0.0}, {7:0.0}, {8:0.0}
                      \tIdeal: {9:0.0} \tPredicted: {10}",
                      item.Input[0],       item.Input[1],       item.Input[2],
item.Input[3], item.Input[4], item.Input[5],
                      item.Input[6],       item.Input[7],       item.Input[8],
item.Ideal[0], output[0]);
                  break;
              case _shrinkage :
                  // -- shrinkage -- //
                  Console.WriteLine(
                      " Input: {0:0.0}, {1:0.0}, {2:0.0}, {3:0.0}, {4:0.0},
{5:0.0}, {6:0.0}, {7:0.0}, {8:0.0}
                      \tIdeal: {9:0.0} \tPredicted: {10}",
                      item.Input[0],       item.Input[1],       item.Input[2],
item.Input[3], item.Input[4], item.Input[5],
                      item.Input[6],       item.Input[7],       item.Input[8],
item.Ideal[0], output[0]);
                  break;
              case _securityThreat:
                  // -- shrinkage -- //
                  Console.WriteLine(
                      " Input: {0:0.0}, {1:0.0}, {2:0.0}, {3:0.0}, {4:0.0},
{5:0.0}, {6:0.0}, {7:0.0}, {8:0.0}
                      \tIdeal: {9:0.0} \tPredicted: {10}",
                      item.Input[0],       item.Input[1],       item.Input[2],
item.Input[3], item.Input[4], item.Input[5],
                      item.Input[6],       item.Input[7],       item.Input[8],
item.Ideal[0], output[0]);
                  break;
```

```
         }
      }
         Console.WriteLine("\n  ----  MODEL  VALIDATION
COMPLETE ----\n");
         Console.ReadLine( );
private static BasicNetwork CreateNetwork( )
   {
      var network = new BasicNetwork( );
      // input layer, 3 neurons, with bias neuron, no activation fxn
      network.AddLayer(new BasicLayer(null, true, 9));
      // hidden layer, 3 neurons, with bias neuron, sigmoid
activation fxn
         network.AddLayer(new       BasicLayer(new
ActivationSigmoid( ), true, 9));
      // output layer, 1 neuron, no bias neuron, sigmoid activation
fxn
         network.AddLayer(new       BasicLayer(new
ActivationSigmoid( ), false, 1));
         network.Structure.FinalizeStructure( );
         // randomly initialize network synaptic weights
         network.Reset( );
         return network;
   }Example Code
```

Figure 36:
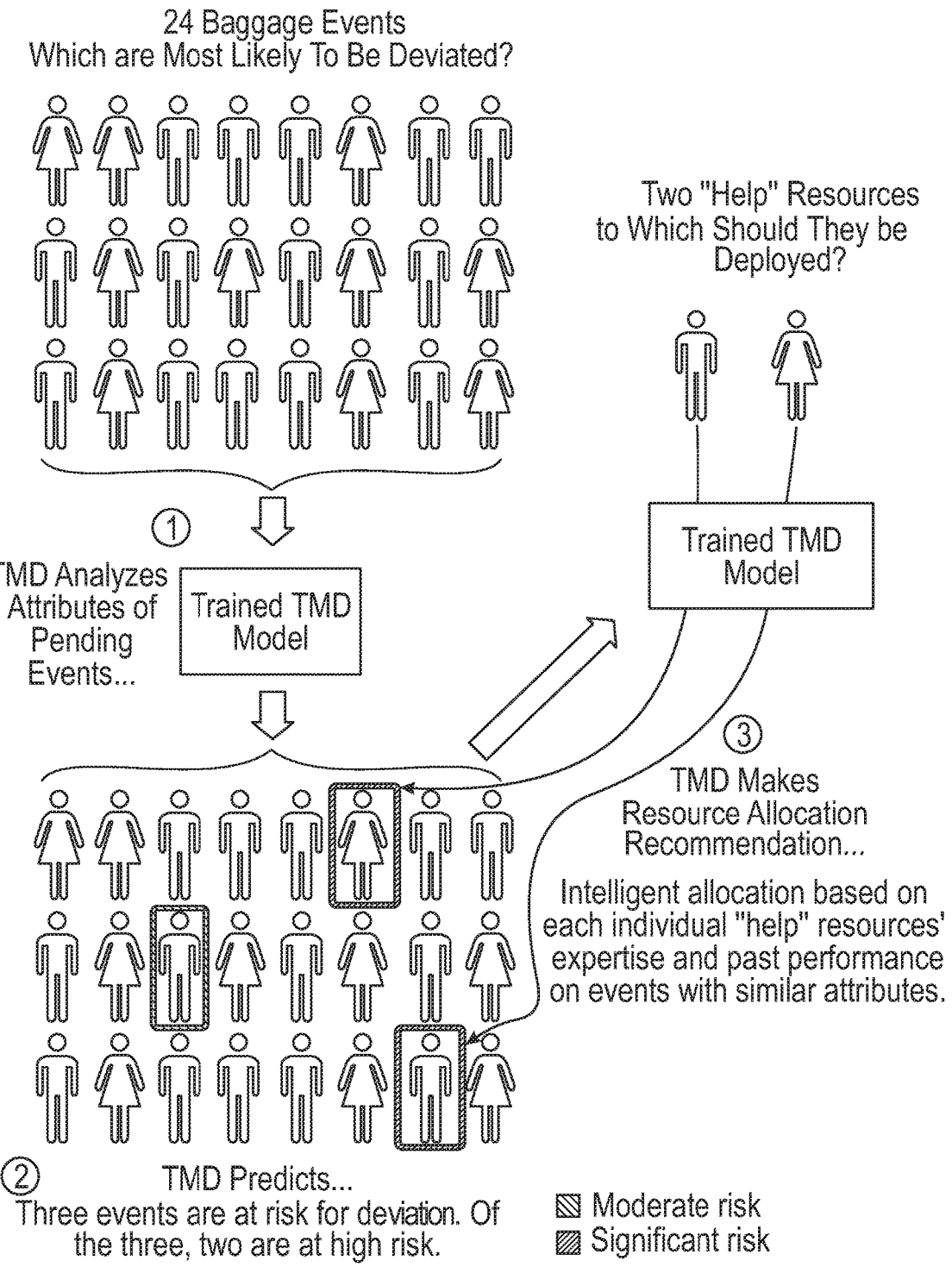
FIG. 36 is an illustration of an exemplary use case in which the trained TMD device determines a deviation risk for a plurality of baggage events and to which of the baggage events resources should be deployed.

Referring to FIG. 36, the backend devices (TMD and server) can use trained models such as the NNM and/or SOM to predict outputs (e.g., which events are at risk for deviation) as described. The backend devices are capable of using their trained models to determine to which, if any, events more resources should be allocated (i.e. the backend devices can determine whether there is an opportunity, or more specifically, a high probability, of successfully mitigating the likelihood of a given predicted deviation by allocating additional resource(s)). Particularly, to do this, the controller of the TMD may utilize a NNM that takes inputs such as deviation risk category (moderate or significant risk for delay) of the event, attributes of the baggage item and the departure airport, etc.

In doing so, the TMD can determine whether (the probability that) deployment of any given available resource(s) is likely to mitigate the predicted deviation for a given baggage event that is pending fulfillment; moreover, the TMD's NNMs can predict the quantity or duration of time by which the probability of deviation would potentially be reduced if a given resource allocation recommendation is made. Based on business logic and these results, the TMD may determine it does or does not recommend that any of the available additional resources be deployed. There are a number of approaches the TMD could take to arrive at a decision to recommend or not recommend the deployment of any available resource(s). One demonstrative approach the TMD might take would be to recommend the deployment of an available resource if the probability weighted reduction in the predicted deviation exceeded a particular threshold. If more than one potential allocation of available resources might be feasible at any given time, the business logic of the TMD, for example, could be configured such that the TMD issues the recommendation that in the net (summed together) results in the largest probability weighted reduction for the airport baggage system as a whole at that moment—i.e. the constellation of recommendations at that moment that collectively has the maximum potential beneficial impact (probability weighted delay duration reduction) for the system in question. Those skilled in the art know there is a broad set of approaches that the system may take to make such recommendations and the approaches can further vary depending on the specific optimization objective(s). Moreover, while in practice the optimization technique employed may be more complex, the embodiment herein was selected to provide a simple demonstrative example of one of many potential optimization approaches the system might take. The resource allocation example herein is not intended to limit the scope of potential approaches to that described.

The performance metric, predictions, and other data generated by inventive system can be accessed via the backend device API and pulled into other third party user facing applications. The data can also be viewed by an authenticated and authorized end user in the graphical user interface of one of the system's client devices. Various views and transformations of the performance metric data can be provided.

The system enables its customers and end users to gain insights about their performance on various metrics of interest and to predict particular outcomes of interest. The customers/end users can slice the data and view it from perspectives that are of particular value to their organization. Within many airport terminals a plurality of workers are involved in the transition of a baggage item. One benefit of the system is its ability to report relevant data it generates based on relationships between a plurality of related or unrelated workers and information in the system related to them (for example, any interactions the workers may have had with specific baggage items, and various related data or attributes about each of these that the system captures) over particular time ranges of interest. One of the system's client devices that communicates with the backend device can produce a dashboard tailored to the logged in end user's desired settings (i.e. which metrics to show, for what time ranges, etc.) and any restrictions thereof resulting from settings configured by authorized system administrators. End users can have saved views in addition to a system or user set default view. The end user can create ad hoc views as well and save them as saved views. The end user can interact with the dashboard to view the various metrics from different perspectives (drill up/drill down, change time range, view raw underlying data, etc.). The user can do this using various client device peripherals (touch screen, key board, mouse, microphone—voice commands . . . i.e. voice data that is streamed to a voice to text engine, transcribed, and interpreted by a machine, etc. For example a user could verbally "ask" that particular metric(s) of interest be fetched and shown in accordance with any criteria verbally provided and based upon parsing of the transcript returned, the system would attempt to fulfil the transcribed verbal request). One of the system's client devices can also be configured and used to operate a monitor or television (i.e. a large, flat screen monitor or TV). The client device's controller can run instructions native to the device or remotely received from the backend device to display data and metrics on the large screen graphical user interface. The client device may show a pre-defined sequence of metrics which loops and plays continuously or an authorized end user can interact with the client device via the large screen graphical interface. The large screen graphical user interface can be place in a secured area within an organization where access is controlled and only authorized personnel can enter and be used to communicate real time data and various performance metrics of interest that are being tracked by the system. The large screen graphical user interface can also be used and controlled by an authenticated and authorized end user during a meeting to display information or be used as a part of a virtual meeting (i.e. a web conference call).

The TMD or a client device running an application that communicates with the TMD can generate a graphical display which displays an average deviation percentage for various terminals of an airport. Particularly, a client device can request this graphical display from the TMD or the underlying data required to generate it. The TMD can store the values or calculate them from data retrieved from the database of the server device.

Therefore, the present disclosure concerns machine learning models, the disclosure's application of specific technical techniques that leverage the specific aspects or attributes of particular care transitions in airport baggage systems in conjunction with the other system components (for example, the RFID tag interaction with the DCE and the DCE's communication with the TMD) that permit the identification of the true state of facility operations.

While only certain features of the invention have been illustrated and described herein, many modifications and changes will occur to those of ordinary skill in the art. The following claims are intended to cover all such modifications and changes.

What is claimed is:

1. A baggage system comprising:
a belt loader reader device configured to communicate with a radio-frequency identification (RFID) tag associated with a baggage item, wherein the belt loader reader device comprises:
an RFID antenna;
a power transmission subsystem including a power source and an antenna arranged to wirelessly transmit power from the power source to the RFID tag;
a transceiver configured to receive first data from the RFID tag, the first data including identification information;
a controller operatively coupled to the transceiver; and
one or more memory sources operatively coupled to the controller, the one or more memory sources including instructions for configuring the controller to generate one or more messages indicative of the identification information to be sent by the transceiver to a server device via a network connection,
wherein the server device comprises:
a transceiver configured to receive the one or more messages from the belt loader reader device;
a controller operatively coupled to the transceiver; and
one or more memory sources operatively coupled to the controller, the one or more memory sources including instructions for configuring the controller to generate another message indicative of the identification information associated with the baggage item.

2. The baggage system of claim 1, wherein in the server device the one or more memory sources store a database including baggage item identifications and attributes of each of the baggage item identifications, the attributes indicative of whether each of the baggage item identifications is authorized for being loaded, the instructions further configure the controller of the server device to generate a stop message to be sent by the transceiver to the belt loader reader device when the controller determines that the attribute associated with the identification information associated with the RFID tag indicates that the baggage item is not authorized for being loaded.

3. The baggage system of claim 2, wherein the belt loader reader device is further configured to stop motion of a conveyor belt in response to the stop message received from the server device.

4. The baggage system of claim 1, wherein in the server device the one or more memory sources store a database including baggage item identifications and attributes of each of the baggage item identifications, the attributes indicative of a destination route of each of the baggage item identifications, the instructions further configure the controller of the server device to generate a stop message to be sent by the transceiver to the belt loader reader device when the controller determines that the attribute associated with the identification information associated with the RFID tag indicates that the baggage item has been misrouted from the destination route.

5. The baggage system of claim 1, wherein in the server device the one or more memory sources further store a trained model for generating an output value corresponding to a present event based upon at least the identification information.

6. The baggage system of claim 5, where the server device is further configured to:
receive a plurality of input attributes of the present event;
perform pre-processing on the plurality of input attributes to generate an input data set;
generate the output value from the trained model based upon the input data set; and
predict an outcome associated with the present event based upon the output value.

7. The baggage system of claim 1, where the server device is further configured to:
store a plurality of past events, each of the plurality of past events including a plurality of input attributes and a quantifiable outcome; and
train an NNM to generate a trained model, wherein the training of the NNM includes:
performing pre-processing on the plurality of input attributes for each of the plurality of past events to generate a plurality of input data sets;
dividing the plurality of past events into a first set of training data and a second set of validation data;
iteratively performing a machine learning algorithm (MLA) to update synaptic weights of the NNM based upon the training data; and
validating the NNM based upon the second set of validation data.

8. The baggage system of claim 1, wherein:
the one or more memory sources of the server device further store a trained model for generating an output value corresponding to a present event based upon at least the identification information; and
the trained model is a trained Self-Organizing Map (SOM) including a plurality of network nodes arranged in a grid or lattice and in fixed topological positions, an input layer with a plurality of input nodes representing input attributes of past events, wherein each of the plurality of input nodes is connected to all of the plurality of network nodes by a plurality of synaptic weights.

9. The baggage system of claim 8, wherein the controller of the server device is further configured to:
store a plurality of past events, each of the plurality of past events including a plurality of input attributes;
perform pre-processing on the plurality of attributes for each of the plurality of past events to generate a plurality of input data sets; and
train a SOM to generate the trained model, wherein the training of the SOM includes:
initializing values of the plurality of synaptic weights to random values,
randomly selecting one past event and determining which of the plurality of network nodes is a best matching unit (BMU) according to a discriminant function, wherein the discriminant function is a Euclidean Distance; and iteratively calculating a neighborhood radius associated with the BMU to determine neighboring network nodes for updating, and updating values of synoptic weights for neighboring network nodes within the calculated neighborhood radius for a fixed number of iterations to generate the trained model.

10. The baggage system of claim 9, wherein the controller of the server device is further configured to generate another SOM including the plurality of input attributes to reduce dimensionality and thereby normalize the plurality of input attributes.

11. The baggage system of claim 1, wherein in the server device the one or more memory sources store a database including baggage item identifications and attributes of each of the baggage item identifications, wherein the another message generated by the controller of the server device includes the attributes associated with the identification of the baggage item.

12. The baggage system of claim 11,
wherein the transceiver of the belt loader reader device receives the another message from the server device;
wherein the belt loader reader device is further configured to determine whether the baggage item has been misrouted based upon the attributes in the another message received from the server device.

13. A belt loader reader device for a baggage system, comprising:
an RFID antenna;
a power transmission subsystem including a power source and an antenna arranged to wirelessly transmit power from the power source to an RFID tag associated with a baggage item;
a transceiver configured to receive first data from the RFID tag, the first data including identification information;
a controller operatively coupled to the transceiver; and
one or more memory sources operatively coupled to the controller, the one or more memory sources including instructions for configuring the controller to generate one or more messages indicative of the identification information to be sent by the transceiver to a server device via a network connection.

14. The belt loader reader device of claim 13,
wherein the transceiver of the belt loader reader device receives another message from the server device, the another message including attributes of the baggage item.

15. The belt loader reader device of claim 14, wherein the controller is further configured to determine whether the baggage item has been misrouted based upon the attributes in the another message received from the server device.

16. The belt loader reader device of claim 15, wherein the controller is further configured to generate a stop motion command when it has determined that the baggage item has been misrouted.

17. The belt loader reader device of claim 13, wherein the controller is further configured to generate a stop motion command to stop motion of a conveyor belt.

18. The belt loader reader device of claim 13, wherein the transceiver is configured to communicate with RAIN ISO 18000-6C, EPC Class 1 Gen2 compliant RFID tags.

19. The belt loader reader device of claim 13, wherein the transceiver is configured to operate in 902 MHz-928 MHz, 920 MHz-925 MHz and 860 MHz-868 MHz frequency ranges.

* * * * *